(12) United States Patent
Carr et al.

(10) Patent No.: US 8,147,832 B2
(45) Date of Patent: Apr. 3, 2012

(54) CD20-BINDING POLYPEPTIDE COMPOSITIONS AND METHODS

(75) Inventors: Francis Joseph Carr, Balmedie (GB); Stephen Williams, Alford (GB); Stephen D. Gillies, Carlisle, MA (US)

(73) Assignee: Merck Patent GmbH, Darmstadt (DE)

( * ) Notice: Subject to any disclaimer, the term of this patent is extended or adjusted under 35 U.S.C. 154(b) by 1921 days.

(21) Appl. No.: 10/917,599

(22) Filed: Aug. 13, 2004

(65) Prior Publication Data

US 2005/0069545 A1    Mar. 31, 2005

Related U.S. Application Data

(60) Provisional application No. 60/520,171, filed on Nov. 14, 2003.

(51) Int. Cl.
*C07K 19/00* (2006.01)
*C07K 16/28* (2006.01)
*C07K 16/30* (2006.01)
*A61K 39/395* (2006.01)

(52) U.S. Cl. ............... 424/133.1; 424/134.1; 424/135.1; 424/144.1; 424/153.1; 424/155.1; 424/173.1; 424/174.1; 424/178.1; 424/198.1; 424/800; 424/801; 530/387.3; 530/388.22; 530/388.73; 530/388.8; 530/388.85; 530/391.7

(58) Field of Classification Search .................. None
See application file for complete search history.

(56) References Cited

U.S. PATENT DOCUMENTS

| | | | |
|---|---|---|---|
| 5,650,150 | A | 7/1997 | Gillies |
| 6,010,902 | A | 1/2000 | Ledbetter et al. |
| 6,100,387 | A | 8/2000 | Herrmann et al. |
| 7,115,261 | B1 | 10/2006 | Lode et al. |

FOREIGN PATENT DOCUMENTS

WO    WO 02/069232 A2 *    8/2002

OTHER PUBLICATIONS

W.E. Paul, Fundamental Immunology,Chapter 9, "Structure and function of Imunoglobulins" 3rd Edition, Raven Press, 1993, pp. 292-295.*
Rudikoff et al. ,"Single amino acid substitutions altering antigen-binding specificity" Proc. Natl. Acad. Sci. USA, 79(6):1979-1983, Mar. 1982.*
Colman,"Effects of amino acid changes on antibody-antigen interaction", Research in Immunology, 145:33-36, 1994.*
Bendig, "Humanization of rodent antibodies by CDR grafting", Methods: A Companion to Methods in Enzymology, 8:8-93, 1995.*
Gillies et al., Antibody-targeted interleukin 2 stimulates T-cell killing of autologous tumor cells, Proc. Nat. Acad. Sci. USA 89:1428-1432 (Feb. 1992).
Becker et al., T cell-mediated Eradication of Murine Metastatic Melanoma Induced by Targeted Interleukin 2 Therapy, J. Exp. Med. 183:2361-2366 (May 1996).
Xiang et al., Elimination of Established Murine Colon Carcinoma Metastases by Antibody-Interleukin 2 Fusion Protein Therapy, Cancer Research 57:4948-4955 (Nov. 1, 1997).

* cited by examiner

*Primary Examiner* — Ronald Schwadron
(74) *Attorney, Agent, or Firm* — Olson & Cepuritis, Ltd.

(57) ABSTRACT

A CD20-binding polypeptide composition comprising a combination of a modified heavy chain variable region polypeptide and a modified light chain variable region polypeptide. The combination can be (a) a modified 2B8 antibody heavy chain variable region polypeptide of SEQ ID NO: 48; and a modified 2B8 antibody light chain variable region polypeptide of SEQ ID NO: 49; or (b) a modified Leu16 antibody heavy chain variable region polypeptide of SEQ ID NO: 50; and a modified Leu16 antibody light chain variable region polypeptide of SEQ ID NO: 51.

19 Claims, 26 Drawing Sheets

QVQLQQPGAELVKAGASVKMSCKASGYTFTSYNMHWVKQTPGRGLEWIGAIYPGNGDTS
YNQKFKGKATLTADKSSSTAYMQLSSLTSEDSAVYYCARSTYYGGDTYFNVWGAGTTVT
VSA (SEQ ID NO: 1)

VhC:

QVQLQQPGAELKKPGASVKVSCKASGYTFTSYNMHWVKQTPGRGLEWTGAIYPGNGDTS
YNQKFKGKTTLTADKSSSTAYMELSSLRSEDTAVYYCARSTYYGGDWYFNVWGAGTTVT
VSA (SEQ ID NO: 2)

VhD:

QVQLQQPGAELKKPGASVKVSCKASGYTFTSYNMHWVKQTPGRGLEWIGAIYPGNGDTS
YNQKFKGKTTLTADKSSSTAYMELSSLRSEDTAVYYCARSTYYGGDWYFNVWGAGTTVT
VSA (SEQ ID NO: 3)

QIVLSQSPAILSASPGEKVTMTCRASSSVSYIHWFQQKPGSSPKPWIYATSNLASGVPV
RFSGSGSGTSYSLTISRVEAEDAATYYCQQWTSNPPTFGGGTKLEIK
(SEQ ID NO: 4)

VkA:

QIVLSQSPAIITASPGEKVTMTCRASTSASYIHWFQQKPTSSPKPWIYATSNLASGVPS
RFSGSGSGTTYSMTISSLEAEDAATYYCQQWTSNPPTFGGGTKLEIK
(SEQ ID NO: 5)

VkB:

QIVLSQSPAIITASPGEKVTMTCRASTSVSYIHWFQQKPTSSPKPWIYATSNLASGVPS
RFSGSGSGTTYSMTISSLEAEDAATYYCQQWTSNPPTFGGGTKLEIK
(SEQ ID NO: 6)

VkC:

QIVLSQSPAIITASPGEKVTMTCRASTSVSYIHWFQQKPGSSPKPWIYATSNLASGVPS
RFSGSGSGTTYSMTISSLEAEDAATYYCQQWTSNPPTFGGGTKLEIK
(SEQ ID NO: 7)

VkD:

QIVLSQSPAIITASPGEKVTMTCRASSSVSYIHWFQQKPGSSPKPWIYATSNLASGVPS
RFSGSGSGTTYSMTISSLEAEDAATYYCQQWTSNPPTFGGGTKLEIK
(SEQ ID NO: 8)

Figure 3

Leu-16Vh:

EVQLQQSGAELVKPGASVKMSCKASGYTFTSYNMHWVKQTPGQGLEWIGA
IYPGNGDTSYNQKFKGKATLTADKSSSTAYMQLSSLTSEDSADYYCARSN
YYGSSYWFFDVWGAGTTVTVSS (SEQ ID NO: 9)

Leu-16VhY:

EVQLQQSGAELKKPGASVKVSCKASGYTFTSYNMHWVKQTPGQGLEWIGA
IYPGNGDTSYNQKFKGKTTLTADKSSSTAYMELSSLRSEDTAVYYCARSN
YYGSSYWFFDVWGTGTTVTVSS (SEQ ID NO: 10)

Figure 4

Leu-16Vk:

DIVLTQSPAILSASPGEKVTMTCRASSSVNYMDWYQKKPGSSPKPWIYAT
SNLASGVPARFSGSGSGTSYSLTISRVEAEDAATYYCQQWSFNPPTFGGG
TKLEIK (SEQ ID NO: 11)

Leu-16VkZ:

DIVLTQSPAIITASPGEKVTMTCRASSSVNYMDWYQKKPGSSPKPWIYAT
SNLASGVPSRFSGSGSGTTYSMTISSLEAEDAATYYCQQWSFNPPTFGGG
TKLEIK (SEQ ID NO: 12)

Figure 16

Heavy chain variable region (Vh) sequences of anti-CD20 antibodies

```
            1                                                 50
            |         |         |         |         |
2B8Vh       QVQLQQPGAELVKAGASVKMSCKASGYTFTSYNMHWVKQTPGRGLEWIGA
2B8VhC      QVQLQQPGAELKKPGASVKVSCKASGYTFTSYNMHWVKQTPGRGLEWTGA
2B8VhD      QVQLQQPGAELKKPGASVKVSCKASGYTFTSYNMHWVKQTPGRGLEWIGA
Leu16Vh     EVQLQQSGAELVKPGASVKMSCKASGYTFTSYNMHWVKQTPGQGLEWIGA
Leu16VhY    EVQLQQSGAELKKPGASVKVSCKASGYTFTSYNMHWVKQTPGQGLEWIGA
1H4 Vh      QVQLQQPGAELVKPGASVKMSCKTSGYTFTSYNVHWVKQTPGQGLEWIGA 51                                                100
            |         |         |         |         |
2B8Vh       IYPGNGDTSYNQKFKGKATLTADKSSSTAYMQLSSLTSEDSAVYYCARST
2B8VhC      IYPGNGDTSYNQKFKGKTTLTADKSSSTAYMELSSLRSEDTAVYYCARST
2B8VhD      IYPGNGDTSYNQKFKGKTTLTADKSSSTAYMELSSLRSEDTAVYYCARST
Leu16Vh     IYPGNGDTSYNQKFKGKATLTADKSSSTAYMQLSSLTSEDSADYYCARSN
Leu16VhY    IYPGNGDTSYNQKFKGKTTLTADKSSSTAYMELSSLRSEDTAVYYCARSN
1H4 Vh      IYPGNGDTSFNQKFKGKATLTADKSSSTVYMQLSSLTSEDSAVYYCARSN 101              122
            |         |     |
2B8Vh       YYGGD--TYFNVWGAGTTVTVSA     (SEQ ID NO: 1)
2B8VhC      YYGGD--WYFNVWGAGTTVTVSA     (SEQ ID NO: 2)
2B8VhD      YYGGD--WYFNVWGAGTTVTVSA     (SEQ ID NO: 3)
Leu16Vh     YYGSSY-WFFDVWGAGTTVTVSS     (SEQ ID NO: 9)
Leu16VhY    YYGSSY-WFFDVWGTGTTVTVSS     (SEQ ID NO: 10)
1H4 Vh      YYGSSYVWFFDVWGAGTTGTGSS     (SEQ ID NO: 13)
```

Figure 16 (Contd.)

Light chain variable region (Vk) sequences of anti-CD20 antibodies

```
            1         |         |         |         |        50
2B8Vk       QIVLSQSPAILSASPGEKVTMTCRASSSVSYIHWFQQKPGSSPKPWIYAT
2B8VkA      QIVLSQSPAIITASPGEKVTMTCRASTSASYIHWFQQKPTSSPKPWIYAT
2B8VkB      QIVLSQSPAIITASPGEKVTMTCRASTSVSYIHWFQQKPTSSPKPWIYAT
2B8VkC      QIVLSQSPAIITASPGEKVTMTCRASTSVSYIHWFQQKPGSSPKPWIYAT
2B8VkD      QIVLSQSPAIITASPGEKVTMTCRASSSVSYIHWFQQKPGSSPKPWIYAT
Leu16Vk     DIVLTQSPAILSASPGEKVTMTCRASSSVNYMDWYQKKPGSSPKPWIYAT
Leu16VkZ    DIVLTQSPAIITASPGEKVTMTCRASSSVNYMDWYQKKPGSSPKPWIYAT
1H4 Vk      QIVLSQSPTILSASPGEKVTMTCRASSSVSYMDWYQQKPGSSPKPWIYAT

51        |         |         |         |       100
2B8Vk       SNLASGVPVRFSGSGSGTSYSLTISRVEAEDAATYYCQQWTSNPPTFGGG
2B8VkA      SNLASGVPSRFSGSGSGTTYSMTISSLEAEDAATYYCQQWTSNPPTFGGG
2B8VkB      SNLASGVPSRFSGSGSGTTYSMTISSLEAEDAATYYCQQWTSNPPTFGGG
2B8VkC      SNLASGVPSRFSGSGSGTTYSMTISSLEAEDAATYYCQQWTSNPPTFGGG
2B8VkD      SNLASGVPSRFSGSGSGTTYSMTISSLEAEDAATYYCQQWTSNPPTFGGG
Leu16kK     SNLASGVPARFSGSGSGTSYSLTISRVEAEDAATYYCQQWSFNPPTFGGG
Leu16VkZ    SNLASGVPSRFSGSGSGTTYSMTISSLEAEDAATYYCQQWSFNPPTFGGG
1H4 Vk      SNLASGVPARFSGSGSGTSYSLTISRVEAEDAATYYCQQWISNPPTFGAG 101
2B8Vk       TKLEIK    (SEQ ID NO: 4)
2B8VkA      TKLEIK    (SEQ ID NO: 5)
2B8VkB      TKLEIK    (SEQ ID NO: 6)
2B8VkC      TKLEIK    (SEQ ID NO: 7)
2B8VKD      TKLEIK    (SEQ ID NO: 8)
Leu16Vk     TKLEIK    (SEQ ID NO: 11)
Leu16VkZ    TKLEIK    (SEQ ID NO: 12)
1H4 Vk      TKLELK    (SEQ ID NO: 14)
```

Figure 17

SEQ ID NO: 1 – Heavy chain V region of the 2B8 antibody

QVQLQQPGAELVKAGASVKMSCKASGYTFTSYNMHWVKQTPGRGLEWIGAIYPGNGDTSYNQKFKG
KATLTADKSSSTAYMQLSSLTSEDSAVYYCARSTYYGGDTYFNVWGAGTTVTVSA

SEQ ID NO: 2 – Heavy chain V region VhC

QVQLQQPGAELKKPGASVKVSCKASGYTFTSYNMHWVKQTPGRGLEWTGAIYPGNGDTSYNQKFKG
KTTLTADKSSSTAYMELSSLRSEDTAVYYCARSTYYGGDWYFNVWGAGTTVTVSA

SEQ ID NO: 3 – Heavy chain V region VhD

QVQLQQPGAELKKPGASVKVSCKASGYTFTSYNMHWVKQTPGRGLEWIGAIYPGNGDTSYNQKFKG
KTTLTADKSSSTAYMELSSLRSEDTAVYYCARSTYYGGDWYFNVWGAGTTVTVSA

SEQ ID NO: 4 – Light chain V region of the 2B8 antibody

QIVLSQSPAILSASPGEKVTMTCRASSSVSYIHWFQQKPGSSPKPWIYATSNLASGVPVRFSGSGS
GTSYSLTISRVEAEDAATYYCQQWTSNPPTFGGGTKLEIK

SEQ ID NO: 5 – Light chain V region VkA

QIVLSQSPAIITASPGEKVTMTCRASTSASYIHWFQQKPTSSPKPWIYATSNLASGVPSRFSGSGS
GTTYSMTISSLEAEDAATYYCQQWTSNPPTFGGGTKLEIK

SEQ ID NO: 6 – Light chain V region VkB

QIVLSQSPAIITASPGEKVTMTCRASTSVSYIHWFQQKPTSSPKPWIYATSNLASGVPSRFSGSGS
GTTYSMTISSLEAEDAATYYCQQWTSNPPTFGGGTKLEIK

SEQ ID NO: 7 – Light chain V region VkC

QIVLSQSPAIITASPGEKVTMTCRASTSVSYIHWFQQKPGSSPKPWIYATSNLASGVPSRFSGSGS
GTTYSMTISSLEAEDAATYYCQQWTSNPPTFGGGTKLEIK

SEQ ID NO: 8 – Light chain V region VkD

QIVLSQSPAIITASPGEKVTMTCRASSSVSYIHWFQQKPGSSPKPWIYATSNLASGVPSRFSGSGS
GTTYSMTISSLEAEDAATYYCQQWTSNPPTFGGGTKLEIK

Figure 17 (contd.)

SEQ ID NO: 9 – Heavy chain V region of the Leu-16 antibody

EVQLQQSGAELVKPGASVKMSCKASGYTFTSYNMHWVKQTPGQGLEWIGA
IYPGNGDTSYNQKFKGKATLTADKSSSTAYMQLSSLTSEDSADYYCARSN
YYGSSYWFFDVWGAGTTVTVSS

SEQ ID NO: 10 – Heavy chain V region VhY

EVQLQQSGAELKKPGASVKVSCKASGYTFTSYNMHWVKQTPGQGLEWIGA
IYPGNGDTSYNQKFKGKTTLTADKSSSTAYMELSSLRSEDTAVYYCARSN
YYGSSYWFFDVWGTGTTVTVSS

SEQ ID NO: 11 – Light chain V region of the Leu-16 antibody

DIVLTQSPAILSASPGEKVTMTCRASSSVNYMDWYQKKPGSSPKPWIYAT
SNLASGVPARFSGSGSGTSYSLTISRVEAEDAATYYCQQWSFNPPTFGGG
TKLEIK

SEQ ID NO: 12 – Light chain V region VkZ

DIVLTQSPAIITASPGEKVTMTCRASSSVNYMDWYQKKPGSSPKPWIYAT
SNLASGVPSRFSGSGSGTTYSMTISSLEAEDAATYYCQQWSFNPPTFGGG
TKLEIK

SEQ ID NO: 13 - Heavy chain V region of the 1H4 antibody

QVQLQQPGAELVKPGASVKMSCKTSGYTFTSYNVHWVKQTPGQGLEWIGA
IYPGNGDTSFNQKFKGKATLTADKSSSTVYMQLSSLTSEDSAVYYCARSN
YYGSSYVWFFDVWGAGTTGTGSS

SEQ ID NO: 14 - Light chain V region of the 1H4 antibody

QIVLSQSPTILSASPGEKVTMTCRASSSVSYMDWYQQKPGSSPKPWIYAT
SNLASGVPARFSGSGSGTSYSLTISRVEAEDAATYYCQQWISNPPTFGAG
TKLELK

Figure 17 (contd.)

SEQ ID NO: 15 – A first heavy chain V region segment of an anti-CD20 V region pair

SGAELKKPGAS

SEQ ID NO: 16 – A second heavy chain V region segment of an anti-CD20 V region pair

VSCKASGYT

SEQ ID NO: 17 – A third heavy chain V region segment of an anti-CD20 V region pair

LEWTGAIY

SEQ ID NO: 18 – A fourth heavy chain V region segment of an anti-CD20 V region pair

YNQKFKGKT

SEQ ID NO: 19 – A fifth heavy chain V region segment of an anti-CD20 V region pair

FKGKTTLTA

SEQ ID NO: 20 – A sixth heavy chain V region segment of an anti-CD20 V region pair

YMELSSLRS

SEQ ID NO: 21 – A seventh heavy chain V region segment of an anti-CD20 V region pair

SSLRSEDTAV

SEQ ID NO: 22 – A first light chain V region segment of an anti-CD20 V region pair

DWGTGTTVT

SEQ ID NO: 23 – A second light chain V region segment of an anti-CD20 V region pair

IITASPGEKV

Figure 17 (contd.)

SEQ ID NO: 24 – A third light chain V region segment of an anti-CD20 V region pair
CRASTSASY SEQ ID NO: 25 – A fourth light chain V region segment of an anti-CD20 V region pair
QQKPTSSP SEQ ID NO: 26 – A fifth light chain V region segment of an anti-CD20 V region pair
LASGVPSRF SEQ ID NO: 27 – A sixth light chain V region segment of an anti-CD20 V region pair
FSGSGSGTT SEQ ID NO: 28 – A seventh light chain V region segment of an anti-CD20 V region pair
YSMTISSLE

SEQ ID NO: 29
CEPANPSEKNSPSTQYC

SEQ ID NO: 30
MSCKASGYT

SEQ ID NO: 31
YNQKFKGKA

SEQ ID NO: 32
FKGKATLTA

SEQ ID NO: 33
YMQLSSLRS

Figure 17 (contd.)

SEQ ID NO: 34

ILSASPGEKV

SEQ ID NO: 35

LASGVPVARF

SEQ ID NO: 36

FSGSGSGTS

SEQ ID NO: 37

YSLTISRVE

SEQ ID NO: 38

CEPSNSSEKNSPSTQYC

SEQ ID NO: 39.
DNA sequence encoding the mature light chain of Leu16 comprising Leu16Vk

```
gacatcgttctgacccagtctccagcaatcttgtctgcatctccaggggagaaggtcaccatga
cctgcagagccagctcaagtgtaaattacatggactggtaccagaagaagccaggctcctcccc
caaaccttggatttatgccacatccaacctggcttctggagtccctgctcgcttctctggcagt
gggtctgggacctcttactctctcacaatcagcagagtcgaggctgaagatgctgccacttatt
actgccagcagtggagcttcaacccacccacgttcggtggtgggaccaagctggagatcaaacg
taagtggatcccgcaattctaaactctgaggggggtcggatgacgtggccattctttgcctaaag
cattgagtttactgcaaggtcagaaaagcatgcaaagccctcagaatggctgcaaagagctcca
acaaacaatttagaactttattaaggaatagggggaagctaggaagaaactcaaaacatcaag
attttaaatacgcttcttggtctccttgctataattatctgggataagcatgctgttttctgtc
tgtccctaacatgccctgtgattatccgcaaacaacacacccaagggcagaactttgttactta
aacaccatcctgtttgcttctttcctcaggaactgtggctgcaccatctgtcttcattttcccg
ccatctgatgagcagttgaaatctggaactgcctctgttgtgtgcctgctgaataacttctatc
ccagagaggccaaagtacagtggaaggtggataacgccctccaatcgggtaactcccaggagag
tgtcacagagcaggacagcaaggacagcacctacagcctcagcagcaccctgacgctgagcaaa
gcagactacgagaaacacaaagtctacgcctgcgaagtcacccatcagggcctgagctcgcccg
tcacaaagagcttcaacaggggagagtgttag
```

Figure 17 (contd.)

SEQ ID NO: 40
DNA sequence encoding an eptitope-depleted variant of the mature light chain of Leu16
comprising Leu16 VkZ
gacattgttctcacccagtctccagcaatcatcacagcatctccaggggagaaggtcacaatga
cttgcagggccagctcaagtgtaaactacatggactggtaccagaagaagccagggtcctcccc
caaaccctggatttatgccacatccaacctggcttctggagtcccttctcgcttcagtggcagt
gggtctgggactacttactctatgaccatcagcagcctcgaggctgaagatgctgccacttatt
actgccagcagtggagcttcaacccacccacgttcggaggggggaccaagctggaaatcaaacg
taagtggatcccgcaattctaaactctgaggggtcggatgacgtggccattctttgcctaaag
cattgagtttactgcaaggtcagaaaagcatgcaaagccctcagaatggctgcaaagagctcca
acaaaacaatttagaactttattaaggaataggggaagctaggaagaaactcaaaacatcaag
attttaaatacgcttcttggtctccttgctataattatctgggataagcatgctgttttctgtc
tgtccctaacatgccctgtgattatccgcaaacaacacacccaagggcagaactttgttactta
aacaccatcctgtttgcttctttcctcaggaactgtggctgcaccatctgtcttcatcttcccg
ccatctgatgagcagttgaaatctggaactgcctctgttgtgtgcctgctgaataacttctatc
ccagagaggccaaagtacagtggaaggtggataacgccctccaatcgggtaactcccaggagag
tgtcacagagcaggacagcaaggacagcacctacagcctcagcagcaccctgacgctgagcaaa
gcagactacgagaaacacaaagtctacgcctgcgaagtcacccatcagggcctgagctcgcccg
tcacaaagagcttcaacaggggagagtgttag SEQ ID NO: 41.
DNA sequence encoding the mature heavy chain of Leu16 comprising Leu16Vh
gaggtccagctccagcagtctggagctgagctggtgaagcctggggcttcagtgaagatgtcct
gcaaggcttctggatacacattcactagttataatatgcactgggtaaagcagacacctggaca
gggcctggaatggattggagctatttatccaggaaatggtgatacttcctacaatcagaagttc
aagggcaaggccacactgactgcagacaaatcctccagcacagcctacatgcagctcagcagcc
tgacatctgaagactctgctgactattactgtgcgaggagtaactactacggtagtagctactg
gttcttcgatgtctggggcgcagggaccacggtcaccgtctcttcaggtaagtaagcttttctg
gggcaggccaggcctgaccttggctttggggcagggaggggctaaggtgaggcaggtggcgcc
agccaggtgcacacccaatgcccatgagcccagacactggacgctgaacctcgcggacagttaa
gaacccaggggcctctgcgccctgggcccagctctgtcccacaccgcggtcacatggcaccacc
tctcttgcagcctccaccaagggcccatcggtcttccccctggcaccctcctccaagagcacct
ctgggggcacagcggccctgggctgcctggtcaaggactacttccccgaaccggtgacggtgtc
gtggaactcaggcgccctgaccagcggcgtgcacaccttcccggctgtcctacagtcctcagga
ctctactccctcagcagcgtggtgaccgtgccctccagcagcttgggcacccagacctacatct
gcaacgtgaatcacaagcccagcaacaccaaggtggacaagagagttggtgagaggccagcaca
gggagggagggtgtctgctggaagccaggctcagcgctcctgcctggacgcatcccggctatgc
agtcccagtccagggcagcaaggcaggccccgtctgcctcttcacccggaggcctctgcccgcc
ccactcatgctcagggagagggtcttctggcttttccccaggctctgggcaggcacaggctag
gtgcccctaacccaggccctgcacacaaaggggcaggtgctgggctcagacctgccaagagcca
tatccgggaggaccctgcccctgacctaagcccaccccaaaggccaaactctccactccctcag

Figure 17 (contd.)

ctcggacaccttctctcctcccagattccagtaactcccaatcttctctctgcagagcccaaat
cttgtgacaaaactcacacatgcccaccgtgcccaggtaagccagcccaggcctcgcctccag
ctcaaggcgggacaggtgccctagagtagcctgcatccagggacaggccccagccgggtgctga
cacgtccacctccatctcttcctcagcacctgaactcctggggggaccgtcagtcttcctcttc
cccccaaaacccaaggacaccctcatgatctcccggacccctgaggtcacatgcgtggtggtgg
acgtgagccacgaagaccctgaggtcaagttcaactggtacgtggacggcgtggaggtgcataa
tgccaagacaaagccgcgggaggagcagtacaacagcacgtaccgtgtggtcagcgtcctcacc
gtcctgcaccaggactggctgaatggcaaggagtacaagtgcaaggtctccaacaaagccctcc
cagcccccatcgagaaaaccatctccaaagccaaaggtgggacccgtggggtgcgagggccaca
tggacagaggccggctcggcccaccctctgcctgagagtgaccgctgtaccaacctctgtccc
tacagggcagccccgagaaccacaggtgtacaccctgcccccatcccgggaggagatgaccaag
aaccaggtcagcctgacctgcctggtcaaaggcttctatcccagcgacatcgccgtggagtggg
agagcaatgggcagccggagaacaactacaagaccacgcctcccgtgctggactccgacggctc
cttcttcctctatagcaagctcaccgtggacaagagcaggtggcagcaggggaacgtcttctca
tgctccgtgatgcatgaggctctgcacaaccactacacgcagaagagcctctccctgtcccgg
gtaaatga SEQ ID NO: 42
DNA sequence encoding an eptitope-depleted variant of the mature heavy chain of Leu16
comprising Leu16 VhY
gaggtacaactgcagcagtctggggctgagctgaagaagcctggggcctcagtgaaggtgtcct
gcaaggcttctggctacacatttaccagttacaatatgcactgggtaaaacagacacctggtca
gggcctggaatggattggagctatttatcccggaaatggtgatacttcctacaatcagaagttc
aaaggcaagacaacattgactgcagacaaatcctccagcacagcctacatggaactcagcagcc
tgagatctgaggacactgcggtctattactgtgcaagatcgaattactacggcagcagctactg
gttcttcgatgtctggggcaccgggaccacggtcaccgtctcttcaggtaagctttctggggca
ggccaggcctgaccttggctttggggcagggagggggctaaggtgaggcaggtggcgccagcca
ggtgcacacccaatgcccatgagcccagacactggacgctgaacctcgcggacagttaagaacc
caggggcctctgcgccctgggccagctctgtcccacaccgcggtcacatggcaccacctctct
tgcagcctccaccaagggcccatcggtcttccccctggcaccctcctccaagagcacctctggg
ggcacagcggccctgggctgcctggtcaaggactacttccccgaaccggtgacggtgtcgtgga
actcaggcgccctgaccagcggcgtgcacaccttcccggctgtcctacagtcctcaggactcta
ctccctcagcagcgtggtgaccgtgccctccagcagcttgggcacccagacctacatctgcaac
gtgaatcacaagcccagcaacaccaaggtggacaagagagttggtgagaggccagcacagggag
ggagggtgtctgctggaagccaggctcagcgctcctgcctggacgcatcccggctatgcagtcc
cagtccagggcagcaaggcaggccccgtctgcctcttcacccggaggcctctgcccgccccact
catgctcagggagagggtcttctggcttttccccaggctctgggcaggcacaggctaggtgcc
cctaacccaggccctgcacacaaggggcaggtgctgggctcagacctgccaagagccatatcc
gggaggaccctgcccctgacctaagcccaccccaaaggccaaactctccactccctcagctcgg
acaccttctctcctcccagattccagtaactcccaatcttctctctgcagagcccaaatcttgt
gacaaaactcacacatgcccaccgtgcccaggtaagccagcccaggcctcgcctccagctcaa

Figure 17 (contd.)

ggcgggacaggtgccctagagtagcctgcatccagggacaggccccagccgggtgctgacacgt
ccacctccatctcttcctcagcacctgaactcctgggggaccgtcagtcttcctcttcccccc
aaaacccaaggacaccctcatgatctcccggacccctgaggtcacatgcgtggtggtggacgtg
agccacgaagaccctgaggtcaagttcaactggtacgtggacggcgtggaggtgcataatgcca
agacaaagccgcgggaggagcagtacaacagcacgtaccgtgtggtcagcgtcctcaccgtcct
gcaccaggactggctgaatggcaaggagtacaagtgcaaggtctccaacaaagccctcccagcc
cccatcgagaaaaccatctccaaagccaaaggtgggacccgtggggtgcgagggccacatggac
agaggccggctcggcccaccctctgccctgagagtgaccgctgtaccaacctctgtccctacag
ggcagccccgagaaccacaggtgtacaccctgcccccatcacgggaggagatgaccaagaacca
ggtcagcctgacctgcctggtcaaaggcttctatcccagcgacatcgccgtggagtgggagagc
aatgggcagccggagaacaactacaagaccacgcctcccgtgctggactccgacggctccttct
tcctctatagcaagctcaccgtggacaagagcaggtggcagcaggggaacgtcttctcatgctc
cgtgatgcatgaggctctgcacaaccactacacgcagaagagcctctccctgtccccgggtaaa
tga SEQ ID NO: 43
DNA sequence encoding a fusion protein of an eptitope-depleted variant of the mature heavy chain of Leu16 comprising Leu16 VhY and the cytokine IL-2 gaggtacaactgcagcagtctggggctgagctgaagaagcctggggcctcagtgaaggtgtcct
gcaaggcttctggctacacatttaccagttacaatatgcactgggtaaaacagacacctggtca
gggcctggaatggattggagctatttatcccggaaatggtgatacttcctacaatcagaagttc
aaaggcaagacaacattgactgcagacaaatcctccagcacagcctacatggaactcagcagcc
tgagatctgaggacactgcggtctattactgtgcaagatcgaattactacggcagcagctactg
gttcttcgatgtctggggcaccgggaccacggtcaccgtctcttcaggtaagctttctggggca
ggccaggcctgaccttggctttggggcagggaggggctaaggtgaggcaggtggcgccagcca
ggtgcacacccaatgcccatgagcccagacactggacgctgaacctcgcggacagttaagaacc
cagggcctctgcgccctgggcccagctctgtcccacaccgcggtcacatggcaccacctctct
tgcagcctccaccaagggcccatcggtcttcccctggcaccctcctccaagagcacctctggg
ggcacagcggccctgggctgcctggtcaaggactacttccccgaaccggtgacggtgtcgtgga
actcaggcgccctgaccagcggcgtgcacaccttcccggctgtcctacagtcctcaggactcta
ctccctcagcagcgtggtgaccgtgccctccagcagcttgggcacccagacctacatctgcaac
gtgaatcacaagcccagcaacaccaaggtggacaagagagttggtgagaggccagcacagggag
ggagggtgtctgctggaagccaggctcagcgctcctgcctggacgcatcccggctatgcagtcc
cagtccagggcagcaaggcaggccccgtctgcctcttcacccggaggcctctgcccgccccact
catgctcagggagagggtcttctggcttttccccaggctctgggcaggcacaggctaggtgcc
cctaacccaggccctgcacacaaaggggcaggtgctgggctcagacctgccaagagccatatcc
gggaggaccctgcccctgacctaagcccacccaaaggccaaactctccactccctcagctcgg
acaccttctctcctcccagattccagtaactcccaatcttctctctgcagagcccaaatcttgt
gacaaaactcacacatgcccaccgtgcccaggtaagccagcccaggcctcgccctccagctcaa
ggcgggacaggtgccctagagtagcctgcatccagggacaggccccagccgggtgctgacacgt
ccacctccatctcttcctcagcacctgaactcctgggggaccgtcagtcttcctcttcccccc
aaaacccaaggacaccctcatgatctcccggacccctgaggtcacatgcgtggtggtggacgtg

Figure 17 (contd.)

```
agccacgaagaccctgaggtcaagttcaactggtacgtggacggcgtggaggtgcataatgcca
agacaaagccgcgggaggagcagtacaacagcacgtaccgtgtggtcagcgtcctcaccgtcct
gcaccaggactggctgaatggcaaggagtacaagtgcaaggtctccaacaaagccctcccagcc
cccatcgagaaaaccatctccaaagccaaaggtgggacccgtggggtgcgagggccacatggac
agaggccggctcggcccaccctctgccctgagagtgaccgctgtaccaacctctgtccctacag
ggcagccccgagaaccacaggtgtacaccctgcccccatcacgggaggagatgaccaagaacca
ggtcagcctgacctgcctggtcaaaggcttctatcccagcgacatcgccgtggagtgggagagc
aatgggcagccggagaacaactacaagaccacgcctcccgtgctggactccgacggctccttct
tcctctatagcaagctcaccgtggacaagagcaggtggcagcaggggaacgtcttctcatgctc
cgtgatgcatgaggctctgcacaaccactacacgcagaagagcgccaccgcgaccccgggtgca
gccccaacttcaagttctacaaagaaaacacagctgcaactggagcatctcctgctggatctcc
agatgattctgaatggaattaacaactacaagaatcccaaactcaccaggatgctcacattcaa
gttctacatgcccaagaaggccacagagctcaaacatctccagtgtctagaggaggaactcaaa
cctctggaggaagtgctaaacctcgctcagagcaaaaacttccacttaagacctagggacttaa
tcagcaatatcaacgtaatagttctggaactaaagggatccgaaacaacattcatgtgtgaata
tgctgatgagacagcaaccattgtagaattcctaaacagatggattacctttttgtcaaagcatc
atctcaacactaacttga
```

SEQ ID NO: 44

ATATPGA

SEQ ID NO: 45

LSLSPGK

1

CD20-BINDING POLYPEPTIDE COMPOSITIONS AND METHODS

CROSS-REFERENCE TO RELATED APPLICATIONS

This application claims the benefit of U.S. Provisional Application Ser. No. 60/520,171, which was filed on Nov. 14, 2003, which is incorporated herein by reference.

FIELD OF THE INVENTION

The present invention relates to polypeptide compositions that bind to CD20 antigen. More specifically, the invention relates to polypeptide compositions, such as chimeric antibodies, antibody fragments, and fusion proteins of an antibody or antibody fragment with a cytokine, which bind to human CD20 antigen. The invention also relates to methods for using the compositions diagnosis and treatment of diseases.

BACKGROUND OF THE INVENTION

There are many instances where the efficacy of a therapeutic protein is limited by an unwanted immune reaction to the therapeutic protein. Several mouse monoclonal antibodies have shown promise as therapies in a number of human disease settings but in certain cases have failed due to the induction of significant degrees of a human anti-murine antibody (HAMA) response (Schroff, R. W. et al. (1985) *Cancer Res.* 45: 879-885; Shawler, D. L. et al. (1985) *J. Immunol.* 135: 1530-1535). For monoclonal antibodies, a number of techniques have been developed in attempt to reduce the HAMA response (WOA8909622; EPA0239400; EPA0438310; WOA9106667; EPA0699755). These recombinant DNA approaches have generally reduced the mouse genetic information in the final antibody construct whilst increasing the human genetic information in the final construct to result in antibody molecules which are generally termed "humanised" antibodies.

Humanised antibodies, for the most part, are human immunoglobulins (recipient antibody) in which hypervariable region residues of the recipient are replaced by hypervariable region residues from a non-human species (donor antibody) such as mouse, rat, rabbit or primate, and this process is sometimes termed "CDR grafting". Generally additional Fv framework region (FR) residues of the human immunoglobulin are replaced by corresponding non-human residues and in some instances other substitutions are made to further restore the antibody function. Typically humanised antibodies are reconstituted into whole antibody molecules comprising two variable domains, in which all or substantially all of the hypervariable loops correspond to those of a non-human immunoglobulin and all or substantially all of the FR regions are those of a human immunoglobulin sequence. The humanised antibody will also generally comprise at least a portion of a human derived immunoglobulin constant region (Fc) (Jones et al. (1986), *Nature* 321: 522-525; Reichmann et al. (1988), *Nature* 332: 323-329). Notwithstanding, humanised antibodies have, in several cases, still elicited an immune response in patients (Issacs J. D. (1990) *Sem. Immunol.* 2: 449, 456; Rebello, P. R. et al. (1999) *Transplantation* 68: 1417-1420).

Key to the induction of an immune response is the presence within the protein of peptides that can stimulate the activity of T-cells via presentation on MHC Class II molecules, so-called "T-cell epitopes". Such T-cell epitopes are commonly defined as any amino acid residue sequence with the ability to bind to MHC Class II molecules. Implicitly, a "T-cell epitope" means an epitope which when bound to MHC molecules can be recognized by a T-cell receptor (TCR), and which can, at least in principle, cause the activation of these T-cells by engaging a TCR to promote a T-cell response.

MHC Class II molecules are a group of highly polymorphic proteins which play a central role in helper T-cell selection and activation. The human leukocyte antigen group DR (HLA-DR) are the predominant isotype of this group of proteins and isotypes HLA-DQ and HLA-DP perform similar functions. In the human population, individuals bear two to four DR alleles, two DQ and two DP alleles. The structure of a number of DR molecules has been solved and these appear as an open-ended peptide binding groove with a number of hydrophobic pockets which engage hydrophobic residues (pocket residues) of the peptide (Brown et al. *Nature* (1993) 364: 33; Stern et al. (1994) *Nature* 368: 215). Polymorphism identifying the different allotypes of Class II molecule contributes to a wide diversity of different binding surfaces for peptides within the peptide binding grove and at the population level ensures maximal flexibility with regard to the ability to recognize foreign proteins and mount an immune response to pathogenic organisms.

An immune response to a therapeutic protein proceeds via the MHC Class II peptide presentation pathway. Here exogenous proteins are engulfed and processed for presentation in association with MHC Class II molecules of the DR, DQ or DP type. MHC Class II molecules are expressed by professional antigen presenting cells (APCs), such as macrophages and dendritic cells amongst others. Engagement of a MHC Class II peptide complex by a cognate T-cell receptor on the surface of the T-cell, together with the cross-binding of certain other co-receptors such as the CD4 molecule, can induce an activated state within the T-cell. Activation leads to the release of cytokines further activating other lymphocytes such as B cells to produce antibodies or activating T killer cells as a full cellular immune response.

T-cell epitope identification is the first step to epitope elimination. Identified epitopes may be eliminated by judicious amino acid substitution or other modification strategies. Such an approach is recognized in WO98/52976 and WO00/34317 where in the latter case computational threading techniques are described as a means to identify polypeptide sequences with the potential to bind a sub-set of human MHC Class II DR allotypes and the predicted T-cell epitopes are removed by amino acid substitution within the protein of interest.

It would be desirable to identify and to remove, or at least to reduce, T-cell epitopes from a given, in principle therapeutically valuable, but originally immunogenic peptide, polypeptide or protein. One of these therapeutically valuable molecules is a monoclonal antibody with binding specificity for the human B-cell antigen CD20. The preferred monoclonal antibodies of the present invention are modified forms of the antibody 2B8 and Leu16. Antibody 2B8 is described in U.S. Pat. No. 5,736,137, the disclosure of which is incorporated herein by reference. Antibody Leu16 is described in Wu et al. *Protein Engineering* (2001) 14:1025-1033, the disclosure of which is incorporated herein by reference.

CD20 is a non-glycosylated phosphoprotein of 35,000 Daltons, typically designated as the human B lymphocyte restricted differentiation antigen Bp35B. The protein is a highly cell specific surface molecule expressed on pre-B and mature B-cells including greater than 90% of B-cell non-Hodgkin's lymphomas (NHL). Monoclonal antibodies and radioimmunoconjugates targeting CD20 have emerged as new treatments for NHL. The most significant example includes the parental antibody of the present invention, namely monoclonal antibody 2B8 (Reff, M. E. et al. (1994) *Blood* 83: 435-445). The variable region domains of 2B8 have been cloned and combined with human constant region domains to produce a chimeric antibody designated C2B8 which is marketed as RITUXAN™ in the U.S.A. or MABTHERA® (rituximab) in Europe. C2B8 is recognized as a valuable therapeutic agent for the treatment of NHL and other B-cell diseases (Maloney, D. G. et al. (1997) *J. Clin. Oncol.* 15: 3266-3274; Maloney, D. G. et al. (1997) *Blood* 90: 2188-2195).

An additional example of an anti-CD20 therapeutic is provided by the antibody B1, described in U.S. Pat. No. 6,090,365, the disclosure of which is incorporated herein by reference. This antibody has similarly achieved registration for use as a NHL therapeutic although in this case the molecule (BEXXAR™) is a $^{131}$I radioimmunoconjugate. The native B1 (non-conjugated) antibody has utility in ex vivo purging regimens for autologous bone marrow transplantation therapies for lymphoma and refractory leukaemia (Freedman, A. S. et al. (1990), *J. Clin. Oncol.* 8: 784).

Despite the success of antibodies such as C2B8 (rituximab) and BEXXAR™ there is a continued need for anti-CD20 analogues with enhanced properties. There is a particular need for enhancement of the in vivo characteristics when administered to the human subject. In this regard, it is highly desired to provide anti-CD20 antibodies with reduced or absent potential to induce an immune response in the human subject. Such proteins would display an increased circulation time within the human subject and would be of particular benefit in chronic use settings such as is the case for the therapeutic use of anti-CD20 molecules. The present invention provides modified anti-CD20 antibodies that display a relatively low level of immunogenicity in vivo.

SUMMARY OF THE INVENTION

The present invention provides polypeptide compositions that bind to CD20 antigen, preferably human CD20 antigen. The CD20 compositions comprise one or more anti-CD20 heavy chain and/or light chain variable region polypeptide segment, which can be a polypeptide selected from the group consisting of a modified form of the heavy chain variable region (Vh) of anti-CD20 antibody 2B8, a modified form of the light chain variable region (Vk) of anti-CD20 antibody 2B8, a modified form of the heavy chain variable region (Vh) of anti-CD20 antibody Leu16, and a modified form of the light chain variable region (Vk) of anti-CD20 antibody Leu16. The modified Vh and Vk polypeptides differ from the native Vh or Vk regions of 2B8 and Leu16 by one or more amino acid residue substitution in the native amino acid residue sequence of the antibody Vh and/or Vk region. The amino acid residue substitution(s) in the Vh or Vk polypeptides afford a lower level of immunogenicity to the CD20 binding polypeptide composition of the invention relative to the immunogenicity of the Vh or Vk regions of the native 2B8 and Leu16 antibodies.

A CD20-binding polypeptide composition of the invention comprises at least one polypeptide segment selected from the group consisting of a polypeptide having the amino acid residue sequence of SEQ ID NO: 48, which includes at least one amino acid residue substitution selected from the group consisting of $V_{12}K$, $A_{14}P$, $M_{20}V$, $I_{48}T$, $A_{68}T$, $Q_{82}E$, $T_{87}R$, $S_{91}T$, and $T_{106}W$; a polypeptide having the amino acid residue sequence of SEQ ID NO: 49, which includes at least one amino acid residue substitution selected from the group consisting of $L_{11}I$, $S_{12}T$, $S_{27}T$, $V_{29}A$, $G_{40}T$, $V_{59}S$, $S_{69}T$, $L_{72}M$, $R_{76}S$, and $V_{77}L$; a polypeptide having the amino acid residue sequence of SEQ ID NO: 50, which includes at least one amino acid residue substitution selected from the group consisting of $V_{12}K$, $M_{20}V$, $A_{68}T$, $Q_{82}E$, $T_{87}R$, $S_{91}T$, $D_{93}V$, and $A_{114}T$; and a polypeptide having the amino acid residue sequence of SEQ ID NO: 51, which includes at least one amino acid residue substitution selected from the group consisting of $L_{11}I$, $S_{12}T$, $A_{39}S$, $S_{69}T$, $L_{72}M$, $R_{76}S$, and $V_{77}L$.

As used herein and in the appended claims, an amino acid residue substitution is designated by listing the single letter code for the native amino acid residue in the sequence, followed by the position number of that residue (subscripted), followed by the single letter code for the amino acid residue that replaces the native amino acid. Accordingly a substitution $L_{11}I$ in SEQ ID NO: 4 means that the Leucine residue (L) at position 11 in SEQ ID NO: 4 (numbered from the N-terminus) is replaced (i.e., substituted) by an isoleucine (I).

Preferably, the CD20-binding polypeptide compositions of the invention have a binding affinity for human CD20 antigen that is about equal to or greater than the human CD20 binding affinity of monoclonal antibodies 2B8 or Leu16.

Preferred embodiments of the present invention comprise polypeptide segments such as a monoclonal antibody V-region heavy chain, termed herein "VhC", comprising the amino acid residue sequence of SEQ ID NO: 2: QVQLQQP-GAELKKPGASVKVSCKASGYTFTSYNMH-WVKQTPGRGLEWTGAIYPG NGDTSYNQKFKGKT-FLTADKSSSTAYMELSSLRSEDTAVYYCARSTYYGGD WYF NVWGAGTTVTVSA; a monoclonal antibody V-region heavy chain, termed herein "VhD", comprising the amino acid residue sequence of SEQ ID NO: 3: QVQLQQP-GAELKKPGASVKVSCKASGYTFTSYNMH-WVKQTPGRGLEWIGAIYPG NGDTSYNQKFKGKTTL-TADKSSSTAYMELSSLRSEDTAVYYCARSTYYGGDW YF NVWGAGTTVTVSA; and a monoclonal antibody V-region heavy chain, termed herein "VhY", comprising the amino acid residue sequence of SEQ ID NO: 10: EVQLQQS-GAELKKPGASVKVSCKASGYTFTSYNMH-WVKQTPGQGLEWIGAIYPG NGDTSYNQKFKGKTTL-TADKSSSTAYMELSSLRSEDTAVYYCARSNYYGSSYW FF DVWGTGTTVTSS.

Other preferred embodiments of the present invention comprise polypeptide segments such as a monoclonal antibody V-region light chain, termed herein "VkA", comprising the amino acid residue sequence of SEQ ID NO: 5: QIVLSQ-SPAIITASPGEKVTMTCRASTSASYIHW-FQQKPTSSPKPWIYATSNLASGVP SRFSGSGSGT-TYSMTISSLEAEDAATYYCQQWTSNPPTFGGGTKLEI K; a monoclonal antibody V-region light chain, termed herein "VkB", comprising the amino acid residue sequence of SEQ ID NO: 6: QIVLSQSPAIITASPGEKVTMTCRASTS-VSYIHWFQQKPTSSPKPWIYATSNLASGVP SRF-SGSGSGTIYSMTISSLEAEDAATYYC-QQWTSNPPTFGGGTKLEIK; a monoclonal antibody V-region light chain, termed herein "VkC", comprising the amino acid residue sequence of SEQ ID NO: 7: QIVLSQSPAIITASPGEKVTMTCRASTS-VSYIHWFQQKPGSSPKPWIYATSNLASGV PSRF-SGSGSGTTYSMTISSLEAEDAATYYC-QQWTSNPPTFGGGTKLEIK; a monoclonal antibody V-region light chain, termed herein "VkD", comprising the amino acid residue sequence of SEQ ID NO: 8: QIVLSQSPAIITASPGEKVTMTCRASSS-VSYIHWFQQKPGSSPKPWIYATSNLASGV PSRF-SGSGSGTTYSMTISSLEAEDAATYYC- QQWTSNPPTFGGGTKLEIK; and a monoclonal antibody V-region light chain, termed herein "VkZ", comprising the amino acid residue sequence of SEQ ID NO: 12: DIVLTQSPAIITASPGEKVTMTCRASSS-VNYMDWYQKKPGSSPKPWIYATSNLASG VPSRF-SGSGSGTTYSMTISSLEAEDAATYYC-QQWSFNPPTFGGGTKLEIK.

The present invention provides polypeptide compositions having therapeutic potential for the treatment of CD20-positive (CD20+) B-cell-associated diseases in man. The CD20-binding polypeptide compositions of the invention can be in the form of intact antibodies, Fab fragments, or fusion proteins comprising whole antibodies and cytokines, fusion proteins of antibody fragments and cytokines, or other any other form that binds to CD20 antigen.

The CD20-binding polypeptide compositions of the invention preferably include a combination of a heavy chain (Vh) anti-CD20 antibody variable region and a light chain (Vk) anti-CD20 antibody variable region, which bind to CD20 antigen. The Vh/Vk combinations can be configured as intact antibodies, Fab fragments, or fusion proteins comprising whole antibodies and cytokines, fusion proteins of antibody fragments and cytokines, or other any other configuration that binds to CD20 antigen. In other preferred embodiments, the V-regions are attached to each other through a polypeptide backbone.

Preferably, the CD20-binding polypeptide compositions of the invention include Vh and Vk polypeptides configured as an intact antibody, which includes a light chain constant region, and heavy chain CH1, CH2, and CH3 domains. Alternatively, the Vh and/or Vk polypeptides can be configured into a Fab fragment or a "minibody" having a CH3 domain but lacking a CH2 domain (see e.g., Wu et al., U.S. Pat. No. 5,837,821). Alternatively, the Vh and Vk polypeptides can be attached to each other through a linker to form an "single-chain Fv" antibody molecule. In one set of preferred embodiments, human constant regions are combined with the CD-20-binding Vh and Vk polypeptides. Such constant regions include those derived from IgA, IgD, IgM, IgE, or IgG1, IgG2, IgG3, or IgG4-type immunoglobulins. When a CH2 domain is included in the CD20-binding polypeptide composition, it is preferable to include a human IgG domain, such as an IgG1 CH2 domain. Other preferred embodiments lack the N-linked oligosaccharide glycosylation site found in the IgG CH2 domain. The absence of the N-linked glycosylation site is preferably engineered by mutation of the relevant asparagine, serine or threonine, or adjacent amino acids, or to treat the CH2-containing protein with an enzyme such as PNGase F to remove the oligosaccharide.

Preferred combinations of Vh and Vk regions include a polypeptide composition comprising the heavy chain V-region VhC (SEQ ID NO: 2) and a the light chain VkA (SEQ ID NO: 5); a polypeptide composition comprising the heavy chain V-region VhC (SEQ ID NO: 2) and a the light chain V-region VkB (SEQ ID NO: 6); a polypeptide composition comprising the heavy chain V-region VhC (SEQ ID NO: 2) and a the light chain V-region VkC (SEQ ID NO: 7); a polypeptide composition comprising the heavy chain V-region VhC (SEQ ID NO: 2) and a the light chain V-region VkD (SEQ ID NO: 8); a polypeptide composition comprising the heavy chain V-region VhD (SEQ ID NO: 3) and a the light chain V-region VkB (SEQ ID NO: 6); a polypeptide composition comprising the heavy chain V-region VhD (SEQ ID NO: 3) and a the light chain V-region VkD (SEQ ID NO: 8); and a polypeptide composition comprising the heavy chain V-region VhY (SEQ ID NO: 10) and a the light chain V-region VkZ (SEQ ID NO: 12).

One preferred polypeptide composition of the invention includes a V-region heavy chain of antibody 2B8 that includes one or more amino acid residue substitutions and has the amino acid sequence of SEQ ID NO: 48, which includes at least one amino acid residue substitution selected from the group consisting of $V_{12}K$, $A_{14}P$, $M_{20}V$, $I_{48}T$, $A_{68}T$, $Q_{82}E$, $T_{87}R$, $S_{91}T$, and $T_{106}W$. Another preferred polypeptide composition comprises a V-region light chain of antibody 2B8 (SEQ ID NO: 4) modified to contain one or more amino acid residue substitutions and which has the amino acid sequence of SEQ ID NO: 49, which includes at least one amino acid residue substitution selected from the group consisting of $L_{11}I$, $S_{12}T$, $S_{27}T$, $V_{29}A$, $G_{40}T$, $V_{59}S$, $S_{69}T$, $L_{72}M$, $R_{76}S$, and $V_{77}L$. FIG. 16 illustrates the location of the preferred amino acid residue substitutions in bold face type.

Another preferred CD20-binding polypeptide composition of the invention includes a V-region heavy chain (Vh) of antibody Leu16 (SEQ ID NO: 9) modified to contain one or more substitutions and which has the amino acid sequence of SEQ ID NO: 50, which includes one or more amino acid substitutions selected from the group consisting of $V_{12}K$, $M_{20}V$, $A_{68}T$, $Q_{82}E$, $T_{87}R$, $S_{91}T$, $D_{93}V$, and $A_{114}T$. Yet another preferred polypeptide composition of the invention includes a V-region light chain (Vk) of antibody Leu16 (SEQ ID NO: 11) modified to contain one or more amino acid residue substitutions and which has the amino acid sequence of SEQ ID NO: 51, which includes one or more amino acid substitutions selected from the group consisting of $L_{11}I$, $S_{12}T$, $A_{59}S$, $S_{69}T$, $L_{72}M$, $R_{76}S$, and $V_{77}L$. FIG. 16 illustrates the location of the preferred amino acid residue substitutions in bold face type.

The CD20-binding polypeptide compositions of the invention also include compositions having one or more anti-CD20 antibody heavy chain V-region that comprises a polypeptide segment selected from the group consisting of SGAELKKP-GAS (SEQ ID NO: 15), VSCKASGYT (SEQ ID NO: 16), LEWTGAIY (SEQ ID NO: 17), YNQKFKGKT (SEQ ID NO: 18), FKGKTTLTA (SEQ ID NO: 19), YMELSSLRS (SEQ ID NO: 20), SSLRSEDTAV (SEQ ID NO: 21), and DWGTGTTVT (SEQ ID NO: 22). Similarly, the CD20-binding polypeptide compositions of the invention also include compositions having one or more anti-CD20 antibody light chain V-region that comprises a polypeptide segment selected from the group consisting of IITASPGEKV (SEQ ID NO: 23), CRASTSASY (SEQ ID NO: 24), QQKPTSSP (SEQ ID NO: 25), LASGVPSRF (SEQ ID NO: 26), FSGSGSGTT (SEQ ID NO: 27), and YSMTISSLE (SEQ ID NO: 28). The V-region heavy chains and light chains can be configured, for example, as intact antibodies, antibody fragments, fusion proteins of an antibody with a cytokine, antibody fragment-cytokine fusion proteins, Fab molecules, single-chain Fv molecules, and minibodies. Preferably, the CD20-binding compositions are configured as intact antibodies, more preferably antibodies having human constant regions with and IgG heavy chain constant region isotype, most preferably including an IgG1 heavy chain constant region and having intact effector functions such as antibody-dependent, cell-mediated cytotoxicity.

In another preferred embodiment, the CD20-binding polypeptide composition is configured as an antibody-cytokine fusion protein, preferably including human constant regions with the isotype IgG1 and having intact effector functions such as antibody-dependent, cell-mediated cytotoxicity. In such preferred antibody-cytokine fusion proteins, it is useful to include an interleukin such as interleukin-2 (IL-2), IL-4, IL-5, IL-6, IL-7, IL-10, IL-12, IL-13, IL-14, IL-15, IL-16 and IL-18, a hematopoietic factor such as granulocytemacrophage colony stimulating factor (GM-CSF), granulocyte colony stimulating factor (G-CSF), erythropoeitin, a tumor necrosis factors (TNF) such as TNFα, a lymphokine such as lymphotoxin, a regulator of metabolic processes such as leptin, an interferon such as interferon α, interferon β, and interferon γ, or a chemokine. Preferably, the antibody-cytokine fusion protein of the present invention displays cytokine biological activity (e.g., stimulation of immune cells, such as T-cells or B-cells).

The polypeptide compositions of the present invention have a number of useful biological properties, including the ability to bind human B-cells; the ability to bind to CD20 antigen; a reduced ability to elicit an immune response in a human patient relative to antibodies Leu16 or 2B8 and related antibodies such as 1H4; and activity against B cell proliferative disorders such as leukemias, lymphomas, rheumatoid arthritis, and other autoimmune diseases. Diagnostic uses for the CD2-binding polypeptide compositions of the present invention are also contemplated. The diagnostic composition utilizing the CD20-binding moiety can be a full length antibody, an antibody fragment (e.g. F(ab')$_2$), a radiolabelled antibody, an immobilized antibody, or an antibody conjugated with a heterologous compound in an appropriate carrier vehicle. Such diagnostic compositions can be used to detect the presence of CD20-presenting cells, to purify or separate CD2—presenting cells, and the like.

The invention also provides pharmaceutical compositions comprising a CD20-binding composition as defined hereinabove together with a pharmaceutically acceptable carrier, diluent or excipient, as well as method of producing the polypeptide compositions.

BRIEF DESCRIPTION OF THE DRAWINGS

FIG. 1 shows the native amino acid residue sequence, in single letter code, of the V-region heavy chain protein of the 2B8 antibody and the modified amino acid residue sequences VhC and VhD based on the native sequence.

FIG. 2 shows the native amino acid residue sequence, in single letter code, of the V-region light chain protein of the 2B8 antibody and modified sequences VkA, VkB, VkC and VkD based on the native sequence.

FIG. 3 shows the amino acid residue sequence, in single letter code, of the heavy chain variable regions of Leu16Vh and a modified Leu16Vh region designated VhY;

FIG. 4 shows the amino acid residue sequence, in a single letter code, of the light chain variable regions of Leu16Vk and a modified Leu16Vk designated VhZ.

Treatments included PBS only (crossed Xs, on Days 7-11); rituximab (filled circles, 25 mg/kg on Days 7, 9 and 11); high dose Leu16VhY/VkZ-IL2 (anti-CD20 PC2) (large squares, 1 mg/kg on Days 7-11); low dose Leu16VhY/VkZ-IL2 (small squares, 0.25 mg/kg on Days 7-11); high dose chLeu16-IL2 (large triangles, 1 mg/kg on Days 7-11); and low dose chLeu16-IL2 (small triangles, 0.25 mg/kg on Days 7-11).

Figure 12:
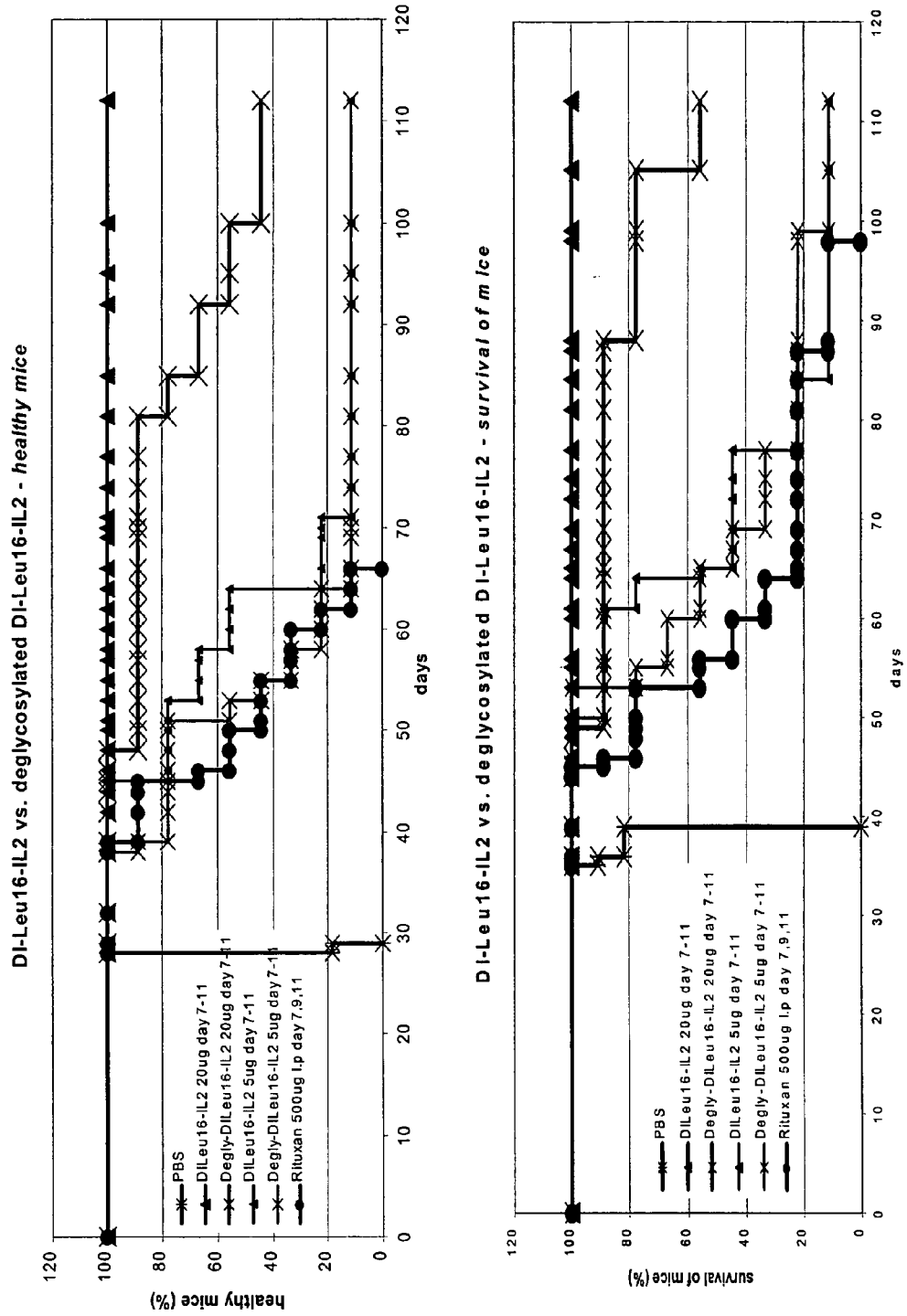

FIG. 12 illustrates that loss of ADCC activity has only a partial effect on anti-tumor activity mediated by Leu16VhY/VKZ-IL2 (anti-CD20 PC2). Two different doses of glycosylated (anti-CD20 PC2) and enzymatically deglycosylated Leu16VhY/VkZ-IL2 (anti-CD20 PC3) were used to treat SCID mice beginning 7 days after injection of Daudi lymphoma cells, as described for FIG. 9. Treatments included PBS only (X, on Days 7-11); rituximab (filled circles, 25 mg/kg on Days 7, 9 and 11); high dose Leu16VhY/VkZ-IL2 (large triangles, 1 mg/kg on Days 7-11); low dose Leu16VhY/VkZ-IL2 (small triangles, 0.25 mg/kg on Days 7-11); high dose deglycosylated Leu16VhY/VkZ-IL2 (large Xs with thick lines, 1 mg/kg on Days 7-11); and low dose deglycosylated Leu16VhY/VkZ-IL2 (small Xs with thin lines, 0.25 mg/kg on Days 7-11).

Figure 13:
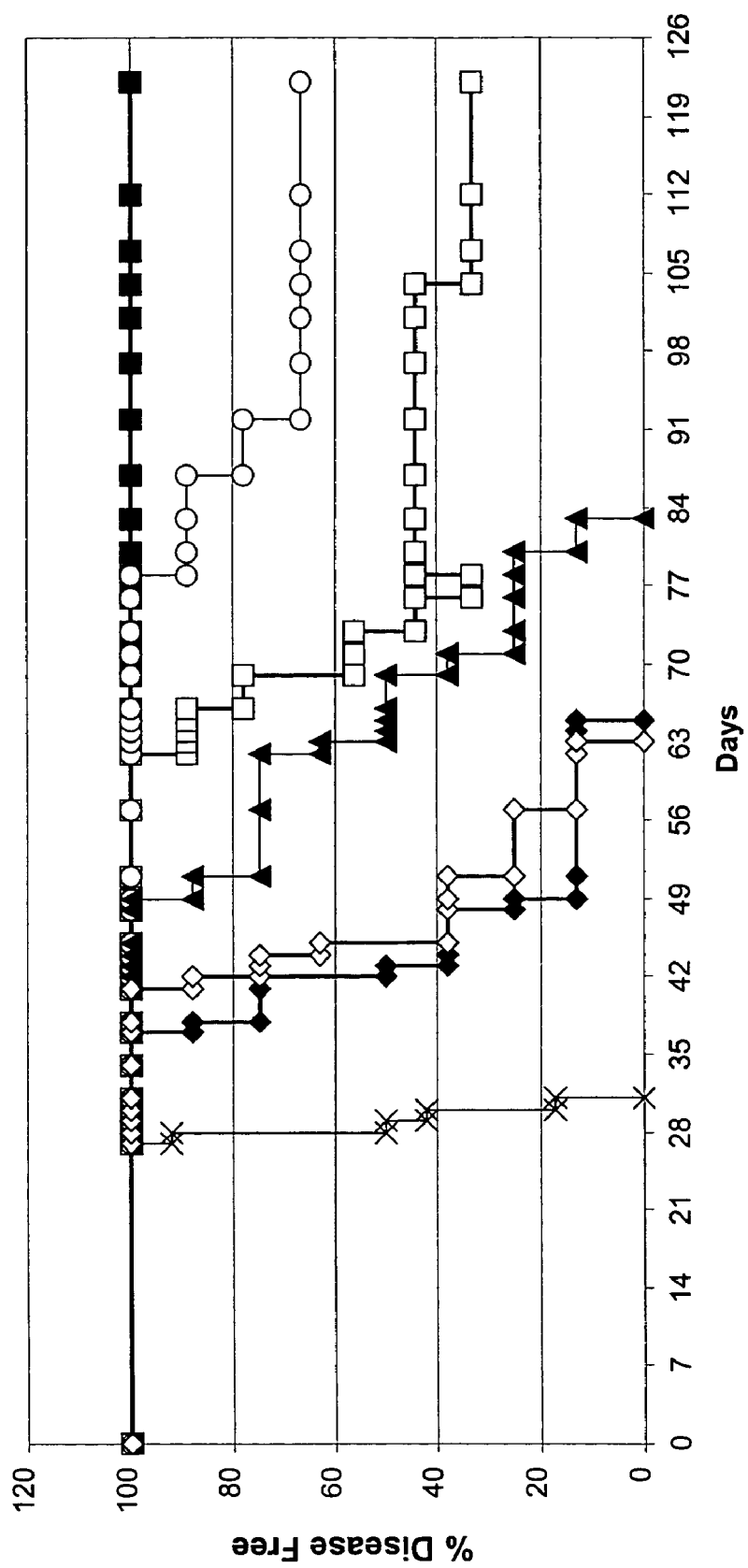

FIG. 13 illustrates that antigen specificity is important for optimal anti-tumor activity. The role of tumor cell targeting was tested by comparing the activity of Leu16VhY/VkZ-IL2 (DI-Leu16-IL2) and another immunocytokine with binding specificity for EGFR, a molecule expressed at only low levels of Daudi lymphoma cells. Treatments included PBS only (X, on Days 7-11); rituximab (filled diamonds, 25 mg/kg on Days 7, 9 and 11); Leu16VhY/VkZ (DI-Leu16 antibody; open diamonds, 25 mg/kg on Days 7, 9 and 11); medium dose Leu16VhY/VkZ-IL2 (DI-Leu16-IL2; filled squares, 1 mg/kg on Days 7-11); reduced dose Leu16VhY/VkZ-IL2 (DI-Leu16-IL2, open circle, 1 mg/kg on Days 7 and 10); low dose Leu16VhY/VkZ-IL2 (DI-Leu16-IL2; open squares, 0.25 mg/kg on Days 7-11); and medium dose anti-EGFR-IL2 (filled triangle, 1 mg/kg on Days 7-11). Results were scored as disease free survival.

Figure 14:
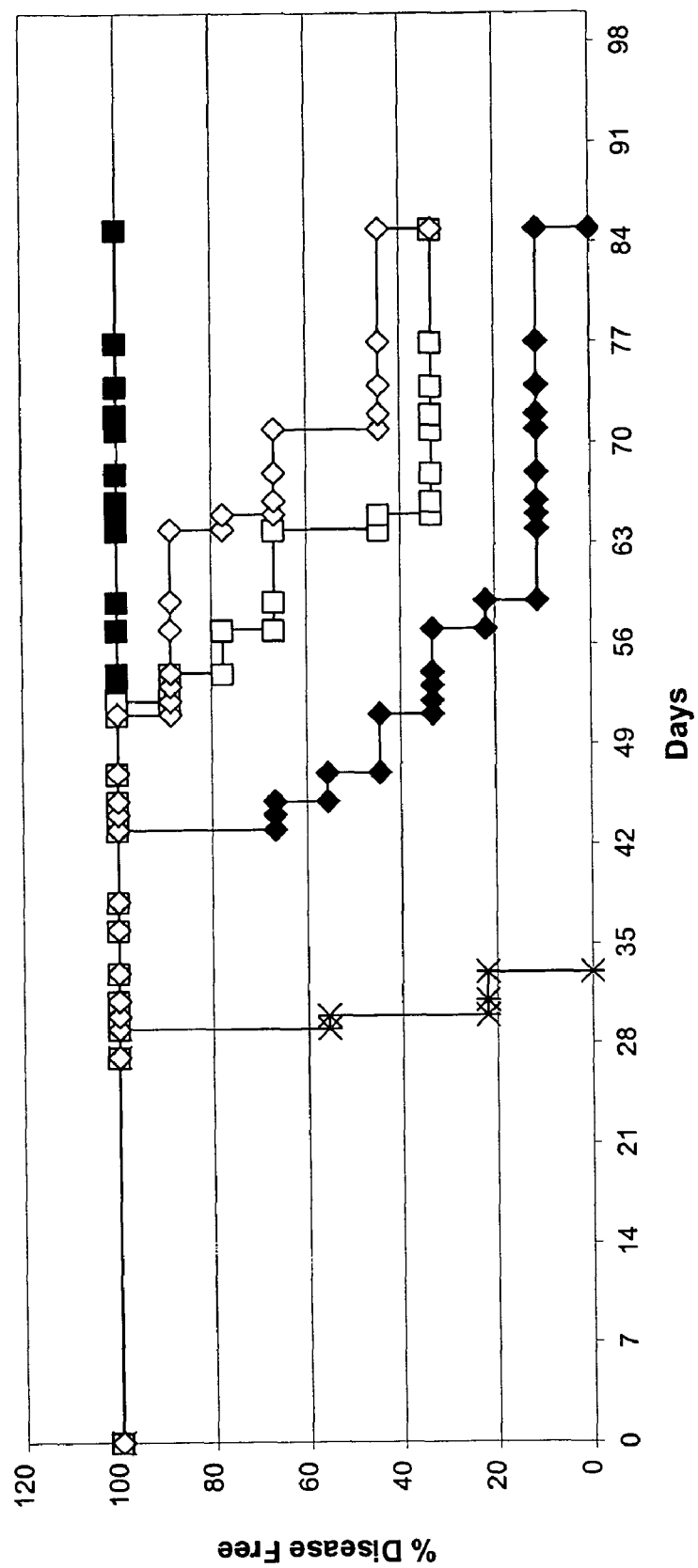

FIG. 14 illustrates that Leu16VhY/VkZ-IL2 ((anti-CD20 PC2) is more potent than higher doses of anti-CD20 antibody (anti-CD20 PC 1) combined with free IL-2. Anti-tumor activities of medium dose Leu16VhY/VkZ-IL2 (filled squares, 20 mg/mouse on Days 7-11) and the corresponding doses of the individual antibody and IL-2 components (open squares, 16.7 mg Leu16VhY/VKZ (anti-CD20 PC1) and 3.3 mg IL-2 by i.v. on Days 7-11) were compared to high dose rituximab and subcutaneous (s.c.) IL-2 (open diamonds, 500 mg rituximab on Days 7 and 10 mg IL-2 on Days 7, 9 and 11), rituximab alone (filled diamond, 500 mg on Day 7) or PBS control (X's).

Figure 15:
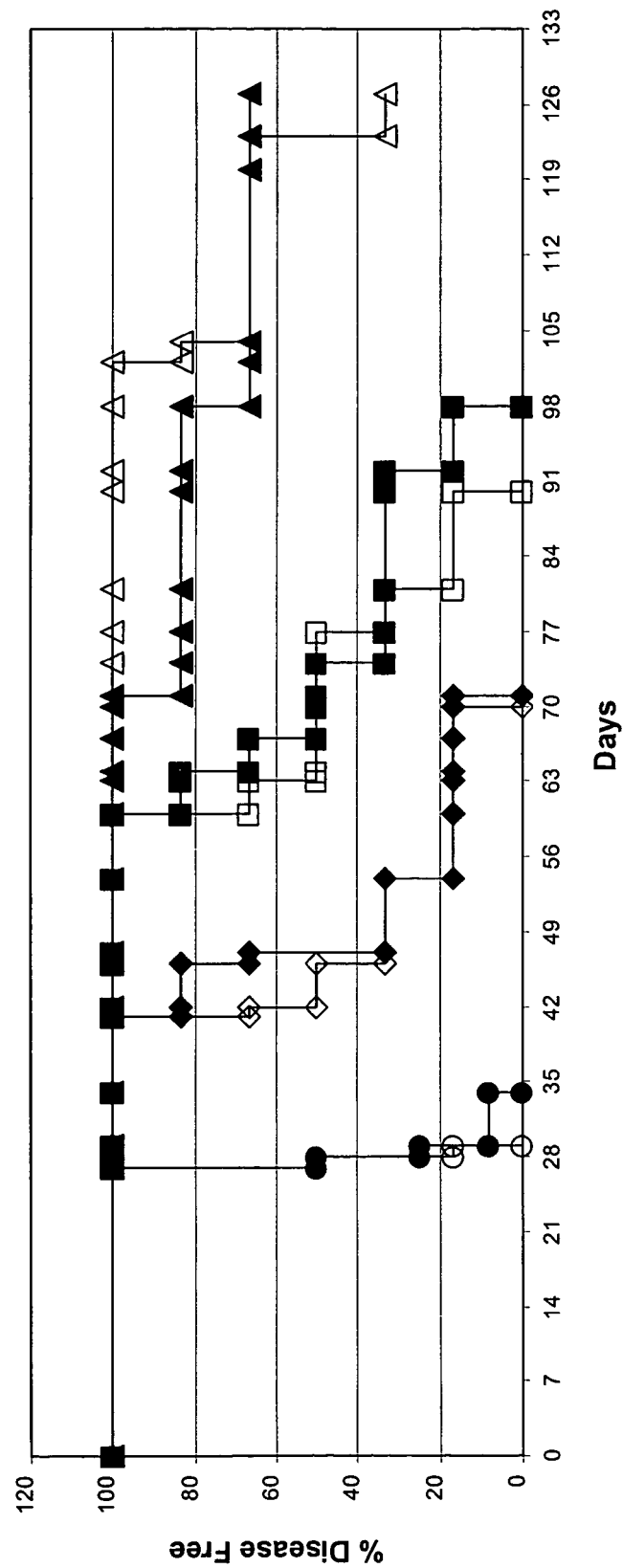

FIG. 15 illustrates that the presence of normal anti-CD20+B cells does not diminish the anti-tumor activity of Leu16VhY/VkZ-IL2 (anti-CD20 PC2). The effect of prior implantation of normal human CD20+ B cells was tested in the same SCID/Daudi lymphoma model as described. Groups of mice were treated with a single high dose of rituximab (diamonds, 25 mg/kg on Day 7), Leu16VhY/VkZ-IL2 (squares, 1 mg/kg on Days 11-15), the combination of both dosing regimens (triangles, rituximab on Day 7 followed by Leu16VhY/VkZ-IL2 on Days 11-15) or PBS alone on all dosing days. Half of the groups were injected i.v. with 4.5× $10^6$ PBMC on Day 5 (open symbols) or received only PBS (filled symbols). B cell engraftment was confirmed by measuring human antibody levels in the serum of all mice.

FIG. 16 shows an alignment of the heavy chain and light chain V-regions of the anti-CD20 antibodies 2B8, Leu16, and 1H4, as well as the epitope-depleted derivative V-regions of 2B8 (VhC, VhD, VkA, VkB, VkC, and VkD, and the epitope-depleted Leu16 V-regions VhY and VkZ.

FIG. 17 depicts all of the amino acid residue sequences and DNA sequences referred to in the specification of this application.

DETAILED DESCRIPTION OF PREFERRED EMBODIMENTS

As used herein an in the appended claims, the term "polypeptide composition" and grammatical variations thereof refers to a single chain polypeptide, as well as a multiple chain polypeptide in which the polypeptide chains are chemically bound to each other, such as by one or more disulfide bonds between a cysteine residue in one chain and a cysteine residue on another chain, by an ester bond, an amide bond, or any other suitable linkage. CD20-binding polypeptide compositions include one of more polypeptide chain having a binding affinity for the CD20 antigen, preferably human CD20 antigen. CD20-binding polypeptide compositions of the invention include one or more CD20-binding polypeptide chains having a reduced number of human T cell epitopes as compared to the native heavy chain variable region (Vh) and/or the native light chain variable region (Vk) of murine monoclonal antibodies 2B8 and Leu16, per se, as well as these polypeptides in a suitable carrier vehicle, which can be a liquid or a solid.

Reference to "substantially non-immunogenic" or "reduced immunogenic potential," as used herein and in the appended claims, means reduced immunogenicity compared to a counterpart or "parent" antibody, i.e. a non-modified murine or chimeric monoclonal antibody such as 2B8 or Leu16. The term "immunogenicity" means an ability to provoke, induce or otherwise facilitate a humoral and or T-cell mediated response in a host animal and in particular where the "host animal" is a human.

The term "antibody molecule" refers to a polypeptide of the immunoglobulin family, including a whole antibody, that is capable of combining, interacting or otherwise associating with an antigen. The term "antigen" is used herein to refer to a substance that is capable of interacting with the antibody molecule and in the context of the present invention is meant to be CD20. The CD20 of the present invention is human CD20 or any CD20 representing an antigen for antibody 2B8. The CD20 may be a soluble CD20 derivative or membrane associated CD20.

The term "immunoglobulin" is used herein to refer to a protein consisting of one or more polypeptides substantially encoded by immunoglobulin genes. The recognized immunoglobulin genes include the κ, λ, α, γ (IgG1, IgG2, IgG3, IgG4), σ, ε, and μ constant region genes and in nature multiple immunoglobulin variable region genes. One natural form of immunoglobulin is a tetramer comprising two identical pairs in which each pair has one light chain and one heavy chain. In each pair the heavy and light chain variable regions together provide the binding surface capable of interacting with the antigen. The term Vh is used herein to refer to the heavy chain variable region, and the term Vk is used herein to refer to the light chain variable region and in this instance in common with numerous monoclonal antibodies the light chain is a "kappa" (k) type chain.

The V-region includes amino acid residues from a "complementarity determining region" or "CDR" (i.e. at about amino acid residues 24-34 (L1), 50-56 (L2) and 89-97 (L3) in the light chain variable domain and at about amino acid residues 31-35 (H1), 50-65 (H2) and 95-102 (H3) in the heavy chain variable domain as defined by Kabat et al. (Kabat et al. *Sequences of Proteins of Immunological Interest*, 5th Ed. Public Health Service, National Institutes of Health, Bethesda, Md. (1991)). Alternative definitions of the CDRs are also recognized in the art for example according to the scheme of Chothia (Chothia and Lesk (1987) *J. Mol. Biol.* 196: 901-917) in which case the CDRs are found at about amino acid residues 26-32 (L1), 50-52 (L2) and 91-96 (L3) in the light chain, and at about amino acid residues 26-32 (H1), 53-55 (H2) and 96-101 (H3) in the heavy chain. "Framework" or "FR" residues are those V-region residues other than the CDR residues as herein defined.

As used herein, Vh includes a polypeptide that is about 110 to 125 amino acid residues in length, the sequence of which corresponds to any of the specified Vh chains herein which in combination with a Vk are capable of binding human CD20. Similarly, Vk includes a polypeptide that is about 95-130 amino acid residues in length, the sequence of which corresponds to any of the specified Vk chains herein which in combination with a Vh are capable of binding human CD20. Full-length immunoglobulin heavy chains are about 50 kDa molecular weight and are encoded by a Vh gene at the N-terminus and one of the constant region genes (e.g. γ) at the C-terminus. Similarly, full-length light chains are about 25 kDa molecular weight and are encoded by a V-region gene at the N-terminus and a κ or γ constant region gene at the C-terminus.

In addition to a whole antibody (a tetramer), immunoglobulins may exist in a number of other forms produced by application of recombinant DNA techniques or protein biochemistry. These forms include for example Fv, Fab, Fab' and F(ab')$_2$ molecules and could all contain any of the Vh or Vk sequences of the present invention. An additional example is a "bi-specific" antibody, that is comprising a Vh/Vk combination of the present invention in combination with a second Vh/Vk combination with a different antigen specificity.

The term "T-cell epitope," as used herein and in the appended claims, means an amino acid sequence which is able to bind MHC Class II, able to stimulate T-cells and/or also to bind (without necessarily measurably activating) T-cells in complex with MHC Class II.

The term "peptide" as used herein and in the appended claims, is a compound that includes two or more amino acid residues. The amino acid residues are linked together by a peptide bond (defined herein below). There are 20 different common, naturally occurring amino acids involved in the biological production of peptides, and any number of them may be linked in any order to form a peptide chain or ring. The naturally occurring amino acids employed in the biological production of peptides all have the L-configuration. Synthetic peptides can also be prepared employing conventional synthetic methods, utilizing L-amino acids as well as D-amino acids, or various combinations of amino acids of the two different configurations. Some peptides contain only a few amino acid residues. Short peptides, e.g., having less than ten amino acid residues, are sometimes referred to as "oligopeptides". Other peptides contain a large number of amino acid residues, e.g. up to 100 or more, and are referred to as "polypeptides". By convention, a "polypeptide" may be considered as any peptide chain containing three or more amino acid residues, whereas an "oligopeptide" is usually considered as a particular type of "short" polypeptide. Thus, as used herein, it is understood that any reference to a "polypeptide" herein also includes an oligopeptide. Further, any reference to a "peptide" includes polypeptides, oligopeptides, and proteins. Each different arrangement of amino acid residues forms different polypeptides or proteins. The number of polypeptides—and hence the number of different proteins—that can be formed is practically unlimited.

A CD20-binding polypeptide composition comprises at least one polypeptide segment selected from the group consisting of a modified heavy chain variable region polypeptide (Vh) having the amino acid residue sequence of SEQ ID NO: 48, which includes at least one amino acid residue substitution selected from the group consisting of $V_{12}K$, $A_{14}P$, $M_{20}V$, $I_{48}T$, $A_{68}T$, $Q_{82}E$, $T_{87}R$, $S_{91}T$, and $T_{106}W$; a modified light chain variable region polypeptide (Vk) having the amino acid residue sequence of SEQ ID NO: 49, which includes at least one amino acid residue substitution selected from the group consisting of $L_{11}I$, $S_{12}T$, $S_{27}T$, $V_{29}A$, $G_{40}T$, $V_{59}S$, $S_{69}T$, $L_{72}M$, $R_{76}S$, and $V_{77}L$; a modified Vh having the amino acid residue sequence of SEQ ID NO: 50, which includes at least one amino acid residue substitution selected from the group consisting of $V_{12}K$, $M_{20}V$, $A_{68}T$, $Q_{82}E$, $T_{87}R$, $S_{91}T$, $D_{93}V$, and $A_{114}T$; and a modified Vk having the amino acid residue sequence of SEQ ID NO: 51, which includes at least one amino acid residue substitution selected from the group consisting of $L_{11}I$, $S_{12}T$, $A_{59}S$, $S_{69}T$, $L_{72}M$, $R_{76}S$, and $V_{77}L$.

Preferably, a CD20-binding polypeptide composition of the invention is substantially free from T cell epitopes and includes a polypeptide having an amino acid residue sequence selected from the group consisting of SEQ ID NO: 15, SEQ ID NO: 16, SEQ ID NO: 17, SEQ ID NO: 18, SEQ ID NO: 19, SEQ ID NO: 20, SEQ ID NO: 21, SEQ ID NO: 22, SEQ ID NO: 23, SEQ ID NO: 24, SEQ ID NO: 25, SEQ ID NO: 26, SEQ ID NO: 27, SEQ ID NO: 28, and mixtures thereof.

In a preferred embodiment, the CD20-binding polypeptide composition includes a modified heavy chain variable region polypeptide and a modified light chain variable region polypeptide. More preferably, the CD20-binding polypeptide composition is in the form of a chimeric antibody and also includes a human heavy chain constant region, as well as a human light chain constant region. Preferably, the human heavy chain constant region is an IgG constant region, more preferably an IgG1 constant region. The human light chain constant region preferably is a human kappa light chain constant region.

Another preferred embodiment of the CD20-binding polypeptide composition of the invention is a fusion protein comprising a polypeptide composition including modified heavy chain or light chain variable region segment, as described above, fused with a cytokine. Preferably the cytokine is IL-2.

Another preferred embodiment of the CD20-binding polypeptide composition of the invention is an antibody molecule, such as a Fab antibody fragment, a single-chain Fv antibody fragment, or a minibody, which includes at least one modified Vh or modified Vk segment, as described above.

A particularly preferred CD20-binding polypeptide composition comprises at least one Vh polypeptide segment having an amino acid residue sequence selected from the group consisting of SEQ ID NO: 2, SEQ ID NO: 3 and SEQ ID NO: 10. Another particularly preferred CD20-binding polypeptide composition comprises at least one Vk polypeptide segment having an amino acid residue sequence selected from the group consisting of SEQ ID NO:5 SEQ ID NO: 6, SEQ ID NO: 7, SEQ ID NO: 8, and SEQ ID NO: 12. More preferably, the CD20-binding polypeptide composition comprises a Vh polypeptide segment having an amino acid residue sequence selected from the group consisting of SEQ ID NO: 2, SEQ ID NO: 3, and SEQ ID NO: 10; and a Vk polypeptide segment having an amino acid residue sequence selected from the group consisting of SEQ ID NO: 5, SEQ ID NO: 6, SEQ ID NO: 7, SEQ ID NO: 8, and SEQ ID NO: 12.

Other preferred CD20-binding polypeptide compositions of the present invention comprise combinations of modified Vh and modified Vk segments selected from the group consisting of (a) a Vh segment having an amino acid residue sequence of SEQ ID NO: 2 and a Vk segment having an amino acid residue sequence of SEQ ID NO: 5; (b) a Vh segment having an amino acid residue sequence of SEQ ID NO: 2 and a Vk segment having an amino acid residue sequence of SEQ ID NO: 6; (c) a Vh segment having an amino acid residue sequence of SEQ ID NO: 2 and a Vk segment having an amino acid residue sequence of SEQ ID NO: 7; (d) a Vh segment having an amino acid residue sequence of SEQ ID NO: 2 and a Vk segment having an amino acid residue sequence of SEQ ID NO: 8; (e) a Vh segment having an amino acid residue sequence of SEQ ID NO: 3 and a Vk segment having an amino acid residue sequence of SEQ ID NO: 6; (f) a Vh segment having an amino acid residue sequence of SEQ ID NO: 3 and a Vk segment having an amino acid residue sequence of SEQ ID NO: 8; and (g) a Vh segment having an amino acid residue sequence of SEQ ID NO: 10 and a Vk segment having an amino acid residue sequence of SEQ ID NO: 12.

Another aspect of the present invention is a pharmaceutical or diagnostic composition comprising a CD20-binding polypeptide composition of the invention, together with a pharmaceutically acceptable carrier, excipient, and/or diluent. The pharmaceutical composition can also include an additional pharmacologically effective drug.

The disclosed, modified Vh and Vk sequences were designed to have a reduced number of human T cell epitopes relative the native Vh and Vk regions of the anti-CD20 murine monoclonal antibodies 2B8 and Leu16 referred to herein as the "parental" or "counterpart" antibodies. The amino acid residue sequences of the modified Vh and Vk polypeptides were designed based on an analysis of the V-region amino acid residue sequences of the mouse monoclonal antibodies 2B8 and Leu16. These antibodies are disclosed fully in respect of their useful in vitro and in vivo properties in U.S. Pat. No. 5,736,137; U.S. Pat. No. 5,776,456; U.S. Pat. No. 6,399,061; U.S. Pat. No. 6,455,043 and foreign equivalents, and in Wu et al. (*Protein Engineering* (2001) 14:1025-1033) and references cited therein.

Sequence analysis was conducted to identify portions of the Vh and Vk peptides that can bind to a MHC Class II ligand and therefore, can function as a T-cell epitope in man. Identification of the positions of potential MHC Class II epitopes within a given peptide sequence is a first step of the engineering process. Epitope identification was conducted computationally, following the scheme outlined in detail in WO 02/069232, which is incorporated herein by reference.

Substitution of particular amino acid residues within a V-region heavy chain (Vh) or light chain (Vk) of the parental antibody results in a modified Vh or Vk polypeptide with a reduced number of MHC Class II ligands and accordingly, a reduced propensity for the polypeptide to act as a T-cell epitope in a human. At the same time, the amino acid residue substitutions provide polypeptides that retain structural and functional properties of the parental antibody Vh and Vk regions, including stable expression within a host cell and ability for the polypeptide to bind to human CD20 antigen, and especially the ability to bind to human B-cells in vitro.

The Vh and Vk amino acid residue sequences of 2B8 and Leu16, as well as the anti-CD20 antibody B 1, are quite similar, even though they are of independent origin. Not wishing to be bound by theory, it is notable that the sequence CEPANPSEKNSPSTQYC (SEQ ID NO: 29) in human CD20, which is part of the short extracellular peptide of CD20, and which is flanked by cysteines that are likely to form a disulfide bond, corresponds to the sequence CEPS NSSEKNSPSTQYC (SEQ ID NO: 38) in mouse CD20. The mouse NSS sequence (underlined in SEQ ID NO: 38, above) is likely to be an N-linked glycosylation site, while the corresponding NPS sequence (underlined in SEQ ID NO: 29, above) in humans is not likely to be an N-linked glycosylation site. This difference between the mouse and human CD20 sequences indicates the location of a human T cell epitope. Accordingly, it is likely that all of the mouse antibodies generated against human CD20 may be used to recognize a very narrowly defined epitope.

The present invention provides a set of reduced-immunogenicity consensus V-region sequences that are useful for recognition of human CD20. For example, a modified heavy chain variable region including the sequence segment VSCK-ASGYT (SEQ ID NO: 16) is a less immunogenic polypeptide than a polypeptide containing the corresponding sequence segment MSCKASGYT (SEQ ID NO: 30), from the native 2B8 and Leu16 antibodies. Similarly, modified heavy chain variable regions that include one or more of the modified sequences YNQKFKGKT (SEQ ID NO: 18), FKGKTTLTA (SEQ ID NO: 19), and YMELSSLRS (SEQ ID NO: 20) are less immunogenic than native heavy chain variable regions containing the corresponding sequences, YNQKFKGKA (SEQ ID NO: 31), FKGKATLTA (SEQ ID NO: 32), and YMQLSSLRS (SEQ ID NO: 33), which are found in the parental 2B8 and Leu16 antibodies.

A modified light chain variable region including the sequence IITASPGEKV (SEQ ID NO: 23) is less immunogenic than a light chain variable region containing the corresponding sequence ILSASPGEKV (SEQ ID NO: 34), from the parental 2B8 and Leu16 antibodies. Similarly, modified light chain variable regions including one or more of the sequences LASGVPSRF (SEQ ID NO: 26), FSGSGSGTT (SEQ ID NO: 27), and YSMTISSLE (SEQ ID NO: 28) are less immunogenic than light chain variable regions including the corresponding sequences, LASGVPVARF (SEQ ID NO: 35), FSGSGSGTS (SEQ ID NO: 36), and YSLTISRVE (SEQ ID NO: 37), which are found in the parental 2B8 and Leu16 antibodies.

For the elimination of T-cell epitopes, amino acid substitutions are made at appropriate points within the peptide sequence predicted to achieve substantial reduction or elimination of the activity of the T-cell epitope. In practice an appropriate point will preferably equate to an amino acid residue binding within one of the pockets provided within the MHC Class II binding groove.

It is most preferred to alter binding within the first pocket of the cleft at the so-called P1 or "P1 anchor" position of the peptide. The quality of binding interaction between the P1 anchor residue of the peptide and the first pocket of the MHC Class II binding groove is recognized as being a major determinant of overall binding affinity for the whole peptide. An appropriate substitution at this position of the peptide is for a residue less readily accommodated within the pocket, for example, substitution to a more hydrophilic residue. Amino acid residues in the peptide at positions equating to binding within other pocket regions within the MHC binding cleft are also considered and fall under the scope of the present invention.

A single amino acid substitution within a given potential T cell epitope is the most preferred route by which the epitope may be eliminated. Combinations of substitution within a single epitope may be contemplated, and for example, can be particularly appropriate where individually defined epitopes are in overlap with each other. Moreover, amino acid substitutions either singly within a given epitope, or in combination within a single epitope, may be made at positions not equating to the "pocket residues" with respect to the MHC Class II binding groove, but at any point within the peptide sequence. All such substitutions fall within the scope of the present.

A significant feature of the CD20-binding polypeptide compositions of the invention, such as modified anti-CD20 antibody molecules, is that they retain the functional activities of the non-modified parental antibody. It is therefore particularly desired to produce modified antibodies, modified antibody molecules, and other CD20-binding polypeptide compositions in which substantially all of the beneficial technical features associated with the therapeutic efficacy of the parental non-modified antibody are exhibited. This is pertinent to the contemplated utility of the invention, namely to provide a composition with therapeutic efficacy in a number of important diseases in man including especially B-cell lymphoma and other B-cell mediated pathologies. Such therapeutic agents are preferred embodiments of the present invention.

Accordingly, the CD20-binding polypeptide compositions of the present invention exhibit an affinity for its target CD20 antigen that is similar to the affinity exhibited by the parental antibody. The polypeptide compositions therefore recognize CD20 positive human B-cells. The therapeutic efficacy of a parental antibody such as 2B8 and Leu16 is considered to be mediated by the ability of the antibody to induce antibody-dependent cellular cytotoxicity (ADCC). A significant feature of this activity is the ability of the antibody constant region (i.e. the Fc domain) to bind human serum complement component C1q. ADCC and C1q binding are both mediated by the constant region domain of whole antibody molecule. The present invention contemplates, in one aspect, production of whole antibody molecules comprising a human Fc region that is compatible with ADCC induction. Such constant regions are most preferably IgG1 heavy chains in combination with human kappa light (e.g. Km3) chains.

The present invention also provides antibody fragments of reduced immunogenicity, including for example, Fv, Fab, Fab' and F(ab')$_2$ fragments. Such fragments may be prepared by standard methods (see, for example; Coligan et al. (*Current Protocols in Immunology*, John Wiley & Sons 1991-1997). The present invention also provides various recombinant forms of antibody molecules. Such species include stabilised Fv fragments having single chain Fv forms (e.g. scFv) and comprising a peptide linker joining the Vh and Vk domains, as well as an Fv fragments stabilized by inter-chain disulfide linkage (dsFv), and which contain additional cysteine residues engineered to facilitate the conjoining of the Vh and Vk domains. Other compositions include species referred to as "minibodies"; and single variable domain "dAbs", as well as materials that incorporate structures that increase the valency of the modified antibody V-region domain, i.e. materials having multiple antigen binding sites, for example, by including dimerization domains (e.g. "leucine zippers") or other chemical modifications.

In yet another aspect, the invention relates to fusion proteins in which modified anti-CD20 V-regions are coupled to a non-immunoglobulin fusion partner protein, such as an anti-cancer protein. Examples of such proteins include toxins, such as *Pseudomonas* exotoxin; enzymes, such as bacterial proteases for antibody-dependent prodrug therapy ("ADEPT"), or most preferably, cytokines. Particularly useful cytokines are wild-type and mutant versions of IL-2, IL-12, fused forms of IL-2 and IL-12, and other interleukins, interferons, and tumor necrosis factors. Gillies and co-workers (U.S. Pat. No. 5,150,650, WO98/25978, WO01/10912, WO02/72605, WO03/48334), Epstein (WO 03/15697), and Halin et al. (*Cancer Res.* (2003) 63:3202-10, the disclosures of which are incorporated herein by reference, have described a number of configurations of anti-cancer antibody V-regions and cytokines. The immunoglobulin constant regions of fusion proteins comprising the V-regions of the present invention may be further modified by mutations, such as mutations affecting complement fixation, mutations affecting Fc receptor binding, mutations affecting FcRn binding, mutations affecting the serum half-life of the fusion protein and mutations removing potential T cell epitopes from the junction region of an Ig heavy chain fusion protein. Examples of such mutations are described in WO09943713, WO01/58957, WO02/079232, and WO02/079415, which are incorporated herein by reference.

For Ig fusion proteins it has been observed that alteration of amino acid residues near the junction of the Ig heavy chain constant region and the non-Ig fusion partner protein can dramatically increase the serum half-life of the Ig fusion protein (PCT publication WO 01/58957, the disclosure of which is hereby incorporated by reference). Accordingly, the junction region of an anti-CD20 Ig fusion protein of the present invention can contain alterations that, relative to the naturally-occurring sequences of an immunoglobulin heavy chain and the fusion partner protein (such as IL-2), preferably lie within about 10 amino acid residues of the junction point. These amino acid residue changes can increase hydrophobicity by, for example, changing the C-terminal lysine of the Ig heavy chain constant region to a hydrophobic amino acid residue such as alanine or leucine.

In other embodiments, the Ig heavy chain portion of the Ig fusion protein contains amino acid residue alterations of the Leu-Ser-Leu-Ser (SEQ ID NO: 46) segment near the C-terminus of the immunoglobulin heavy chain constant region. The amino acid residue substitutions of the Leu-Ser-Leu-Ser (SEQ ID NO: 46) segment eliminate potential junctional T-cell epitopes. In one particular embodiment, the Leu-Ser-Leu-Ser (SEQ ID NO: 46) amino acid residue sequence near the C-terminus of the Ig heavy chain portion is replaced with an Ala-Thr-Ala-Thr (SEQ ID NO: 47) amino acid residue sequence. In other embodiments, the amino acid residues within the Leu-Ser-Leu-Ser (SEQ ID NO: 46) segment are replaced with other amino acid residues such as glycine or proline. Detailed methods of generating amino acid substitutions of the Leu-Ser-Leu-Ser (SEQ ID NO: 46) segment near the C-terminus of an IgG1, IgG2, IgG3, IgG4, or other immunoglobulin class molecule have been described in U.S. patent application Ser. No. 10/112,582 (US 2003/0166877A1; now U.S. Pat. No. 6,992,174), the disclosure of which is incorporated herein by reference.

Yet another aspect the present invention relates to methods for therapeutic treatment of humans using the CD20-binding polypeptide compositions of the invention. The Examples illustrate how the polypeptide compositions of the invention have been used to treat human cancer cells in mouse models, and the results obtained below are generally illustrative of strategies that would be used to treat human cancers such as B cell lymphoma and other cancers expressing CD20.

The anti-CD20-IL2 fusion proteins of the invention, such as anti-CD20-IL2 fusion proteins, are used as follows: A patient suffering from a CD20-expressing cancer, such as B cell lymphoma, is administered a polypeptide composition of the invention. The preferred route of administration is intravenous or subcutaneous injection, but intramuscular, intraperitoneal, intradermal, or other routes of injection are also possible. Administration by inhalation, orally, or by suppositories is also possible, as are other routes of administration. Administration is preferably in a four-week cycle of three times per week, followed by no treatment for the next three weeks. Treatments can be more or less frequent depending on the pharmacokinetic behavior of the fusion protein in a given individual. The preferred dosage for an adult of about 70 kilograms is in the range of about 1 to about 100 milligrams per dose, with a preferred range of about 4 to about 20 milligrams per dose. The most preferred dose is about 10 milligrams for a 70 kg adult treated once per month. Patients are monitored for a response according to standard procedures.

In a further aspect, the present invention relates to isolated nucleic acids encoding CD20-binding polypeptide compositions, such as nucleic acids that encode a modified anti-CD20 antibody molecule, a modified heavy chain variable region polypeptide, a modified light chain variable region polypeptide, anti-CD20 antibody fusion proteins, and the like.

The DNA sequence of the polynucleotide encoding the light chain of Leu16 is shown in FIG. 17 (SEQ ID NO: 39). The DNA sequence encoding a preferred epitope-depleted version of the light chain of Leu16 (i.e., including Vkz and a human constant region) is shown in FIG. 17 as SEQ ID NO: 40. The DNA sequence of the polynucleotide encoding the heavy chain of Leu16 is shown in FIG. 17 (SEQ ID NO: 41). The DNA sequence encoding a preferred epitope-depleted version of the heavy chain of Leu16 (i.e., including VhY and a human constant region) is shown in FIG. 17 as SEQ ID NO: 42. The DNA sequence encoding a preferred epitope-depleted version of the heavy chain of Leu16 fused to IL-2 (i.e., including VhY, a human constant region, and IL-2 bound to the C-terminus of the constant region) is shown in FIG. 17 as SEQ ID NO: 43.

Yet another aspect the present invention relates to methods for therapeutic treatment of humans using the CD20-binding polypeptide compositions of the invention. The Examples illustrate how the polypeptide compositions of the invention have been used to treat human cancer cells in mouse models, and the results obtained below are generally illustrative of strategies that would be used to treat human cancers such as B cell lymphoma and other cancers expressing CD20.

The CD20-binding polypeptide compositions of the invention, such as anti-CD20-IL2 fusion proteins, are used as follows: A patient suffering from a CD20-expressing cancer, such as B cell lymphoma, is administered a polypeptide composition of the invention. The preferred route of administration is intravenous or subcutaneous injection, but intramuscular, intraperitoneal, intradermal, or other routes of injection are also possible. Administration by inhalation, orally, or by suppositories is also possible, as are other routes of administration. Administration is preferably in a four-week cycle of three times per week, followed by no treatment for the next three weeks. Treatments can be more or less frequent depending on the pharmacokinetic behavior of the fusion protein in a given individual. The preferred dosage for an adult of about 70 kilograms is in the range of about 1 to about 100 milligrams per dose, with a preferred range of about 4 to about 20 milligrams per dose. The most preferred dose is about 10 milligrams for a 70 kg adult treated once per month. Patients are monitored for a response according to standard procedures.

EXAMPLES

The following examples describe illustrative methods for making CD20-binding polypeptide compositions of the invention, such as antibodies and antibody-cytokine fusion proteins. Those skilled in the art of protein expression will recognize that a wide variety of well-known techniques may be used to make polypeptide compositions of the invention. For example, the polypeptide compositions of the invention are preferably made in eukaryotic cells such as mammalian cells, such as NS/0 cells, BHK cells, CHO cells, 293 cells, or PERC6 cells.

A CD20-binding polypeptide composition of the invention can be purified using some or all of the following steps, in sequence: Abx Mixed Resin column chromatography, recombinant Protein A chromatography, Q Sepharose column chromatography, hydrophobic interaction (HIC) column chromatography, and hydroxyapatite column chromatography, followed by Pellicon 2 tangential flow diafiltration for buffer exchange into formulation buffer. Virus inactivation and removal steps are interdigitated into these steps. The virus inactivation and removal steps are not necessary for purification, per se, but are used to satisfy regulatory considerations.

Example 1

Methods and Reagents for Expressing CD20-Binding Polypeptide Compositions which are "Deimmunised" or "Epitope-Deleted" Leu16 Antibodies 1A: Cell Culture and Transfection In order to obtain stably transfected clones, plasmid DNA was introduced into the mouse myeloma NS/0 cells by electroporation. About $5 \times 10^6$ cells were washed once and re-suspended with phosphate buffered saline solution (PBS). Ten µg of linearized plasmid DNA was then incubated with the cells in a Gene Pulser cuvette (0.4 cm electrode gap, BioRad) for 10 minutes on ice. Electroporation was performed using a Gene Pulser (BioRad) with settings at 0.25 V and 500 µF. Cells were allowed to recover for 10 minutes on ice, after which they were re-suspended in growth medium and then plated onto 96-well plates. Stably transfected clones were selected by growth in the presence of 100 nM methotrexate (MTX), which was introduced two days post-transfection. The cells were fed every 3 days for 2 or 3 more times and MTX-resistant clones appeared in 2 to 3 weeks. Supernatants from clones were assayed by anti-human Fc ELISA and analytical high-pressure liquid chromatography (HPLC), to identify high producers (Gillies et al. (1989) *J. Immunol. Methods* 125:191). High producing clones (yielding about 100 µg of purified protein per ml of cell culture supernatant in medium scale cell cultures) were isolated and propagated in growth medium containing 100 mM MTX.

The following CD20-binding polypeptide compositions of the invention were prepared to illustrate the invention: Anti-CD20 PC1 is a chimeric antibody having two human IgG1 heavy chain constant regions, two human kappa light chain constant regions, two modified heavy chain variable regions designated as "VhY" and two modified light chain variable regions designated as "VkZ" all assembled together into an antibody structure, in which the heavy chain constant regions are attached to the C-termini of the heavy chain variable regions and the light chain constant regions are attached to the C-termini of the light chain variable regions; each light chain is bound to a heavy chain by disulfide linkages to form two dimeric structures, which are bound to each other through disulfide linkages between the two heavy chains, as is well known in the art; Anti-CD20 PC2 is a fusion protein comprising an anti-CD20 PC1 derivative bound to IL-2 at the C-terminus of each heavy chain (the derivative includes the segment ATATPGA (SEQ ID NO: 44) near the C-terminus of the heavy chain in place of the segment LSLSPGK (SEQ ID NO:

45) found in anti-CD20-PC1); AntiCD20 PC1 and anti-CD20 PC2 are glycosylated in the same fashion as Leu16. Anti-CD20 PC3 is a deglycosylated version of anti-CD20 PC2.

1B: ELISAs

ELISAs were used to determine the concentrations of protein products in the supernatants of MTX-resistant clones. The anti-hufc ELISA was used to measure the amount of human Fc-containing proteins.

The anti hu-Fc ELISA is described in detail below.

A. Coating Plates. ELISA plates were coated with AFFINIPURE™ goat anti-human IgG (H+L) (Jackson Immuno Research) at 5 µg/ml in PBS and 100 µl/well in 96-well plates (Nunc Immuno Plate Maxisorp). Coated plates were covered and incubated at 4° C. overnight. Plates were then washed 4 times with 0.05% Tween (Tween 20) in PBS and were blocked with 1% bovine serum albumin (BSA)/1% goat serum in PBS, at a volume of 200 µl/well. After incubation with the blocking buffer at 37° C. for 2 hours, the plates were washed 4 times with 0.05% Tween and tapped dry on paper towels.

B. Incubation with test samples and secondary antibody. Test samples were diluted to the proper concentrations in sample buffer, which contained 1% BSA/1% goat serum/0.05% Tween in PBS. A standard curve was prepared with a chimeric antibody (bearing a human Fc), the concentration of which was known. To prepare a standard curve, serial dilutions are made in the sample buffer to give a standard curve ranging from 125 ng/ml to 3.9 ng/ml. The diluted samples and standards were added to the plate, at a volume of 100 µl/well and the plate was incubated at 37° C. for 2 hours.

After incubation, the plate was washed 8 times with 0.05% Tween in PBS. To each well was then added 100 µl of the secondary antibody (the horse radish peroxidase (HRP)-conjugated anti-human IgG available from Jackson Immuno Research), diluted around 1: 120,000 in the sample buffer. The exact dilution of the secondary antibody had to be determined separately for each lot of the HRP-conjugated anti-human IgG. After incubation at 37° C. for 2 hours, the plate was then washed 8 times with 0.05% Tween in PBS.

C. Development. The ready-made substrate solution (TMB Substrate, BioFX Laboratories, Md.) was added to the plate at 100 µl/well and the color was allowed to develop at room temperature for 10 minutes. The reaction was stopped by adding 1N HCl, 100 µl/well. The plate was read by a plate reader, which was set to a wavelength of 450 nm.

1C: Analytical HPLC Based Method for Determining Protein Concentration

Protein concentrations were also determined using analytical HPLC. A standard curve for protein concentration over the range of about 0.78 to 50.0 µg/ml was determined using a pH-based elution protocol with a POROS column (Perceptive Biosystems) on an Agilent 1100 HPLC system, and with the immunoconjugate KS-IL2 as a standard.

Example 2

Determination of the Relative Binding Affinity of the Epitope-Depleted Leu-16 Antibody-IL2 Fusion Protein for Daudi Tumor Cells Presenting the CD20 Antigen The binding of a epitope-depleted Leu16-IL2 fusion protein of the invention, Leu16VhY/VkZ-IL2 (also referred to as "anti-CD20 PC2" and AbVhY/VkZ-IL2), to Daudi lymphoma cells bearing the CD20 antigen, was compared with the binding of other known anti-CD20 antibodies using flow cytometry analysis. Approximately $10^6$ Daudi cells were used with various concentrations of antibody or antibody-IL2 fusion protein in a 100 µl volume, for each sample tested. Anti-CD20 PC2 is a fusion protein of IL2 bound to the C-terminus of the heavy chain of a modified Leu16 chimeric antibody having the VhY and VkZ variable regions and human IgG1-derived and kappa constant regions. As shown in Table 1, anti-CD20 PC2 was able to bind to CD20-expressing cells at least as well as the corresponding chimeric Leu16-IL2 fusion protein chLeu16-IL2, which has native Vh and Vk regions from Leu16, and human IgG1 and kappa constant regions, with IL-2 bound to the C-terminus of the heavy chain as in anti-CD20 PC2. These results demonstrate that the mutations introduced into the Leu16 V-regions to generate VhY and VkZ did not interfere with antigen binding. Anti-CD20 PC2 also compared favorably to RITUXAN (C2B8), as well as the 2B8-IL2 fusion protein, both of which contain the murine 2B8 V-regions. Data in Table 1 below shows the mean fluorescence intensity, as measured in a flow cytometer, of Daudi cells exposed to different concentrations of antibody or antibody-IL2 fusion protein; this data represents a typical set of experimental results.

TABLE 1

| | Antibody Concentration (g/ml) | | | | | | | |
|---|---|---|---|---|---|---|---|---|
| Antibody | 10 | 5 | 2.5 | 1.25 | 0.625 | 0.313 | 0.156 | 0.078 |
| 2B8-IL2 | 857.32 | 720.02 | 512.81 | 369.04 | 229.45 | 147.26 | 85.32 | 52.13 |
| anti-CD20 PC2 | 987.54 | 848.56 | 677.11 | 539.35 | 336.41 | 219.48 | 124.33 | 74.77 |
| chLeu16-IL2 | 789.20 | 665.20 | 489.04 | 363.00 | 219.06 | 131.92 | 78.24 | 52.31 |
| C2B8 | 997.18 | 816.47 | 647.43 | 491.38 | 311.52 | 215.34 | 130.70 | 86.48 |

Example 3

Figure 5:
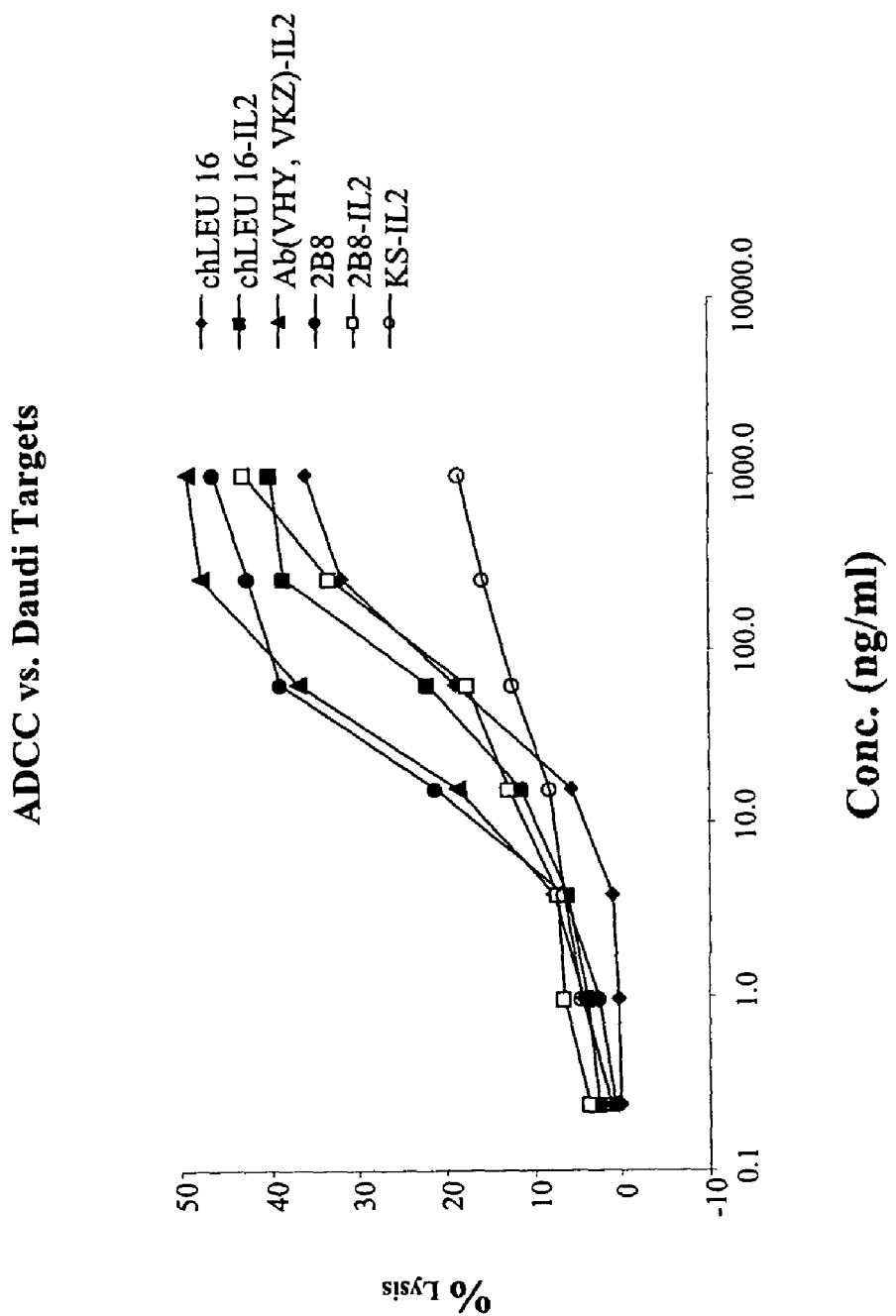
FIG. 5 is a graphical representation of an antibody-dependent cellular cytotoxicity (ADCC) lysis assay described in Example 3; proteins tested were chimeric Leu16 antibody (chLeu16; filled diamonds), a fusion protein of chLeu16 and IL-2 (chLeu16-IL2; filled squares), a CD20 binding polypeptide composition of the invention designated herein as "Leu16VhY/VkZ-IL2" (anti-CD20 PC2) (filled triangles), chimeric 2B8 antibody (C2B8, filled circles), C2B8-IL2 fusion protein (open squares), and human KS-IL2 (huKS-IL2) immunocytokine fusion protein, which does not target CD20 (open circles).

Antibody-Dependent, Cell-Mediated Cytotoxicity (ADCC) Driven by Anti-CD20-IL2 Fusion Proteins of the Invention Carrying Mutations that Reduce Immunogenicity NS/0 cells that express CD20 were exposed to various concentrations of antibody or antibody-IL2 fusion protein and tested for ADCC lysis according to standard procedures. A typical data set is shown in FIG. 5. Proteins tested were as follows: chLeu16, which is a chimeric antibody consisting of the Leu16 mouse V-regions and human IgG1 constant regions; chLeu16-IL2 which is a chimeric antibody consisting of the Leu16 mouse V-regions and human IgG1-derived constant regions, with a human IL-2 moiety fused to the C-terminus of the antibody heavy-chain; anti-CD20 PC2 (also referred to as Ab(VhY/VkZ)-IL2 and Leu16VhY/VkZ-IL2), which is identical to chLeu16-IL2 except that the VhY and VkZ variable domains shown in FIGS. 3 and 4 are present instead of the native murine Leu16 V-regions; C2B8, which is a chimeric antibody consisting of the 2B8 mouse V-regions and human IgG1-derived constant regions; 2B8-IL2, which is a chimeric antibody consisting of the 2B8 mouse V-regions and human IgG1 constant regions, with a human IL-2 moiety fused to the C-terminus of the antibody heavy chain; KS-IL2, which is an anti-EpCAM antibody fused to human IL-2 at the C-terminus of the antibody heavy chains; and anti-CD20 PC3, which is a deglycosylated version of anti-CD20 PC2. The KS-IL2 protein serves as a negative control. Certain of the antibody-IL2 fusion proteins had mutations of the C-terminal heavy chain amino acids as described by Gillies et al. (WO02/66514, WO02/079415, WO01/058957); these mutations had no effect on the ADCC data.

The data in FIG. 5 indicate that a fusion protein bearing the VhY and VkZ variable regions (i.e., anti-CD20 PC2) was as active as similar molecules carrying CD20-binding murine V-regions in stimulating ADCC.

IL-2 activity was determined by several different cellular assays. Results are presented in Table 2.

TABLE 2

| | T Cell CTLL-2 $ED_{50}$ (ng/ml) | HU PBMC $ED_{50}$ (ng/ml) | T Cell Kit-225 $ED_{50}$ (ng/ml) | +IL-2 Rβ TF-1β $ED_{50}$ (ng/ml) |
|---|---|---|---|---|
| KS IL2 | 1.71 | 2.09 | 0.08 | 0.51 |
| human rIL-2 | 0.65 | 1.51 | 0.07 | 0.71 |
| chLeu16-IL2 | | | 0.06 | 1.15 |
| anti-CD20 PC2 | 1.94 | 2.03 | 0.05 | 1.14 |
| anti-CD20 PC3 | 3.30 | 3.42 | 0.09 | 1.99 |

IL-2 based immunocytokines that target CD20, such as anti-CD20 PC2 and anti-CD20 PC 3 are highly efficacious in SCID mouse models of well established lymphoma, at least in the absence of normal human B cells expressing the same surface antigen. The use of immunocytokines was far more effective than that of the "naked" antibody (i.e., without a fused IL-2) in extending the survival of mice with disseminated disease, despite the lack of functional T cells, i.e., cells that have been identified in many pre-clinical studies to be the primary effectors of immunocytokine anti-tumor activity.

Anti-tumor activity of separate antibody and IL-2 components. Clinical trials combining rituximab and IL-2 have shown increased response rates (Friedberg et al. Br. J. Haematol. (2002); 117: 828-834). This combination was tested in the same Daudi lymphoma model using two different approaches and compared to treatment with Leu16VhY/VkZ-IL2. In the first case, animals were dosed i.v. for 5 consecutive days with the equivalent molar amounts of Leu16VhY/VkZ antibody and IL-2 contained in 20 mg of Leu16VhY/kZ-IL2 (anti-CD20 PC2). In the second case, 25 mg/kg of rituximab and 10 mcg of IL-2 were given s.c. every other day for 3 doses. This latter dosing regimen would ensure high levels of antibody as well as a sustained IL-2 activation due to the depot effect of s.c. administration. Results indicated that the two combination protocols resulted in roughly the same degree of anti-tumor activity, with 50% survival of 63 days (FIG. 14). Treatment with the equivalent amount of Leu16VhYAVkZ-IL2 immunocytokine, used in the low dose combination group, resulted in long-term survival of all mice. This is particularly noteworthy since the groups treated with the separate antibody and IL-2 are exposed to antibody for a much longer time than Leu16VhY/VkZ-IL2 due to its much longer half-life. Furthermore, the amounts of IL-2 used for comparison were based on mass and not on IL-2 activity units. As shown in Table 2, above, free rIL-2 is approximately 3-fold more active than the equivalent molar amount of IL-2 contained in Leu16VhY/VkZ-IL2 when measured with a mouse cell line expressing the high affinity IL-2R. For mouse immune cells expressing only the intermediate IL-2 Rβ, this difference is more than 10-fold in favor of free rIL-2.

Example 4

Complement-Dependent Cytotoxicity (CDC) Driven by Anti-CD20-IL2 Fusion Proteins Carrying Mutations that Reduce Immunogenicity To determine CDC activity of antibodies and fusion proteins of the invention, $^{51}$Cr-labeled Daudi cells were incubated for 1 hour with human plasma (diluted 1 in 8) as a source of complement. Percentage of specific lysis was calculated by subtracting the background radioactivity from the experimental values, dividing by the total releaseable radioactivity obtained by detergent lysis, and multiplying by 100.

Figure 7:
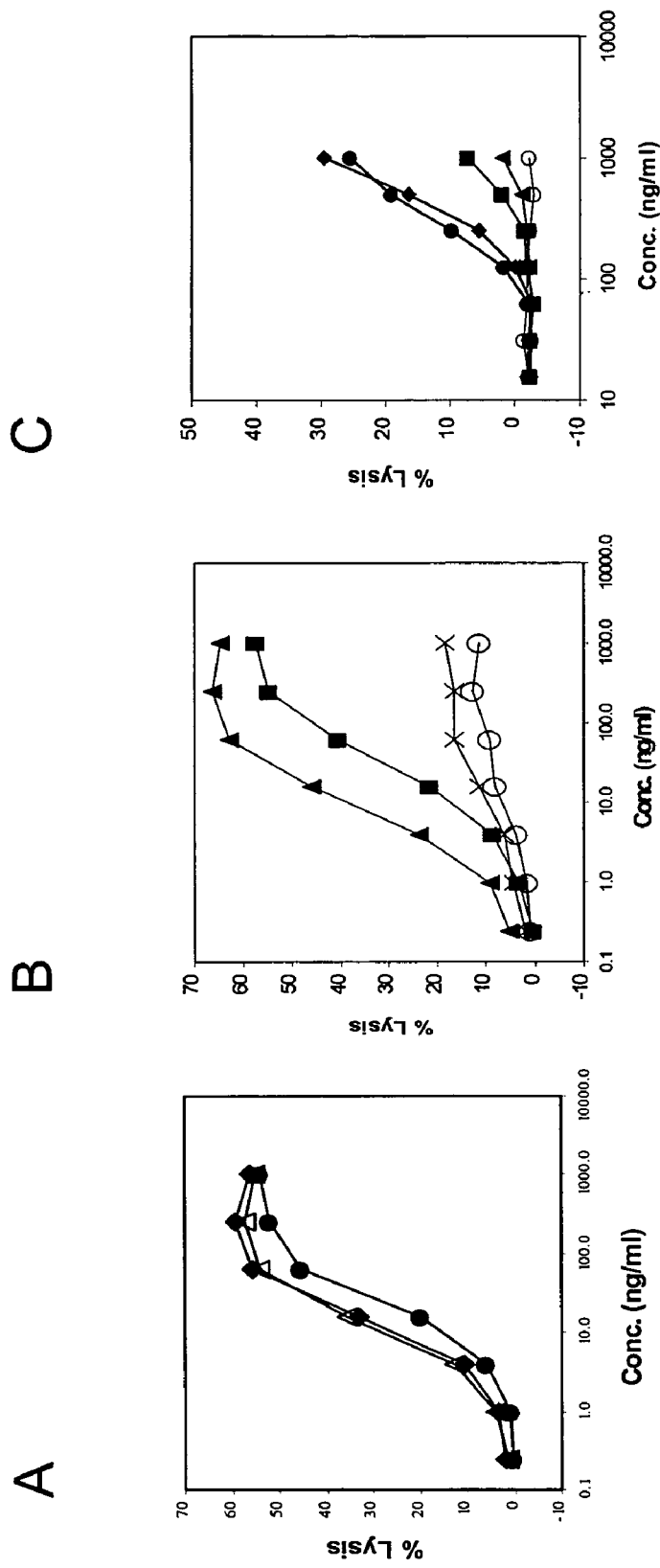
FIG. 7 illustrates antibody-dependent cell-mediated and complement-dependent cytotoxicity. Panels A and B represent independent ADCC tests compared to FIG. 5. ADCC was determined in a 4-hour assay using $^{51}$Cr-labeled Daudi target cells and human PBMC as effectors (E:T=100). Panel A: Antibodies tested were 2B8 (filled circles), chLeu16 (filled diamonds), and Leu16VhY/VkZ (anti-CD20 PC1) (open triangles). Panel B: Immunocytokines tested were chLeu16-IL2 (filled squares), and Leu16VhY/VkZ-IL2 (anti-CD20 PC2) (filled triangles), deglycosylated Leu16VhY/VkZ-IL2 (anti-CD20 PC3) (X's), and huKS-IL2 (open circles) as a nonbinding control. Panel C shows CDC activity using $^{51}$Cr-labeled Daudi cells and human plasma as a source of complement, as described in Example 4. Incubation was for 1 hour using the same antibodies and immunocytokines. Antibodies tested were 2B8 (filled circles), chleu16 (filled diamonds), chLeu16-IL2 (filled squares), and Leu16VhY/VkZ-IL2 (filled triangles), and huKS-IL2 (open circles) as a nonbinding control.

A comparison of the CDC activities of the chimeric Leu-16 antibody and the corresponding Leu16 antibody with epitope-depleted V-regions (i.e. anti-CD20 PC1) indicates that the activities of these two antibodies were essentially identical (see FIG. 7, Panel A). A similar comparison of the CDC activities of the chimeric Leu-16 antibody-IL2 fusion and the corresponding Leu16 antibody-IL2 fusion with epitope-depleted V-regions (anti-CD20 PC2) indicates that the activities of these two fusion proteins were also essentially identical (see FIG. 7, Panel B).

In contrast to ADCC, CDC was somewhat reduced as a consequence of fusing IL-2 to the C-terminus of the heavy chain (FIG. 2, panel B). A similar effect was reported earlier with an anti-GD2 immunocytokine (Gillies S D, et al. Cancer Res. (1999); 59:2159-2166.) (see FIG. 7, Panel C).

Example 5

Pharmacokinetic Profile of an Epitope-Depleted Leu16-IL2 Fusion Protein

Figure 8:
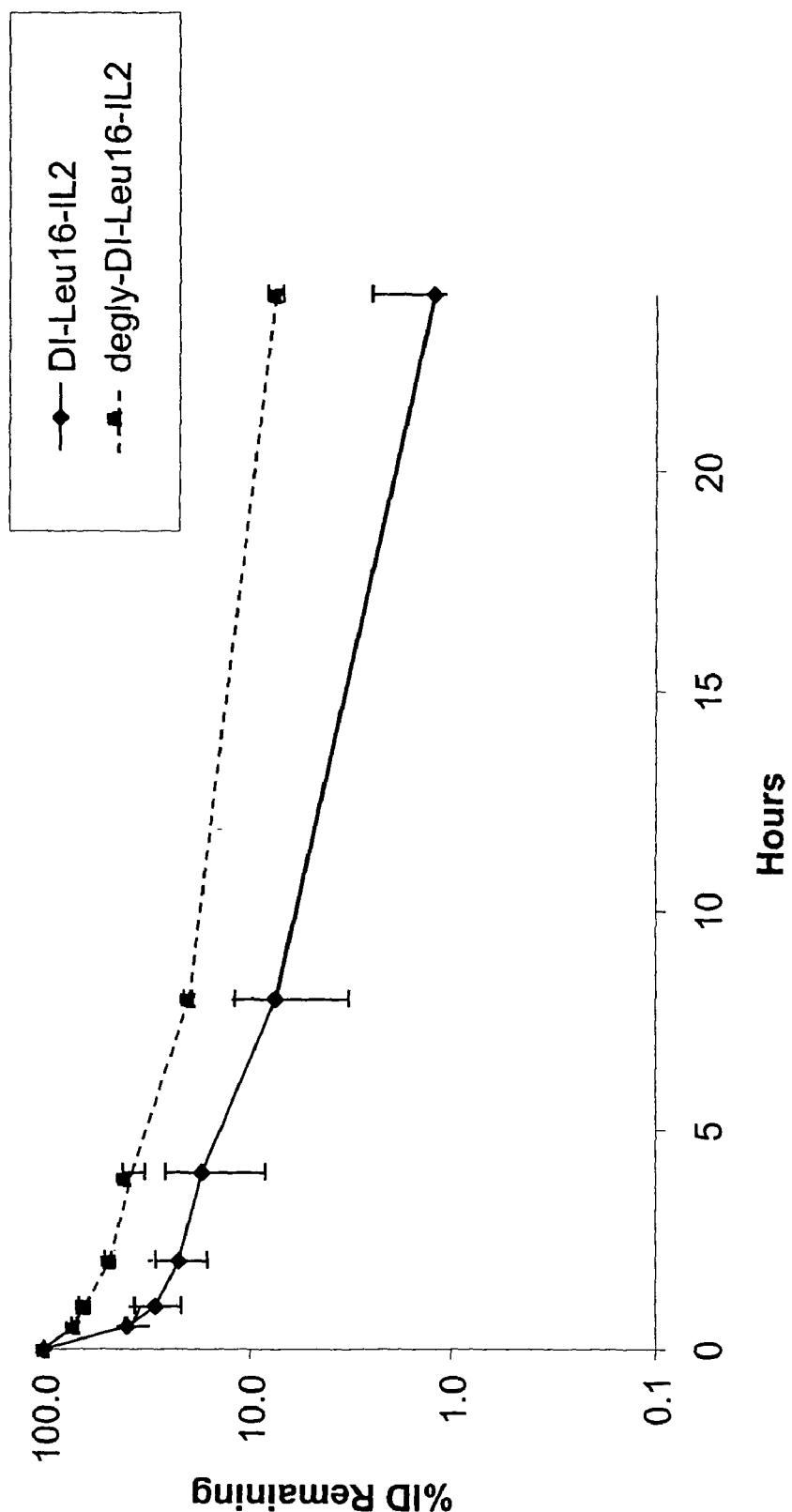
FIG. 8 illustrates the pharmaco-kinetics of epitope-depleted Leu16 immunocytokines in mice, as described in Example 5. A time-concentration analysis was performed following an intravenous (i.v.) dose of each immunocytokine. Serum concentrations were determined by an ELISA that detects the intact forms for the native (filled diamonds) and de-glycosylated proteins (filled squares).

FcR binding and ADCC activity of a Leu16VhY/VkZ-IL2 fusion protein were maintained relative to chLeu16-IL2 by using an identical IgG1 heavy chain isotype. The resulting protein had a favorable pharmacokinetic profile following i.v. administration, especially during the distribution a phase (FIG. 8).

The effect of FcR binding on the pharmacokinetic profile was examined by testing the enzymatically de-glycosylated Leu16VhY/VkZ (Lys-Ala)-IL2 in the same experiment. The results indicate that loss of FcR binding improved the pharmacokinetic behavior somewhat. Depending on the application and the desired frequency of administration, it may be preferable to use a Leu16VhY/VkZ-IL2 molecule with the N-linked glycosylation site in the CH2 domain, which has ADCC activity but a relatively shorter serum half-life, or a Leu16VhY/VkZ-IL2 molecule lacking the N-linked glycosylation site in the CH2 domain, which has no ADCC activity but a relatively longer serum half-life.

Example 6

Efficacy Profile of an Epitope-Depleted Leu16-IL2 Fusion Protein

Figure 9:
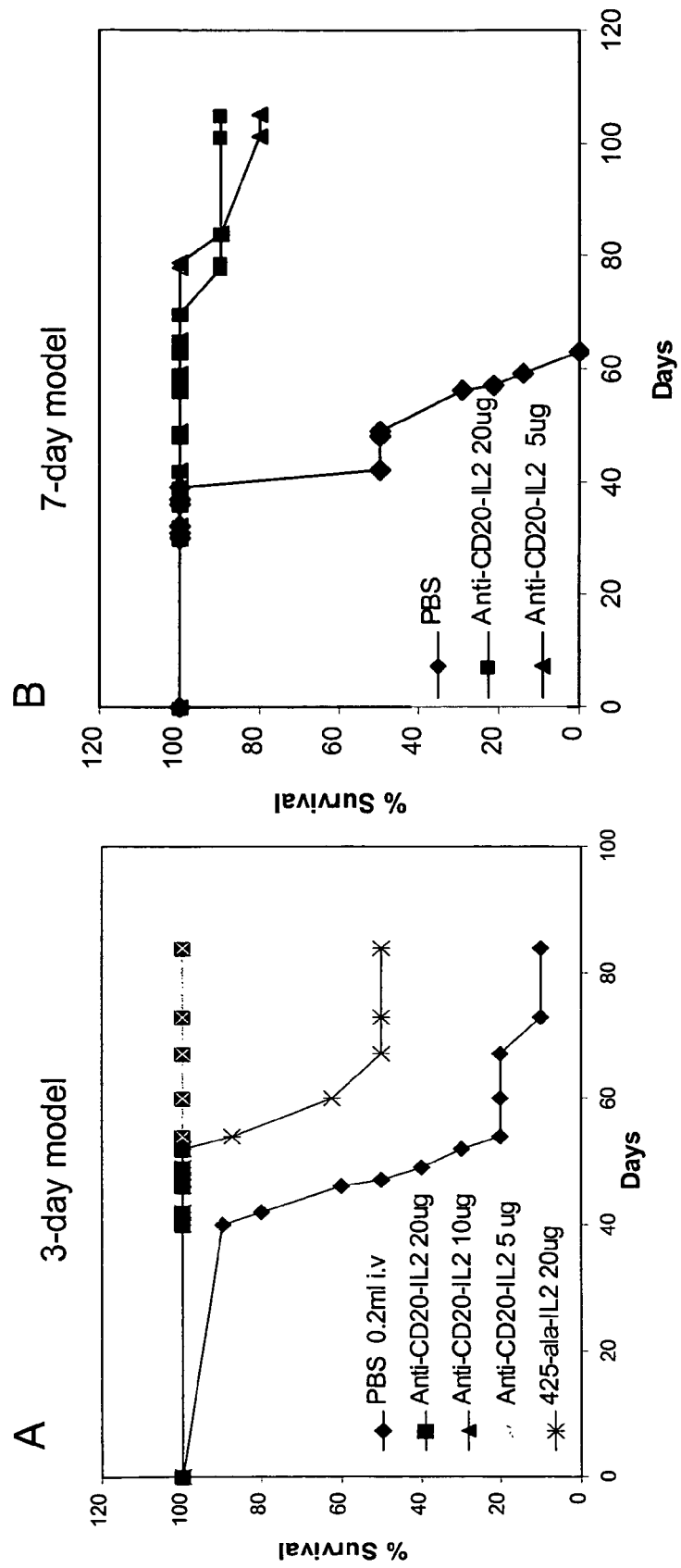
FIG. 9 shows anti-tumor model evaluations in SCID mice. SCID mice were injected i.v. with 2×10$^6$ CD20+ Daudi lymphoma cells followed by 5 consecutive daily injections of immunocytokines beginning on Day 3 (Panel A) or Day 7 (Panel B). The non-targeting control immunocytokine 425-IL2, specific for EGFR, was used at the high dose to illustrate the incomplete activity due to the altered half-life of IL-2. Treatments in Panel A were administered on Days 3, 4, 5, 6, and 7 and included PBS only (filled diamonds); 425-IL2 (dark, crossed X's); and Leu16VhY/VkZ-IL2 (anti-CD20 PC2) at daily doses of 5 micrograms (mcg) (light Xs), 10 mcg (filled triangles), and 20 mcg (filled squares). In Panel A, the latter three doses all showed complete protection of the mice, and the datapoints are superimposed. Treatments in Panel B were administered on Days 7, 8, 9, 10, and 11, and included PBS only (filled diamonds); and Leu16VhY/VkZ-IL2 at daily doses of 5 mcg (light Xs); and 20 mcg (filled squares).
Figure 10:
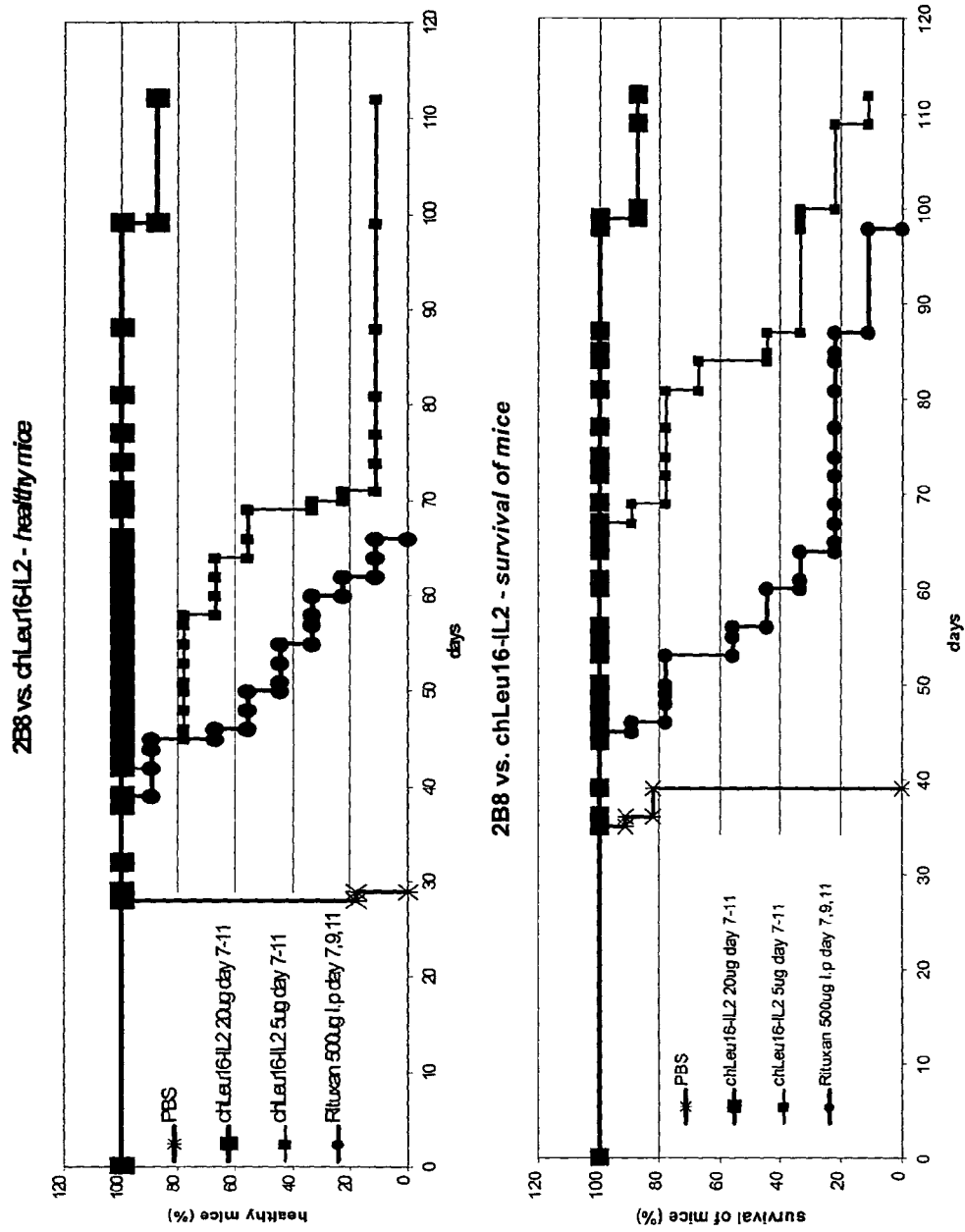
FIG. 10 shows the results of anti-tumor model evaluations in SCID mice; SCID mice were injected with Daudi lymphoma cells and treated with the indicated antibody or immunocytokine beginning 7 days later, as described for FIG. 9. Treatments included PBS only (crossed Xs, on Days 7-11); rituximab (C2B8; filled circles, 25 mg/kg on Days 7, 9 and 11); high dose Leu16VhY/VkZ-IL2 (anti-CD20 PC2) (large squares, 1 mg/kg on Days 7-11); low dose Leu16VhY/VkZ-IL2 (small squares, 0.25 mg/kg on Days 7-11).
Figure 11:
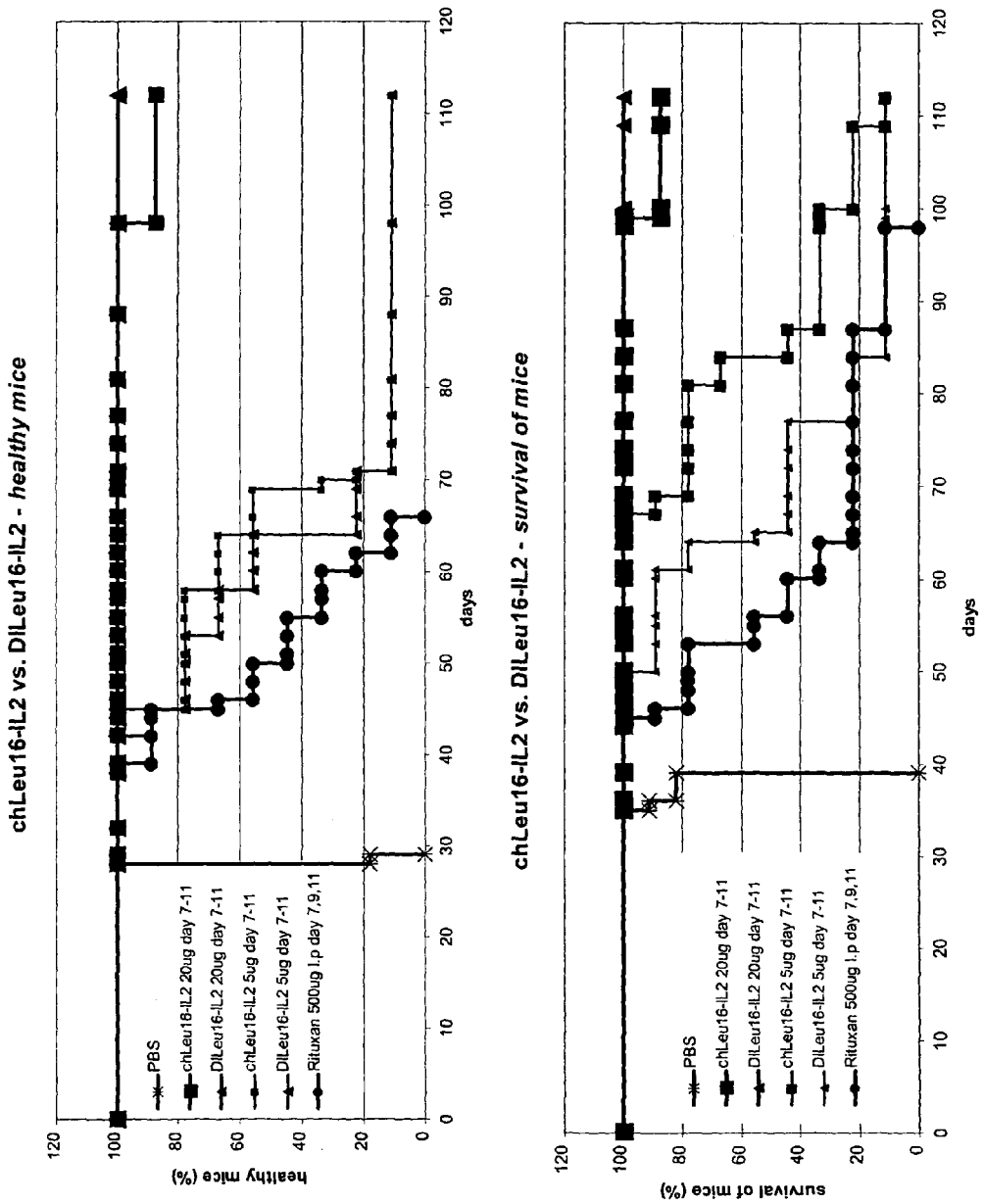
FIG. 11 shows the results of anti-tumor model evaluations in SCID mice; SCID mice were injected with Daudi lymphoma cells and treated with the indicated antibody or immunocytokine beginning 7 days later, as described for FIG. 9.

SCID mice were injected i.v. with 5×10$^6$ CD20+ Daudi lymphoma cells (Day 0) followed by i.v. injection of immunocytokines (5 daily doses of 5 or 20 mg) or control antibody (500 mg every other day for a total of 3 doses) beginning on Day 7. A low-targeting control immunocytokine 425-IL2, specific for EGFR (control), was used at the high dose to demonstrate activity due primarily to the altered half-life of IL-2. Results were recorded as general health, e.g. paralysis, which preceded death by 10-14 days, and survival of mice. FIGS. 9-11 show typical results. Data in FIGS. 10-12 are from a single, large experiment, but the data are presented in different figures for ease of viewing.

In the first anti-tumor experiments Daudi cells were injected i.v. into SCID mice resulting in extensive disseminated disease leading to paralysis of all mice by day 30. Treatment was delayed until day 7 to ensure the tumor cells had fully engrafted. We compared low and moderate doses of both rituxamab and Leu16VhY/VkZ-IL2 (anti-CD20 PC2) immunocytokines to high dose rituximab using 5 daily doses of the immunocytokines and 3 alternate day doses of the antibody. This schedule was chosen due to the much longer circulating half-life of rituximab (several days) compared to the immunocytokines (about 8 hours). Under these conditions, rituximab (25 mg/kg×3) extended the 50% survival of tumor bearing mice from 39 to 56 days, relative to the PBS control (FIG. 4). The low dose chimeric and Leu16VhY/VkZ-IL2 groups (0.25 mg/kg×5) had similar survival curves (50% survival at 64 days) as the high-dose rituximab. The groups treated with the higher doses of the immunocytokines (1 mg/kg×5) showed a dramatic increase in survival with no mouse deaths in the Leu16VhY/VkZ-IL2 group at the termination of the experiment (Day 110) and only 1 of 8 mice dead in the chLeu16-IL2 group. Thus, the epitope-depleted V-regions of the Leu16 antibody were as effective as those of the murine Leu16 antibody, in the context of an IL-2 based immunocytokine, for the treatment of disseminated lymphoma in SCID mice.

Figure 6:
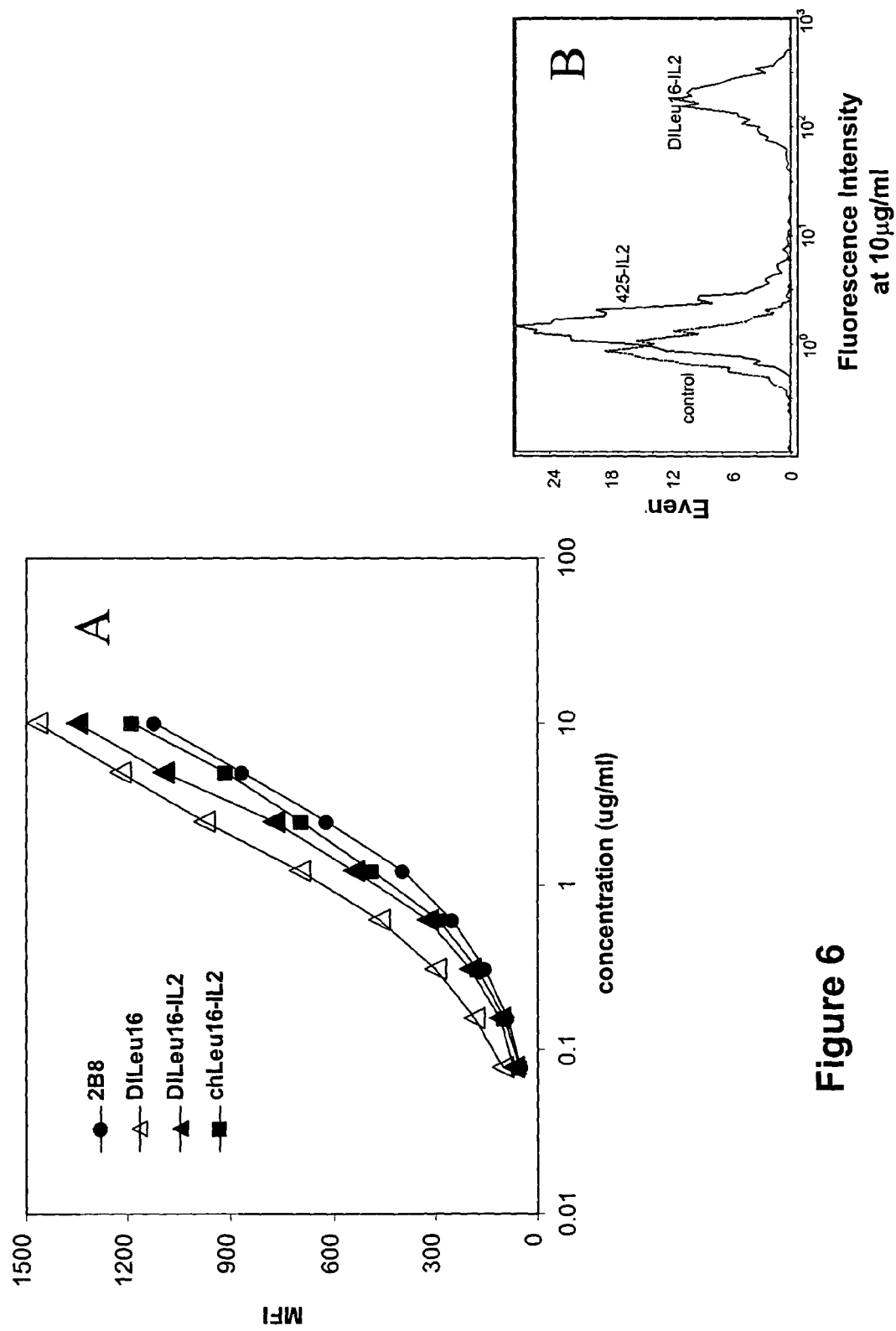
FIG. 6 illustrates the anti-CD20 binding activity of CD20-binding polypeptide compositions and immunocytokines (ICs). Human Daudi lymphoma cells were incubated with varying concentrations of polypeptide compositions and ICs and relative binding to the cells was assessed by flow cytometry, as described in Example 2. Panel A shows the mean fluorescence intensity (MFI, Y axis), which increases as a function of polypeptide concentration (X axis). Materials tested were chimeric 2B8 antibody (labeled 2B8, filled circles), Leu16VhY/VkZ (labeled DILeu16, open triangles), Leu16VhY/VkZ-IL2 (labeled DILey16-IL2, filled triangles), and chimeric Leu16-IL2 (labeled chLeu16-IL2, filled squares). Panel B shows the fluorescence intensity measured on a Daudi cell sample with no primary antibody present (leftmost peak, labeled control); an antibody-IL2 fusion directed against EGF receptor (425-IL2), which is not expressed on Daudi cells (left-central peak); and Leu16VhY/VkZ-IL2 (anti-CD20 PC2) (right-most peak, labeled DILeu16-IL2).

FIG. 6 illustrates the anti-CD20 binding activity of CD20-binding polypeptide compositions and immunocytokines (ICs). Human Daudi lymphoma cells were incubated with varying concentrations of polypeptide compositions and ICs and relative binding to the cells was assessed by flow cytometry, as described in Example 2. Panel A shows the mean fluorescence intensity (MFI, Y axis), which increases as a function of polypeptide concentration (X axis). Panel B shows the fluorescence intensity measured on a Daudi cell sample with no primary antibody present (leftmost peak, labeled control); an antibody-IL2 fusion directed against EGF receptor (425-IL2), which is not expressed on Daudi cells (left-central peak); and Leu16VhY/VkZ-IL2 (anti-CD20 PC2) (right-most peak, labeled DILeu16-IL2).

In the same experiment, the contribution of antibody effector function on anti-tumor activity was also tested using the enzymatically de-glycosylated Leu16VhY/VkZ-IL2 (anti-CD20 PC3), which was shown above to have lost ADCC activity (FIG. 7, Panel B). As shown in FIG. 12, a significant portion of the anti-tumor activity was preserved despite the loss of ADCC activity. At later time points, a marked difference between the intact and de-glycosylated forms was observed in the higher dose groups. Therefore, while ADCC appears to play a role in this model, a good deal of the anti-tumor activity in this model can be attributed to targeted delivery of IL-2 to the tumor alone.

To address the importance of actual binding of an epitope-depleted immunocytokine to a target cell, as opposed to an effect of simply extending the serum half-life of IL-2, a control IL-2 immunocytokine targeting EGFR (Cruz et al. *J. Biotechnol*. (2002) 26; 96:169-183), which is expressed at only very low levels (FIG. 6, Panel B) on this cell line, was tested. It was found that even the higher dose (1 mg/kg) given 5 consecutive days had far less anti-tumor activity in this model than the same dose of the immunocytokines targeting CD20 (FIG. 13).

The EGFR-targeted immunocytokine also had significantly less activity than the same dose of Leu16VhY/VkZ-IL2 given only twice, three days apart (Days 7 and 10), or at a four-fold lower dose given over 5 days. These results demonstrate the importance of specific tumor cell targeting for anti-tumor activity.

Example 7

Antitumor Activity of Leu16VhY/VkZ Molecules in Mice Reconstituted with Human Immune Cells In the SCID model reconstituted with human B cells, mice were injected i.v. with $5 \times 10^6$ CD20+Daudi lymphoma cells on Day 0 and $4.5 \times 10^7$ human PBMC on C 5. One group (n=8) of mice received PBS only; one group received antibody only (500 mg on Days 7, 9 and 11); one group received immunocytokine only (20 mg on Days 11-15); and one group received the combination of antibody (500 mg on Days 7, 9 and 11) and immunocytokine (20 mg on Days 11-15). All mice were checked for the presence of human antibodies in their serum by anti-human IgG ELISA on Days 21 and 34.

Targeting CD20 on B lymphoma cells is complicated by the fact that the antigen is expressed on normal B cells. Thus, therapy involves the targeted depletion of tumor cells in the background of a vast number of normal B cells. Since IL-2 immunocytokine dosing is likely to be limited by the toxicity of the IL-2 component, it is unlikely that the high doses required for normal B cell depletion by the naked antibody could be used for Leu16VhY/VkZ-IL2. Combination treatment is a likely clinical approach in which Leu16VhY/VkZ-IL2 therapy would follow rituximab treatment to first de-bulk both CD20+ tumor cells and normal B cells.

In an attempt to create a more realistic tumor model mice were injected with PBMC containing human B cells and then compared monotherapy with rituximab or Leu16VhY/VkZ-IL2 (labeled DILeu16-IL2 in Table 3) as well as the combination in which the antibody is given as a single dose at Day 7, followed by a course of therapy with Leu16VhY/VkZ-IL2 beginning on Day 11. A second set of mice were not implanted with human PBMC but received the same treatment regimens. Confirmation that B cells had been implanted was obtained by measuring levels of human IgG in all mice groups. Data in Table 3 show that mice receiving human PBMC all had levels of human IgG of >500 µg/ml demonstrating efficient grafting.

TABLE 3

Human antibody production in SCID mice implanted with human PBMC

| Treatment Group | Day 21 | | Day 34 | |
| --- | --- | --- | --- | --- |
| | −B Cells | +B Cells | −B Cells | +B Cells |
| PBS | NT | >500 | 0 | >500 |
| DI-Leu16-IL2 (d11-15) | NT | 64.1 | 0.83 | 88.31 |
| Rituximab (d7) | NT | 14.32 | 9.12 | 6.18 |
| Combination | NT | 9.55 | 6.0 | 5.8 |

Human antibodies were quantitated by anti-IgG ELISA and represent mcg/ml. Antibodies detected in the—B cell group show the contribution of rituximab and Leu16VhY/VkZ-IL2 (DI-Leu16-IL2, both human IgG) to the total circulating antibody.

Antibody levels at Day 21 show dramatic decreases in all treatment groups, including monotherapy with Leu16VhY/VkZ-IL2, however the IgG level increased slightly by day 34 indicating continued production by B cells. Treatment with rituximab or the combination, on the other hand, resulted in elimination of human antibody production by Day 34. The remaining levels detected in the blood of mice in both rituximab and combination treated groups were clearly rituximab itself, since the same levels were seen in the corresponding groups that were not implanted with PBMC.

Results also showed that the anti-tumor activities of all treatment groups were not significantly affected by the presence of CD20+ human B cells (FIG. 15). Without wishing to be bound by theory, this may be due in part to the ability of Leu16VhY/VkZ-IL2 alone to eliminate the majority of implanted B cells, as well as tumor cells. The level of activity of Leu16VhY/VkZ-IL2 in this model was markedly reduced compared to earlier experiments due to the delay in initiating treatment (Day 11 vs. Day 7) however, it should be noted that only a single course of treatment was used to compare different molecules and additional cycles of treatment would be used clinically. The combination of a single dose of rituximab, followed by a single course of Leu16VhY/VkZ-IL2 had at least additive anti-tumor activity with the majority of mice remaining disease free at the end of the experiment (Day 120).

Example 8

General Methods for Removing T Cell Epitopes from Anti-CD20 Antibodies

Haisma et al. (*Blood* 92:184 (1998)) have described another anti-CD20 antibody, termed 1H4, whose V-regions are about 95% identical to the V-regions of Leu16. FIG. 16 shows an alignment of the heavy and light (kappa) V-regions of 2B8, Leu16, their epitope-depleted derivatives according to the invention, and 1H4.

From the finding that the antibodies 2B8, Leu16, and 1H4 are so similar in sequence, it is likely that all of these antibodies recognize the same epitope in CD20. Without wishing to be bound by theory, it is believed that CD20 is a highly conserved protein between mouse and humans, and that there is a sequence CEPANPSEKNSPSTQYC (SEQ ID NO: 38) in the extracellular domain of human CD20 that corresponds to the sequence CEPSNSSEKNSPSTQYC (SEQ ID NO: 29) in mouse CD20. In human CD20, the sequence NPS (underlined) is not N-glycosylated, while the corresponding sequence NSS (underlined) in mouse CD20 is N-glycosylated. The lack of N-glycosylation in the human CD20 reveals an antibody epitope that is absent in mouse CD20, so that when mice are immunized with human CD20, this epitope will not be recognized as "self" by the mouse immune system.

Thus, according to the invention, the native V-regions of a monoclonal antibody directed against CD20 are at least 80% identical in sequence, and more often at least 90% identical in sequence, to Leu16 or 2B8 V-regions. The antibody 1H4 is one such example. Accordingly, T cell epitopes in an anti-CD20 antibody, for example 1H4, can be removed by first aligning the heavy and light chain V-regions with Leu16, 2B8, and the corresponding epitope-depleted variants shown in FIG. 16, and then by introducing mutations in the V-regions of the CD20 antibody, such as 1H4, that correspond to the mutations introduced in epitope-depleted versions of Leu16 and/or 2B8. The alignments can be performed by manual alignment or using well-known alignment programs such as BLAST.

For example, using the alignments in FIG. 16, it is apparent that an anti-CD20 Vh domain with one or more of the following amino acid segments is generated: SGAELKKPGAS, VSCKASGYT, LEWTGAIY, YNQKFKGKT, FKGKTTLTA, YMELSSLRS, SSLRSEDTAV, and DWGTGTTVT (i.e., SEQ ID NO: 15-22, respectively). Similarly, using the alignments in FIG. 16, it is apparent that an anti-CD20 light chain variable domain with one or more of the following amino acid segments is generated: IITASPGEKV, CRASTSASY, QQKPTSSP, LASGVPSRF, FSGSGSGTT, and YSMTISSLE (i.e., SEQ ID NO: 23-28, respectively). In particular, a variant of the antibody 1H4 with one or more of the preceding amino acid segments of this paragraph can be generated, which has the utility of the newly introduced mutations, using a variety of methods known in the art. For example, methods such as those of Carr et al. (U.S. patent application Ser. No. 20030153043 and WO02/069232) may be used. Alternatively, peptides corresponding to potential T cell epitopes may be added to immune cells, preferably human immune cells, and tested for the ability to stimulate cell proliferation according to standard techniques.

The corresponding V-region-containing polypeptide compositions can be configured as whole antibodies, antibody fusion proteins, Fabs, Fab fusion proteins, single-chain Fv proteins, or other standard configurations of antibody V-regions. The corresponding V-region-containing polypeptide compositions are then produced according to standard protein expression methods, such as are described in the Examples above.

We claim:

1. A CD20-binding polypeptide composition comprising a combination of a modified heavy chain variable region polypeptide and a modified ht chain variable region polypeptide, the combination being selected from the group consisting of:

(a) a combination of a modified 2B8 antibody heavy chain variable region polypeptide having the amino acid residue sequence of SEQ ID NO: 48 and which includes at least one of the following amino acid residues: K at residue 12, P at residue 14, V at residue 20, T at residue 48, T at residue 68, E at residue 82, R at residue 87, T at residue 91, and W at residue 106; and a modified 2B8 antibody light chain variable region polypeptide having the amino acid residue sequence of SEQ ID NO: 49 and which includes at least one of the following amino acid residues: I at residue 11, T at residue 12, T at residue 27, A at residue 29, T at residue 40, S at residue 59, T at residue 69, M at residue 72, S at residue 76, and L at residue 77; and (b) a combination of a modified Leu16 antibody heavy chain variable region polypeptide having the amino acid residue sequence of SEQ ID NO: 50 and which includes at least one of the following amino acid residues: K at residue 12, V at residue 20, T at residue 68, E at residue 82, R at residue 87, T at residue 91, V at residue 93, and T at residue 114; and a modified Leu16 antibody light chain variable region polypeptide having the amino acid residue sequence of SEQ ID NO: 51 and which includes at least one of the following amino acid residues: I at residue 11, T at residue 12, S at residue 59, T at residue 69, M at residue 72, S at residue 76, and L at residue 77.

2. The CD20-binding polypeptide composition of claim 1 in the form of a chimeric antibody and further including a human heavy chain constant region and a human light chain constant region.

3. The CD20-binding polypeptide composition of claim 2 wherein the human heavy chain constant region is an IgG constant region.

4. The CD20-binding polypeptide composition of claim 3 wherein the IgG constant region is an IgG1 constant region.

5. The CD20-binding polypeptide composition of claim 2 wherein the human light chain constant region is a human kappa light chain constant region.

6. The CD20-binding polypeptide composition of claim 2 in the form of a fusion protein with human IL-2.

7. The CD20-binding polypeptide composition of claim 1, in the form of a fusion protein with human IL-2.

8. The CD20-binding polypeptide composition of claim 1 in the form of a Fab antibody fragment, a single-chain Fv antibody fragment, and minibody.

9. A CD20-binding polypeptide composition comprising (a) a modified 2B8 antibody heavy chain variable region polypeptide having an amino acid residue sequence selected from the group consisting of SEQ ID NO: 2 and SEQ ID NO: 3; and a modified 2B8 antibody light chain variable region polypeptide having an amino acid residue sequence selected from the group consisting of SEQ ID NO: 5, SEQ ID NO: 6, SEQ ID NO: 7, and SEQ ID NO: 8; or (b) a modified Leu16 antibody heavy chain polypeptide having the amino acid residue sequence of SEQ ID NO: 10 and a modified Leu16 antibody light chain variable region polypeptide having the amino acid residue sequence of SEQ ID NO 12.

10. The CD20-binding polypeptide composition of claim 9 comprising a polypeptide having an amino acid residue sequence of SEQ ID NO: 2 and a polypeptide having an amino acid residue sequence of SEQ ID NO: 5.

11. The CD20-binding polypeptide composition of claim 9 comprising a polypeptide having an amino acid residue sequence of SEQ ID NO: 2 and a polypeptide having an amino acid residue sequence of SEQ ID NO: 6.

12. The CD20-binding polypeptide composition of claim 9 comprising a polypeptide having an amino acid residue sequence of SEQ ID NO: 2 and a polypeptide having an amino acid residue sequence of SEQ ID NO: 7.

13. The CD20-binding polypeptide composition of claim 9 comprising a polypeptide having an amino acid residue sequence of SEQ ID NO: 2 and a polypeptide having an amino acid residue sequence of SEQ ID NO: 8.

14. The CD20-binding polypeptide composition of claim 9 comprising a polypeptide having an amino acid residue sequence of SEQ ID NO: 3 and a polypeptide having an amino acid residue sequence of SEQ ID NO: 6.

15. The CD20-binding polypeptide composition of claim 9 comprising a polypeptide having an amino acid residue sequence of SEQ ID NO: 3 and a polypeptide having an amino acid residue sequence of SEQ ID NO: 8.

16. A CD20-binding polypeptide composition comprising a polypeptide having an amino acid residue sequence of SEQ ID NO: 10 and a polypeptide having an amino acid residue sequence of SEQ ID NO: 12.

17. A pharmaceutical composition comprising a CD20-binding polypeptide composition of claim 1, together with a pharmaceutically acceptable carrier, excipient, or diluent.

18. The pharmaceutical composition of claim 17 further comprising an additional pharmacologically effective drug.

19. The CD20-binding polypeptide composition of claim 9, designated Leu16VhY/VkZ-IL2, in the form of a fusion protein with human IL2 and comprising a polypeptide which is a Vh polypeptide having amino acid residue sequence of SEQ ID NO: 10 and a polypeptide which is a Vk polypeptide having amino acid residue sequence of SEQ ID NO: 12.

* * * * *

UNITED STATES PATENT AND TRADEMARK OFFICE
CERTIFICATE OF CORRECTION

PATENT NO.        : 8,147,832 B2                                               Page 1 of 1
APPLICATION NO.   : 10/917599
DATED             : April 3, 2012
INVENTOR(S)       : Francis Joseph Carr, Stephen Williams and Stephen D. Gillies It is certified that error appears in the above-identified patent and that said Letters Patent is hereby corrected as shown below:

Column 21,
Line 58, "Leu16VhYAVkZ-IL2" should be -- Leu16VhY/VkZ-IL2 --.

Column 23,
Line 5, "FIGS. 9-11" should be -- FIGS. 9-12 --.

Column 59,
Line 56, "ht chain" should be -- light chain --.

Signed and Sealed this
Second Day of October, 2012

David J. Kappos
*Director of the United States Patent and Trademark Office*

SEQUENCE LISTING

<160> NUMBER OF SEQ ID NOS: 51

<210> SEQ ID NO 1
<211> LENGTH: 121
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 1

Gln Val Gln Leu Gln Gln Pro Gly Ala Glu Leu Val Lys Ala Gly Ala
1 5 10 15

Ser Val Lys Met Ser Cys Lys Ala Ser Gly Tyr Thr Phe Thr Ser Tyr
20 25 30

```
Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Val Tyr Tyr Cys
                85                  90                  95

Ala Arg Ser Thr Tyr Tyr Gly Gly Asp Thr Tyr Phe Asn Val Trp Gly
            100                 105                 110

Ala Gly Thr Thr Val Thr Val Ser Ala
            115                 120

<210> SEQ ID NO 2
<211> LENGTH: 121
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 2

Gln Val Gln Leu Gln Gln Pro Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Thr
            35                  40                  45

Gly Ala Ile Tyr Pro Gly Asn Gly Asp Thr Ser Tyr Asn Gln Lys Phe
        50                  55                  60

Lys Gly Lys Thr Thr Leu Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Thr Tyr Tyr Gly Gly Asp Trp Tyr Phe Asn Val Trp Gly
            100                 105                 110

Ala Gly Thr Thr Val Thr Val Ser Ala
            115                 120

<210> SEQ ID NO 3
<211> LENGTH: 121
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 3

Gln Val Gln Leu Gln Gln Pro Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Lys Gln Thr Pro Gly Arg Gly Leu Glu Trp Ile
            35                  40                  45

Gly Ala Ile Tyr Pro Gly Asn Gly Asp Thr Ser Tyr Asn Gln Lys Phe
        50                  55                  60

Lys Gly Lys Thr Thr Leu Thr Ala Asp Lys Ser Ser Thr Ala Tyr
65                  70                  75                  80

Met Glu Leu Ser Ser Leu Arg Ser Glu Asp Thr Ala Val Tyr Tyr Cys
                85                  90                  95
```

```
Ala Arg Ser Thr Tyr Tyr Gly Gly Asp Trp Tyr Phe Asn Val Trp Gly
            100                 105                 110

Ala Gly Thr Thr Val Thr Val Ser Ala
            115                 120

<210> SEQ ID NO 4
<211> LENGTH: 106
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 4

Gln Ile Val Leu Ser Gln Ser Pro Ala Ile Leu Ser Ala Ser Pro Gly
  1               5                  10                  15

Glu Lys Val Thr Met Thr Cys Arg Ala Ser Ser Ser Val Ser Tyr Ile
             20                  25                  30

His Trp Phe Gln Gln Lys Pro Gly Ser Ser Pro Lys Pro Trp Ile Tyr
         35                  40                  45

Ala Thr Ser Asn Leu Ala Ser Gly Val Pro Val Arg Phe Ser Gly Ser
     50                  55                  60

Gly Ser Gly Thr Ser Tyr Ser Leu Thr Ile Ser Arg Val Glu Ala Glu
 65                  70                  75                  80

Asp Ala Ala Thr Tyr Tyr Cys Gln Gln Trp Ser Asn Pro Pro Thr
                 85                  90                  95

Phe Gly Gly Gly Thr Lys Leu Glu Ile Lys
            100                 105

<210> SEQ ID NO 5
<211> LENGTH: 106
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 5

Gln Ile Val Leu Ser Gln Ser Pro Ala Ile Ile Thr Ala Ser Pro Gly
  1               5                  10                  15

Glu Lys Val Thr Met Thr Cys Arg Ala Ser Thr Ser Ala Ser Tyr Ile
             20                  25                  30

His Trp Phe Gln Gln Lys Pro Thr Ser Ser Pro Lys Pro Trp Ile Tyr
         35                  40                  45

Ala Thr Ser Asn Leu Ala Ser Gly Val Pro Ser Arg Phe Ser Gly Ser
     50                  55                  60

Gly Ser Gly Thr Thr Tyr Ser Met Thr Ile Ser Ser Leu Glu Ala Glu
 65                  70                  75                  80

Asp Ala Ala Thr Tyr Tyr Cys Gln Gln Trp Thr Ser Asn Pro Pro Thr
                 85                  90                  95

Phe Gly Gly Gly Thr Lys Leu Glu Ile Lys
            100                 105

<210> SEQ ID NO 6
<211> LENGTH: 106
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 6

Gln Ile Val Leu Ser Gln Ser Pro Ala Ile Ile Thr Ala Ser Pro Gly
```

```
                 1               5                  10                 15
Glu Lys Val Thr Met Thr Cys Arg Ala Ser Thr Ser Val Ser Tyr Ile
                20                  25                 30

His Trp Phe Gln Gln Lys Pro Thr Ser Ser Pro Lys Pro Trp Ile Tyr
            35                  40                  45

Ala Thr Ser Asn Leu Ala Ser Gly Val Pro Ser Arg Phe Ser Gly Ser
        50                  55                  60

Gly Ser Gly Thr Thr Tyr Ser Met Thr Ile Ser Ser Leu Glu Ala Glu
 65                 70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 7
<211> LENGTH: 106
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 7

Gln Ile Val Leu Ser Gln Ser Pro Ala Ile Ile Thr Ala Ser Pro Gly
 1               5                  10                  15

Glu Lys Val Thr Met Thr Cys Arg Ala Ser Thr Ser Val Ser Tyr Ile
                20                  25                 30

His Trp Phe Gln Gln Lys Pro Gly Ser Ser Pro Lys Pro Trp Ile Tyr
            35                  40                  45

Ala Thr Ser Asn Leu Ala Ser Gly Val Pro Ser Arg Phe Ser Gly Ser
        50                  55                  60

Gly Ser Gly Thr Thr Tyr Ser Met Thr Ile Ser Ser Leu Glu Ala Glu
 65                 70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 8
<211> LENGTH: 106
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 8

Gln Ile Val Leu Ser Gln Ser Pro Ala Ile Ile Thr Ala Ser Pro Gly
 1               5                  10                  15

Glu Lys Val Thr Met Thr Cys Arg Ala Ser Ser Ser Val Ser Tyr Ile
                20                  25                 30

His Trp Phe Gln Gln Lys Pro Gly Ser Ser Pro Lys Pro Trp Ile Tyr
            35                  40                  45

Ala Thr Ser Asn Leu Ala Ser Gly Val Pro Ser Arg Phe Ser Gly Ser
        50                  55                  60

Gly Ser Gly Thr Thr Tyr Ser Met Thr Ile Ser Ser Leu Glu Ala Glu
 65                 70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
```

-continued

<210> SEQ ID NO 9
<211> LENGTH: 122
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 9

Glu Val Gln Leu Gln Gln Ser Gly Ala Glu Leu Val Lys Pro Gly Ala
1               5                   10                  15

Ser Val Lys Met Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Ala Thr Leu Thr Ala Asp Lys Ser Ser Thr Ala Tyr
65                  70                  75                  80

Met Gln Leu Ser Ser Leu Thr Ser Glu Asp Ser Ala Asp Tyr Tyr Cys
                85                  90                  95

Ala Arg Ser Asn Tyr Tyr Gly Ser Ser Tyr Trp Phe Phe Asp Val Trp
            100                 105                 110

Gly Ala Gly Thr Thr Val Thr Val Ser Ser
        115                 120

<210> SEQ ID NO 10
<211> LENGTH: 122
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 10

Glu Val Gln Leu Gln Gln Ser Gly Ala Glu Leu Lys Lys Pro Gly Ala
1               5                   10                  15

Ser Val Lys Val Ser Cys Lys Ala Ser Gly Tyr Thr Phe Thr Ser Tyr
            20                  25                  30

Asn Met His Trp Val Lys Gln Thr Pro Gly Gln Gly Leu Glu Trp Ile
        35                  40                  45

Gly Ala Ile Tyr Pro Gly Asn Gly Asp Thr Ser Tyr Asn Gln Lys Phe
    50                  55                  60

Lys Gly Lys Thr Thr Leu Thr Ala Asp Lys Ser Ser Ser Thr Ala Tyr
65                  70                  75                  80

Met Glu Leu Ser Ser Leu Arg Ser Glu Asp Thr Ala Val Tyr Tyr Cys
                85                  90                  95

Ala Arg Ser Asn Tyr Tyr Gly Ser Ser Tyr Trp Phe Phe Asp Val Trp
            100                 105                 110

Gly Thr Gly Thr Thr Val Thr Val Ser Ser
        115                 120

<210> SEQ ID NO 11
<211> LENGTH: 106
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 11

```
Asp Ile Val Leu Thr Gln Ser Pro Ala Ile Leu Ser Ala Ser Pro Gly
1               5                   10                  15

Glu Lys Val Thr Met Thr Cys Arg Ala Ser Ser Ser Val Asn Tyr Met
                20                  25                  30

Asp Trp Tyr Gln Lys Pro Gly Ser Ser Pro Lys Pro Trp Ile Tyr
            35                  40                  45

Ala Thr Ser Asn Leu Ala Ser Gly Val Pro Ala Arg Phe Ser Gly Ser
        50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ser Phe Asn Pro Pro Thr
                85                  90                  95

Phe Gly Gly Gly Thr Lys Leu Glu Ile Lys
            100                 105
```

<210> SEQ ID NO 12
<211> LENGTH: 106
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 12

```
Asp Ile Val Leu Thr Gln Ser Pro Ala Ile Ile Thr Ala Ser Pro Gly
1               5                   10                  15

Glu Lys Val Thr Met Thr Cys Arg Ala Ser Ser Ser Val Asn Tyr Met
                20                  25                  30

Asp Trp Tyr Gln Lys Pro Gly Ser Ser Pro Lys Pro Trp Ile Tyr
            35                  40                  45

Ala Thr Ser Asn Leu Ala Ser Gly Val Pro Ser Arg Phe Ser Gly Ser
        50                  55                  60

Gly Ser Gly Thr Thr Tyr Ser Met Thr Ile Ser Ser Leu Glu Ala Glu
65                  70                  75                  80

Asp Ala Ala Thr Tyr Tyr Cys Gln Gln Trp Ser Phe Asn Pro Pro Thr
                85                  90                  95

Phe Gly Gly Gly Thr Lys Leu Glu Ile Lys
            100                 105
```

<210> SEQ ID NO 13
<211> LENGTH: 123
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 13

```
Gln Val Gln Leu Gln Gln Pro Gly Ala Glu Leu Val Lys Pro Gly Ala
1               5                   10                  15

Ser Val Lys Met Ser Cys Lys Thr Ser Gly Tyr Thr Phe Thr Ser Tyr
                20                  25                  30

Asn Val His Trp Val Lys Gln Thr Pro Gly Gln Gly Leu Glu Trp Ile
            35                  40                  45

Gly Ala Ile Tyr Pro Gly Asn Gly Asp Thr Ser Phe Asn Gln Lys Phe
        50                  55                  60

Lys Gly Lys Ala Thr Leu Thr Ala Asp Lys Ser Ser Ser Thr Val Tyr
65                  70                  75                  80

Met Gln Leu Ser Ser Leu Thr Ser Glu Asp Ser Ala Val Tyr Tyr Cys
                85                  90                  95
```

Ala Arg Ser Asn Tyr Tyr Gly Ser Ser Tyr Val Trp Phe Phe Asp Val
            100                 105                 110

Trp Gly Ala Gly Thr Thr Gly Thr Gly Ser Ser
        115                 120

<210> SEQ ID NO 14
<211> LENGTH: 106
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 14

Gln Ile Val Leu Ser Gln Ser Pro Thr Ile Leu Ser Ala Ser Pro Gly
1               5                   10                  15

Glu Lys Val Thr Met Thr Cys Arg Ala Ser Ser Ser Val Ser Tyr Met
            20                  25                  30

Asp Trp Tyr Gln Gln Lys Pro Gly Ser Ser Pro Lys Pro Trp Ile Tyr
        35                  40                  45

Ala Thr Ser Asn Leu Ala Ser Gly Val Pro Ala Arg Phe Ser Gly Ser
    50                  55                  60

Gly Ser Gly Thr Ser Tyr Ser Leu Thr Ile Ser Arg Val Glu Ala Glu
65                  70                  75                  80

Asp Ala Ala Thr Tyr Tyr Cys Gln Gln Trp Ile Ser Asn Pro Pro Thr
                85                  90                  95

Phe Gly Ala Gly Thr Lys Leu Glu Leu Lys
            100                 105

<210> SEQ ID NO 15
<211> LENGTH: 11
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 15

Ser Gly Ala Glu Leu Lys Lys Pro Gly Ala Ser
1               5                   10

<210> SEQ ID NO 16
<211> LENGTH: 9
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 16

Val Ser Cys Lys Ala Ser Gly Tyr Thr
1               5

<210> SEQ ID NO 17
<211> LENGTH: 8
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 17

Leu Glu Trp Thr Gly Ala Ile Tyr
1               5

<210> SEQ ID NO 18
<211> LENGTH: 9
<212> TYPE: PRT

```
<213> ORGANISM: Artificial Sequence
<220> FEATURE:
<223> OTHER INFORMATION: ANTIBODY VARIABLE REGION FRAGMENT

<400> SEQUENCE: 18

Tyr Asn Gln Lys Phe Lys Gly Lys Thr
1               5

<210> SEQ ID NO 19
<211> LENGTH: 9
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 19

Phe Lys Gly Lys Thr Thr Leu Thr Ala
1               5

<210> SEQ ID NO 20
<211> LENGTH: 9
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 20

Tyr Met Glu Leu Ser Ser Leu Arg Ser
1               5

<210> SEQ ID NO 21
<211> LENGTH: 10
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 21

Ser Ser Leu Arg Ser Glu Asp Thr Ala Val
1               5                   10

<210> SEQ ID NO 22
<211> LENGTH: 9
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 22

Asp Trp Gly Thr Gly Thr Thr Val Thr
1               5

<210> SEQ ID NO 23
<211> LENGTH: 10
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 23

Ile Ile Thr Ala Ser Pro Gly Glu Lys Val
1               5                   10

<210> SEQ ID NO 24
<211> LENGTH: 9
<212> TYPE: PRT
<213> ORGANISM: Artificial Sequence
<220> FEATURE:
```

<223> OTHER INFORMATION: ANTIBODY VARIABLE REGION FRAGMENT

<400> SEQUENCE: 24

Cys Arg Ala Ser Thr Ser Ala Ser Tyr
1               5

<210> SEQ ID NO 25
<211> LENGTH: 8
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 25

Gln Gln Lys Pro Thr Ser Ser Pro
1               5

<210> SEQ ID NO 26
<211> LENGTH: 9
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 26

Leu Ala Ser Gly Val Pro Ser Arg Phe
1               5

<210> SEQ ID NO 27
<211> LENGTH: 9
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 27

Phe Ser Gly Ser Gly Ser Gly Thr Thr
1               5

<210> SEQ ID NO 28
<211> LENGTH: 9
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 28

Tyr Ser Met Thr Ile Ser Ser Leu Glu
1               5

<210> SEQ ID NO 29
<211> LENGTH: 17
<212> TYPE: PRT
<213> ORGANISM: Mus musculus

<400> SEQUENCE: 29

Cys Glu Pro Ala Asn Pro Ser Glu Lys Asn Ser Pro Ser Thr Gln Tyr
1               5                   10                  15

Cys

<210> SEQ ID NO 30
<211> LENGTH: 9
<212> TYPE: PRT
<213> ORGANISM: Artificial Sequence
<220> FEATURE:
<223> OTHER INFORMATION: ANTIBODY VARIABLE REGION FRAGMENT

```
<400> SEQUENCE: 30

Met Ser Cys Lys Ala Ser Gly Tyr Thr
1               5

<210> SEQ ID NO 31
<211> LENGTH: 9
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 31

Tyr Asn Gln Lys Phe Lys Gly Lys Ala
1               5

<210> SEQ ID NO 32
<211> LENGTH: 9
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 32

Phe Lys Gly Lys Ala Thr Leu Thr Ala
1               5

<210> SEQ ID NO 33
<211> LENGTH: 9
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 33

Tyr Met Gln Leu Ser Ser Leu Arg Ser
1               5

<210> SEQ ID NO 34
<211> LENGTH: 10
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 34

Ile Leu Ser Ala Ser Pro Gly Glu Lys Val
1               5                   10

<210> SEQ ID NO 35
<211> LENGTH: 10
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 35

Leu Ala Ser Gly Val Pro Val Ala Arg Phe
1               5                   10

<210> SEQ ID NO 36
<211> LENGTH: 9
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 36
```

```
<210> SEQ ID NO 37
<211> LENGTH: 9
<212> TYPE: PRT
<213> ORGANISM: Artificial Sequence
<220> FEATURE:
<223> OTHER INFORMATION: ANTIBODY VARIABLE REGION FRAGMENT

<400> SEQUENCE: 37

Tyr Ser Leu Thr Ile Ser Arg Val Glu
  1               5

<210> SEQ ID NO 38
<211> LENGTH: 17
<212> TYPE: PRT
<213> ORGANISM: Homo sapiens

<400> SEQUENCE: 38

Cys Glu Pro Ser Asn Ser Ser Glu Lys Asn Ser Pro Ser Thr Gln Tyr
  1               5                  10                  15

Cys

<210> SEQ ID NO 39
<211> LENGTH: 992
<212> TYPE: DNA
<213> ORGANISM: Artificial Sequence
<220> FEATURE:
<223> OTHER INFORMATION: ANTIBODY FRAGMENT DNA

<400> SEQUENCE: 39
gacatcgttc tgacccagtc tccagcaatc ttgtctgcat ctccagggga gaaggtcacc     60
atgacctgca gagccagctc aagtgtaaat tacatggact ggtaccagaa gaagccaggc    120
tcctccccca aaccttggat ttatgccaca tccaacctgg cttctggagt ccctgctcgc    180
ttctctggca gtgggtctgg gacctcttac tctctcacaa tcagcagagt cgaggctgaa    240
gatgctgcca cttattactg ccagcagtgg agcttcaacc cacccacgtt cggtggtggg    300
accaagctgg agatcaaacg taagtggatc ccgcaattct aaactctgag ggggtcggat    360
gacgtggcca ttctttgcct aaagcattga gtttactgca aggtcagaaa agcatgcaaa    420
gccctcagaa tggctgcaaa gagctccaac aaaacaattt agaactttat taaggaatag    480
ggggaagcta ggaagaaact caaaacatca gatttttaaa tacgcttctt ggtctccttg    540
ctataattat ctgggataag catgctgttt tctgtctgtc cctaacatgc cctgtgatta    600
tccgcaaaca acacacccaa gggcagaact ttgttactta acaccatcc  tgtttgcttc    660
tttcctcagg aactgtggct gcaccatctg tcttcatctt cccgccatct gatgagcagt    720
tgaaatctgg aactgcctct gttgtgtgcc tgctgaataa cttctatccc agagaggcca    780
aagtacagtg gaaggtggat aacgccctcc aatcgggtaa ctcccaggag agtgtcacag    840
agcaggacag caaggacagc acctacagcc tcagcagcac cctgacgctg agcaaagcag    900
actacgagaa acacaaagtc tacgcctgcg aagtcaccca tcagggcctg agctcgcccg    960
tcacaaagag cttcaacagg ggagagtgtt ag                                  992

<210> SEQ ID NO 40
<211> LENGTH: 992
<212> TYPE: DNA
<213> ORGANISM: Artificial Sequence
<220> FEATURE:
<223> OTHER INFORMATION: ANTIBODY FRAGMENT DNA
```

<400> SEQUENCE: 40

```
gacattgttc tcacccagtc tccagcaatc atcacagcat ctccagggga gaaggtcaca        60
atgacttgca gggccagctc aagtgtaaac tacatggact ggtaccagaa gaagccaggg       120
tcctccccca aaccctggat ttatgccaca tccaacctgg cttctggagt cccttctcgc       180
ttcagtggca gtgggtctgg gactacttac tctatgacca tcagcagcct cgaggctgaa       240
gatgctgcca cttattactg ccagcagtgg agcttcaacc cacccacgtt cggaggggg        300
accaagctgg aaatcaaacg taagtggatc ccgcaattct aaactctgag ggggtcggat       360
gacgtggcca ttctttgcct aaagcattga gtttactgca aggtcagaaa agcatgcaaa       420
gccctcagaa tggctgcaaa gagctccaac aaaacaattt agaactttat taaggaatag       480
ggggaagcta ggaagaaact caaaacatca agatttttaaa tacgcttctt ggtctccttg      540
ctataattat ctgggataag catgctgttt tctgtctgtc cctaacatgc cctgtgatta       600
tccgcaaaca acacacccaa gggcagaact ttgttactta aacaccatcc tgtttgcttc       660
tttcctcagg aactgtggct gcaccatctg tcttcatctt cccgccatct gatgagcagt       720
tgaaatctgg aactgcctct gttgtgtgcc tgctgaataa cttctatccc agagaggcca       780
aagtacagtg gaaggtggat aacgccctcc aatcgggtaa ctcccaggag agtgtcacag       840
agcaggacag caaggacagc acctacagcc tcagcagcac cctgacgctg agcaaagcag       900
actacgagaa acacaaagtc tacgcctgcg aagtcaccca tcaggcctg agctcgcccg        960
tcacaaagag cttcaacagg ggagagtgtt ag                                     992
```

<210> SEQ ID NO 41
<211> LENGTH: 2184
<212> TYPE: DNA
<213> ORGANISM: Artificial Sequence
<220> FEATURE:
<223> OTHER INFORMATION: ANTIBODY FRAGMENT DNA

<400> SEQUENCE: 41

```
gaggtccagc tccagcagtc tggagctgag ctggtgaagc ctggggcttc agtgaagatg        60
tcctgcaagg cttctggata cacattcact agttataata tgcactgggt aaagcagaca       120
cctggacagg gcctggaatg gattggagct atttatccag gaaatggtga tacttcctac       180
aatcagaagt tcaagggcaa ggccacactg actgcagaca atcctccag cacagcctac        240
atgcagctca gcagcctgac atctgaagac tctgctgact attactgtgc gaggagtaac       300
tactacggta gtagctactg gttcttcgat gtctggggcg cagggaccac ggtcaccgtc       360
tcttcaggta agtaagcttt tctggggcag gccaggcctg accttggctt tggggcaggg       420
agggggctaa ggtgaggcag gtggcgccag ccaggtgcac acccaatgcc catgagccca       480
gacactggac gctgaacctc gcggacagtt aagaacccag gggcctctgc gccctgggcc       540
cagctctgtc ccacaccgcg gtcacatggc accacctctc ttgcagcctc caccaagggc       600
ccatcggtct tccccctggc accctcctcc aagagcacct ctgggggcac agcggccctg       660
ggctgcctgg tcaaggacta cttccccgaa ccggtgacgg tgtcgtggaa ctcaggcgcc       720
ctgaccagcg gcgtgcacac cttcccggct gtcctacagt cctcaggact ctactccctc       780
agcagcgtgg tgaccgtgcc ctccagcagc ttgggcaccc agacctacat ctgcaacgtg       840
aatcacaagc ccagcaacac caaggtggac aagagagttg gtgagaggcc agcacaggga       900
gggagggtgt ctgctggaag ccaggctcag cgctcctgcc tggacgcatc ccggctatgc       960
agtcccagtc cagggcagca aggcaggccc cgtctgcctc ttcacccgga ggcctctgcc      1020
```

```
cgccccactc atgctcaggg agagggtctt ctggctttt  cccaggctc tgggcaggca    1080 caggctaggt gccctaacc caggcctgc acacaaaggg gcaggtgctg ggctcagacc    1140
tgccaagagc catatccggg aggaccctgc ccctgaccta agcccacccc aaaggccaaa    1200
ctctccactc cctcagctcg gacaccttct ctcctcccag attccagtaa ctcccaatct    1260
tctctctgca gagcccaaat cttgtgacaa aactcacaca tgcccaccgt gcccaggtaa    1320
gccagcccag gcctcgccct ccagctcaag gcgggacagg tgccctagag tagcctgcat    1380
ccagggacag gccccagccg ggtgctgaca cgtccacctc catctcttcc tcagcacctg    1440
aactcctggg gggaccgtca gtcttcctct tccccccaaa acccaaggac accctcatga    1500
tctcccggac ccctgaggtc acatgcgtgg tggtggacgt gagccacgaa gaccctgagg    1560
tcaagttcaa ctggtacgtg gacggcgtgg aggtgcataa tgccaagaca aagccgcggg    1620
aggagcagta caacagcacg taccgtgtgg tcagcgtcct caccgtcctg caccaggact    1680
ggctgaatgg caaggagtac aagtgcaagg tctccaacaa agcccctccca gcccccatcg    1740 agaaaaccat ctccaaagcc aaaggtggga cccgtggggt gcgagggcca catggacaga    1800
ggccggctcg gcccaccctc tgccctgaga gtgaccgctg taccaacctc tgtccctaca    1860
gggcagcccc gagaaccaca ggtgtacacc ctgcccccat cccgggagga gatgaccaag    1920
aaccaggtca gcctgacctg cctggtcaaa ggcttctatc ccagcgacat cgccgtggag    1980
tgggagagca atgggcagcc ggagaacaac tacaagacca cgcctcccgt gctggactcc    2040
gacggctcct tcttcctcta tagcaagctc accgtggaca agagcaggtg gcagcagggg    2100
aacgtcttct catgctccgt gatgcatgag gctctgcaca accactacac gcagaagagc    2160 ctctcccctgt ccccgggtaa atga                                          2184

<210> SEQ ID NO 42
<211> LENGTH: 2179
<212> TYPE: DNA
<213> ORGANISM: Artificial Sequence
<220> FEATURE:
<223> OTHER INFORMATION: ANTIBODY FRAGMENT DNA

<400> SEQUENCE: 42
gaggtacaac tgcagcagtc tggggctgag ctgaagaagc ctggggcctc agtgaaggtg      60
tcctgcaagg cttctggcta cacatttacc agttacaata tgcactgggt aaaacagaca     120
cctggtcagg gcctggaatg gattggagct atttatcccg gaaatggtga tacttcctac     180
aatcagaagt tcaaaggcaa gacaacattg actgcagaca aatcctccag cacagcctac     240
atggaactca gcagcctgag atctgaggac actgcggtct attactgtgc aagatcgaat     300
tactacggca gcagctactg gttcttcgat gtctggggca ccgggaccac ggtcaccgtc     360
tcttcaggta agctttctgg ggcaggccag gcctgacctt ggctttgggg cagggagggg     420
gctaaggtga ggcaggtggc gccagccagg tgcacaccca atgcccatga gcccagacac     480
tggacgctga acctcgcgga cagttaagaa cccaggggcc tctgcgccct gggcccagct     540
ctgtcccaca ccgcggtcac atggcaccac ctctcttgca gcctccacca agggcccatc     600
ggtcttcccc ctggcaccct cctccaagag cacctctggg ggcacagcgg ccctgggctg     660
cctggtcaag gactacttcc ccgaaccggt gacggtgtcg tggaactcag cgccctgac    720 cagcggcgtg cacaccttcc cggctgtcct acagtcctca ggactctact ccctcagcag     780
cgtggtgacc gtgccctcca gcagcttggg cacccagacc tacatctgca acgtgaatca     840
caagcccagc aacaccaagg tggacaagag agttggtgag aggccagcac agggagggag     900
```

```
ggtgtctgct ggaagccagg ctcagcgctc ctgcctggac gcatcccggc tatgcagtcc    960
cagtccaggg cagcaaggca ggccccgtct gcctcttcac ccggaggcct ctgcccgccc   1020
cactcatgct cagggagagg gtcttctggc ttttccccca ggctctgggc aggcacaggc   1080
taggtgcccc taacccaggc cctgcacaca aaggggcagg tgctgggctc agacctgcca   1140
agagccatat ccgggaggac cctgcccctg acctaagccc accccaaagg ccaaactctc   1200
cactccctca gctcggacac cttctctcct cccagattcc agtaactccc aatcttctct   1260
ctgcagagcc caaatcttgt gacaaaactc acacatgccc accgtgccca ggtaagccag   1320
cccaggcctc gccctccagc tcaaggcggg acaggtgccc tagagtagcc tgcatccagg   1380
gacaggcccc agccgggtgc tgacacgtcc acctccatct cttcctcagc acctgaactc   1440 ctgggggggac cgtcagtctt cctcttcccc ccaaaaccca aggacaccct catgatctcc   1500
cggacccctg aggtcacatg cgtggtggtg gacgtgagcc acgaagaccc tgaggtcaag   1560
ttcaactggt acgtggacgg cgtggaggtg cataatgcca agacaaagcc gcgggaggag   1620
cagtacaaca gcacgtaccg tgtggtcagc gtcctcaccg tcctgcacca ggactggctg   1680
aatggcaagg agtacaagtg caaggtctcc aacaaagccc tcccagcccc catcgagaaa   1740
accatctcca aagccaaagg tgggacccgt ggggtgcgag ggccacatgg acagaggccg   1800
gctcggccca ccctctgccc tgagagtgac cgctgtacca acctctgtcc ctacagggca   1860
gccccgagaa ccacaggtgt acaccctgcc cccatcacgg aggagatgac caagaaccca   1920
ggtcagcctg acctgcctgg tcaaaggctt ctatcccagc gacatcgccg tggagtggga   1980
gagcaatggg cagccggaga caactacaag gaccacgcct cccgtgctgg actccgacgg   2040
ctccttcttc ctctatagca agctcaccgt ggacaagagc aggtggcagc aggggaacgt   2100
cttctcatgc tccgtgatgc atgaggctct gcacaaccac tacacgcaga gagcctctc    2160 cctgtccccg ggtaaatga                                                2179

<210> SEQ ID NO 43
<211> LENGTH: 2578
<212> TYPE: DNA
<213> ORGANISM: Artificial Sequence
<220> FEATURE:
<223> OTHER INFORMATION: ANTIBODY FRAGMENT DNA

<400> SEQUENCE: 43
gaggtacaac tgcagcagtc tggggctgag ctgaagaagc ctggggcctc agtgaaggtg     60
tcctgcaagg cttctggcta cacatttacc agttacaata tgcactgggt aaaacagaca    120
cctggtcagg gcctggaatg gattggagct atttatcccg gaaatggtga tacttcctac    180
aatcagaagt tcaaaggcaa gacaacattg actgcagaca aatcctccag cacagcctac    240
atggaactca gcagcctgag atctgaggac actgcggtct attactgtgc aagatcgaat    300
tactacggca gcagctactg gttcttcgat gtctgggca ccgggaccac ggtcaccgtc    360
tcttcaggta gctttctgg ggcaggccag gcctgacctt ggctttgggg cagggagggg    420
gctaaggtga ggcaggtggc gccagccagg tgcacaccca atgcccatga gcccagacac    480
tggacgctga acctcgcgga cagttaagaa cccaggggcc tctgcgccct gggcccagct    540
ctgtcccaca ccgcggtcac atggcaccac ctctcttgca gcctccacca agggcccatc    600
ggtcttcccc ctggcaccct cctccaagag cacctctggg ggcacagcgg ccctgggctg    660
cctggtcaag gactacttcc ccgaaccggt gacggtgtcg tggaactcag cgccctgac     720 cagcggcgtg cacaccttcc cggctgtcct acagtcctca ggactctact ccctcagcag    780
```

```
cgtggtgacc gtgccctcca gcagcttggg cacccagacc tacatctgca acgtgaatca    840
caagcccagc aacaccaagg tggacaagag agttggtgag aggccagcac agggagggag    900
ggtgtctgct ggaagccagg ctcagcgctc ctgcctggac gcatcccggc tatgcagtcc    960
cagtccaggg cagcaaggca ggccccgtct gcctcttcac ccggaggcct ctgcccgccc   1020
cactcatgct cagggagagg gtcttctggc ttttccccca ggctctgggc aggcacaggc   1080
taggtgcccc taacccaggc cctgcacaca aggggcagg tgctgggctc agacctgcca    1140
agagccatat ccgggaggac cctgcccctg acctaagccc accccaaagg ccaaactctc   1200
cactccctca gctcggacac cttctctcct cccagattcc agtaactccc aatcttctct   1260
ctgcagagcc caaatcttgt gacaaaactc acacatgccc accgtgccca ggtaagccag   1320
cccaggcctc gccctccagc tcaaggcggg acaggtgccc tagagtagcc tgcatccagg   1380
gacaggcccc agccgggtgc tgacacgtcc acctccatct cttcctcagc acctgaactc   1440 ctgggggac cgtcagtctt cctcttcccc ccaaaaccca aggacaccct catgatctcc    1500
cggacccctg aggtcacatg cgtggtggtg gacgtgagcc acgaagaccc tgaggtcaag   1560
ttcaactggt acgtggacgg cgtggaggtg cataatgcca agacaaagcc gcgggaggag   1620
cagtacaaca gcacgtaccg tgtggtcagc gtcctcaccg tcctgcacca ggactggctg   1680
aatggcaagg agtacaagtg caaggtctcc aacaaagccc tcccagcccc catcgagaaa   1740
accatctcca agccaaaggt gggacccgt ggggtgcgag ggccacatgg acagaggccg    1800
gctcggccca ccctctgccc tgagagtgac cgctgtacca acctctgtcc ctacagggca   1860
gccccgagaa ccacaggtgt acaccctgcc cccatcacgg aggagatga ccaagaacca    1920 ggtcagcctg acctgcctgg tcaaaggctt ctatcccagc gacatcgccg tggagtggga   1980
gagcaatggg cagccggaga caactacaa gaccacgcct cccgtgctgg actccgacgg    2040
ctccttcttc ctctatagca agctcaccgt ggacaagagc aggtggcagc aggggaacgt   2100
cttctcatgc tccgtgatgc atgaggctct gcacaaccac tacacgcaga gagcgccac    2160 cgcgaccccg ggtgcagccc caacttcaag ttctacaaag aaaacacagc tgcaactgga   2220
gcatctcctg ctggatctcc agatgattct gaatggaatt aacaactaca gaatcccaa    2280 actcaccagg atgctcacat tcaagttcta catgcccaag aaggccacag agctcaaaca   2340
tctccagtgt ctagaggagg aactcaaacc tctggaggaa gtgctaaacc tcgctcagag   2400
caaaaacttc cacttaagac ctagggactt aatcagcaat atcaacgtaa tagttctgga   2460
actaaaggga tccgaaacaa cattcatgtg tgaatatgct gatgagacag caaccattgt   2520
agaattccta aacagatgga ttaccttttg tcaaagcatc atctcaacac taacttga     2578
```

<210> SEQ ID NO 44
<211> LENGTH: 7
<212> TYPE: PRT
<213> ORGANISM: Artificial Sequence
<220> FEATURE:
<223> OTHER INFORMATION: ANTIBODY VARIABLE REGION SEGMENT

<400> SEQUENCE: 44

Ala Thr Ala Thr Pro Gly Ala
1               5

<210> SEQ ID NO 45
<211> LENGTH: 7
<212> TYPE: PRT
<213> ORGANISM: Artificial Sequence
<220> FEATURE:

<223> OTHER INFORMATION: ANTIBODY VARIABLE REGION SEGMENT

<400> SEQUENCE: 45

Leu Ser Leu Ser Pro Gly Lys
 1               5

<210> SEQ ID NO 46
<211> LENGTH: 4
<212> TYPE: PRT
<213> ORGANISM: Artificial Sequence
<220> FEATURE:
<223> OTHER INFORMATION: synthetic fusion protein epitope

<400> SEQUENCE: 46

Leu Ser Leu Ser
 1

<210> SEQ ID NO 47
<211> LENGTH: 4
<212> TYPE: PRT
<213> ORGANISM: Artificial Sequence
<220> FEATURE:
<223> OTHER INFORMATION: synthetic fusion protein epitope

<400> SEQUENCE: 47

Ala Thr Ala Thr
 1

<210> SEQ ID NO 48
<211> LENGTH: 121
<212> TYPE: PRT
<213> ORGANISM: Artificial Sequence
<220> FEATURE:
<223> OTHER INFORMATION: synthetic polypeptide variant
<221> NAME/KEY: VARIANT
<222> LOCATION: 12, 14, 20, 48
<223> OTHER INFORMATION: Xaa 12 = Val or Lys
      Xaa 14 = Ala or Pro
      Xaa 20 = Met or Val
      Xaa 48 = Ile or Thr
<221> NAME/KEY: VARIANT
<222> LOCATION: 68, 82, 87
<223> OTHER INFORMATION: Xaa 68 = Ala or Thr
      Xaa 82 = Gln or Glu
      Xaa 87 = Thr or Arg
<221> NAME/KEY: VARIANT
<222> LOCATION: 91, 106
<223> OTHER INFORMATION: Xaa 91 = Ser or Thr
      Xaa 106 = Thr or Trp

<400> SEQUENCE: 48

Gln Val Gln Leu Gln Gln Pro Gly Ala Glu Leu Xaa Lys Xaa Gly Ala
 1               5                  10                  15

Ser Val Lys Xaa Ser Cys Lys Ala Ser Gly Tyr Thr Phe Thr Ser Tyr
                20                  25                  30

Asn Met His Trp Val Lys Gln Thr Pro Gly Arg Gly Leu Glu Trp Xaa
             35                  40                  45

Gly Ala Ile Tyr Pro Gly Asn Gly Asp Thr Ser Tyr Asn Gln Lys Phe
         50                  55                  60

Lys Gly Lys Xaa Thr Leu Thr Ala Asp Lys Ser Ser Ser Thr Ala Tyr
 65                  70                  75                  80

Met Xaa Leu Ser Ser Leu Xaa Ser Glu Asp Xaa Ala Val Tyr Tyr Cys
                 85                  90                  95

Ala Arg Ser Thr Tyr Tyr Gly Gly Asp Xaa Tyr Phe Asn Val Trp Gly
                100                 105                 110

Ala Gly Thr Thr Val Thr Val Ser Ala

```
<210> SEQ ID NO 49
<211> LENGTH: 106
<212> TYPE: PRT
<213> ORGANISM: Artificial Sequence
<220> FEATURE:
<223> OTHER INFORMATION: synthetic polypeptide variant
<221> NAME/KEY: VARIANT
<222> LOCATION: 11, 12, 27, 29
<223> OTHER INFORMATION: Xaa 11 = Leu or Ile
      Xaa 12 = Ser or Thr
      Xaa 27 = Ser or Thr
      Xaa 29 = Val or Ala
<221> NAME/KEY: VARIANT
<222> LOCATION: 40, 59, 69
<223> OTHER INFORMATION: Xaa 40 = Gly or Thr
      Xaa 59 = Val or Ser
      Xaa 69 = Ser or Thr
<221> NAME/KEY: VARIANT
<222> LOCATION: 72, 76, 77
<223> OTHER INFORMATION: Xaa 72 = Leu or Met
      Xaa 76 = Arg or Ser
      Xaa 77 = Val or Leu

<400> SEQUENCE: 49

Gln Ile Val Leu Ser Gln Ser Pro Ala Ile Xaa Xaa Ala Ser Pro Gly
 1               5                  10                  15

Glu Lys Val Thr Met Thr Cys Arg Ala Ser Xaa Ser Xaa Ser Tyr Ile
                20                  25                  30

His Trp Phe Gln Gln Lys Pro Xaa Ser Ser Pro Lys Pro Trp Ile Tyr
            35                  40                  45

Ala Thr Ser Asn Leu Ala Ser Gly Val Pro Xaa Arg Phe Ser Gly Ser
        50                  55                  60

Gly Ser Gly Thr Xaa Tyr Ser Xaa Thr Ile Ser Xaa Xaa Glu Ala Glu
65                  70                  75                  80

Asp Ala Ala Thr Tyr Tyr Cys Gln Gln Trp Thr Ser Asn Pro Pro Thr
                85                  90                  95

Phe Gly Gly Gly Thr Lys Leu Glu Ile Lys
            100                 105

<210> SEQ ID NO 50
<211> LENGTH: 122
<212> TYPE: PRT
<213> ORGANISM: Artificial Sequence
<220> FEATURE:
<223> OTHER INFORMATION: synthetic polypeptide variant
<221> NAME/KEY: VARIANT
<222> LOCATION: 12, 20, 68
<223> OTHER INFORMATION: Xaa 12 = Val or Lys
      Xaa 20 = Met or Val
      Xaa 68 = Ala or Thr
<221> NAME/KEY: VARIANT
<222> LOCATION: 82, 87, 91
<223> OTHER INFORMATION: Xaa 82 = Gln or Glu
      Xaa 87 = Thr or Arg
      Xaa 91 = Ser or Thr
<221> NAME/KEY: VARIANT
<222> LOCATION: 93, 114
<223> OTHER INFORMATION: Xaa 93 = Asp or Val
      Xaa 114 = Ala or Thr

<400> SEQUENCE: 50

Glu Val Gln Leu Gln Gln Ser Gly Ala Glu Leu Xaa Lys Pro Gly Ala
 1               5                  10                  15

Ser Val Lys Xaa Ser Cys Lys Ala Ser Gly Tyr Thr Phe Thr Ser Tyr
                20                  25                  30

Asn Met His Trp Val Lys Gln Thr Pro Gly Gln Gly Leu Glu Trp Ile
```

```
                    35                  40                  45
Gly Ala Ile Tyr Pro Gly Asn Gly Asp Thr Ser Tyr Asn Gln Lys Phe
            50                  55                  60

Lys Gly Lys Xaa Thr Leu Thr Ala Asp Lys Ser Ser Ser Thr Ala Tyr
 65                  70                  75                  80

Met Xaa Leu Ser Ser Leu Xaa Ser Glu Asp Xaa Ala Xaa Tyr Tyr Cys
                 85                  90                  95

Ala Arg Ser Asn Tyr Tyr Gly Ser Ser Tyr Trp Phe Phe Asp Val Trp
                100                 105                 110

Gly Xaa Gly Thr Thr Val Thr Val Ser Ser
        115                 120

<210> SEQ ID NO 51
<211> LENGTH: 106
<212> TYPE: PRT
<213> ORGANISM: Artificial Sequence
<220> FEATURE:
<223> OTHER INFORMATION: synthetic polypeptide variant
<221> NAME/KEY: VARIANT
<222> LOCATION: 11, 12, 59
<223> OTHER INFORMATION: Xaa 11 = Leu or Ile
      Xaa 12 = Ser or Thr
      Xaa 59 = Ala or Ser
<221> NAME/KEY: VARIANT
<222> LOCATION: 69, 72
<223> OTHER INFORMATION: Xaa 69 = Ser or Thr
      Xaa 72 = Leu or Met
<221> NAME/KEY: VARIANT
<222> LOCATION: 76, 77
<223> OTHER INFORMATION: Xaa 76 = Arg or Ser
      Xaa 77 = Val or Leu

<400> SEQUENCE: 51

Asp Ile Val Leu Thr Gln Ser Pro Ala Ile Xaa Xaa Ala Ser Pro Gly
 1               5                  10                  15

Glu Lys Val Thr Met Thr Cys Arg Ala Ser Ser Ser Val Asn Tyr Met
                 20                  25                  30

Asp Trp Tyr Gln Lys Lys Pro Gly Ser Ser Pro Lys Pro Trp Ile Tyr
             35                  40                  45

Ala Thr Ser Asn Leu Ala Ser Gly Val Pro Xaa Arg Phe Ser Gly Ser
         50                  55                  60

Gly Ser Gly Thr Xaa Tyr Ser Xaa Thr Ile Ser Xaa Xaa Glu Ala Glu
 65                  70                  75                  80

Asp Ala Ala Thr Tyr Tyr Cys Gln Gln Trp Ser Phe Asn Pro Pro Thr
                 85                  90                  95

Phe Gly Gly Gly Thr Lys Leu Glu Ile Lys
                100                 105
```